United States Patent
Cartledge et al.

(10) Patent No.: US 9,427,215 B2
(45) Date of Patent: Aug. 30, 2016

(54) MINIMALLY INVASIVE SYSTEM FOR DELIVERING AND SECURING AN ANNULAR IMPLANT

(75) Inventors: Richard G. Cartledge, Hollywood, FL (US); John P. Cartledge, Boca Raton, FL (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 1276 days.

(21) Appl. No.: 12/026,424

(22) Filed: Feb. 5, 2008

(65) Prior Publication Data

US 2008/0306586 A1    Dec. 11, 2008

Related U.S. Application Data

(60) Provisional application No. 60/888,214, filed on Feb. 5, 2007.

(51) Int. Cl.
*A61B 17/00* (2006.01)
*A61B 17/064* (2006.01)
(Continued)

(52) U.S. Cl.
CPC ....... *A61B 17/00234* (2013.01); *A61B 17/068* (2013.01); *A61B 17/0644* (2013.01); *A61F 2/2445* (2013.01); *A61F 2/2448* (2013.01);
(Continued)

(58) Field of Classification Search
CPC .... A61F 2/243; A61F 2/2466; A61F 2/2427; A61F 2/2442; A61F 2/24; A61F 2/2445; A61F 2002/011

USPC ...... 623/2.11, 1.23; 606/108, 139, 142, 144, 606/140, 200, 153
See application file for complete search history.

(56) References Cited

U.S. PATENT DOCUMENTS 4,042,979 A    8/1977  Angell
4,602,911 A    7/1986  Ahmadi et al.
(Continued)

FOREIGN PATENT DOCUMENTS

EP    0495417 A1    7/1992
EP    1554990 A2    7/2005
(Continued)

OTHER PUBLICATIONS

PCT International Search Report for PCT/US08/53084 dated Aug. 15, 2008 (2 pages).
(Continued)

*Primary Examiner* — Alexander Orkin
(74) *Attorney, Agent, or Firm* — Lerner, David, Littenberg, Krumholz & Mentlik, LLP

(57) ABSTRACT

A delivery device for an annular implant is provided, comprising an annular implant having an adjustable dimension; a plurality of movable elongated deployment members, each having a proximal end and a distal end and an annular implant deployment region therebetween; and a distal joining member for joining the distal ends of the deployment members, wherein the deployment members are expandable by an expansion means to a deployment configuration, and the implant deployment regions of the deployment members are substantially parallel in an expanded configuration. The annular implant can comprise an adjustment mechanism in communication with a releasably attached elongated adjustment tool, whereby the size or shape of the annular implant can be incrementally adjusted.

22 Claims, 34 Drawing Sheets

(51) Int. Cl.
*A61B 17/068* (2006.01)
*A61F 2/24* (2006.01)
*A61F 5/00* (2006.01)
A61B 18/00 (2006.01)

(52) U.S. Cl.
CPC .......... *A61F 2/2466* (2013.01); *A61F 5/0003* (2013.01); *A61B 2017/00247* (2013.01); *A61B 2017/00783* (2013.01); *A61B 2017/00827* (2013.01); *A61B 2017/0647* (2013.01); *A61B 2017/0649* (2013.01); *A61B 2018/00392* (2013.01)

(56) References Cited

U.S. PATENT DOCUMENTS

| | | | |
|---|---|---|---|
| 4,676,253 A | 6/1987 | Newman et al. | |
| 5,064,431 A | 11/1991 | Gilbertson et al. | |
| 5,102,417 A | 4/1992 | Palmaz | |
| 5,119,674 A | 6/1992 | Nielsen | |
| 5,201,880 A | 4/1993 | Wright et al. | |
| 5,243,976 A | 9/1993 | Ferek-Petric et al. | |
| 5,306,296 A | 4/1994 | Wright et al. | |
| 5,411,552 A | 5/1995 | Andersen et al. | |
| 5,423,851 A | 6/1995 | Samuels | |
| 5,443,477 A | 8/1995 | Marin et al. | |
| 5,522,884 A | 6/1996 | Wright et al. | |
| 5,593,424 A | 1/1997 | Northrup, III et al. | |
| 5,601,604 A | 2/1997 | Vincent | |
| 5,674,279 A | 10/1997 | Wright et al. | |
| 5,695,515 A * | 12/1997 | Orejola | 606/191 |
| 5,709,695 A | 1/1998 | Northrup, III et al. | |
| 5,713,951 A | 2/1998 | Garrison et al. | |
| 5,769,812 A | 6/1998 | Stevens | |
| 5,814,097 A | 9/1998 | Sterman et al. | |
| 5,885,228 A * | 3/1999 | Rosenman et al. | 600/587 |
| 5,908,435 A | 6/1999 | Samuels | |
| 5,961,539 A | 10/1999 | Northrup, III et al. | |
| 5,972,030 A | 10/1999 | Garrison et al. | |
| 5,976,159 A | 11/1999 | Bolduc et al. | |
| 5,984,959 A | 11/1999 | Robertson et al. | |
| 5,989,284 A | 11/1999 | Laufer | |
| 6,067,991 A | 5/2000 | Forsell | |
| 6,110,200 A | 8/2000 | Hinnenkamp | |
| 6,152,144 A | 11/2000 | Lesh et al. | |
| 6,162,237 A * | 12/2000 | Chan | 606/198 |
| 6,168,614 B1 | 1/2001 | Andersen et al. | |
| 6,168,616 B1 | 1/2001 | Brown, III | |
| 6,187,040 B1 | 2/2001 | Wright | |
| 6,217,610 B1 | 4/2001 | Carpentier et al. | |
| 6,254,615 B1 | 7/2001 | Bolduc et al. | |
| 6,269,819 B1 | 8/2001 | Oz et al. | |
| 6,355,030 B1 | 3/2002 | Aldrich et al. | |
| 6,368,348 B1 | 4/2002 | Gabbay | |
| 6,402,781 B1 | 6/2002 | Langberg et al. | |
| 6,406,493 B1 | 6/2002 | Tu et al. | |
| 6,416,522 B1 * | 7/2002 | Strecker | 606/143 |
| 6,419,696 B1 | 7/2002 | Ortiz et al. | |
| 6,451,054 B1 | 9/2002 | Stevens | |
| 6,461,365 B2 | 10/2002 | Bolduc et al. | |
| 6,464,707 B1 | 10/2002 | Bjerken | |
| 6,470,892 B1 | 10/2002 | Forsell | |
| 6,485,496 B1 * | 11/2002 | Suyker et al. | 606/153 |
| 6,511,489 B2 * | 1/2003 | Field et al. | 606/148 |
| 6,514,265 B2 | 2/2003 | Ho et al. | |
| 6,524,338 B1 | 2/2003 | Gundry | |
| 6,537,314 B2 | 3/2003 | Langberg et al. | |
| 6,551,332 B1 | 4/2003 | Nguyen et al. | |
| 6,564,805 B2 | 5/2003 | Garrison et al. | |
| 6,582,462 B1 | 6/2003 | Andersen et al. | |
| 6,607,541 B1 | 8/2003 | Gardiner et al. | |
| 6,613,059 B2 | 9/2003 | Schaller et al. | |
| 6,619,291 B2 | 9/2003 | Hlavka et al. | |
| 6,629,534 B1 | 10/2003 | St. Goar et al. | |
| 6,641,593 B1 | 11/2003 | Schaller et al. | |
| 6,651,671 B1 | 11/2003 | Donlon et al. | |
| 6,689,164 B1 | 2/2004 | Seguin | |
| 6,706,065 B2 | 3/2004 | Langberg et al. | |
| 6,709,456 B2 | 3/2004 | Langberg et al. | |
| 6,716,243 B1 | 4/2004 | Colvin et al. | |
| 6,723,038 B1 | 4/2004 | Schroeder et al. | |
| 6,749,630 B2 | 6/2004 | McCarthy et al. | |
| 6,767,362 B2 | 7/2004 | Schreck | |
| 6,776,789 B2 | 8/2004 | Bryant et al. | |
| 6,793,673 B2 | 9/2004 | Kowalsky et al. | |
| 6,797,002 B2 | 9/2004 | Spence et al. | |
| 6,810,882 B2 | 11/2004 | Langberg et al. | |
| 6,824,562 B2 | 11/2004 | Mathis et al. | |
| 6,840,246 B2 | 1/2005 | Downing | |
| 6,872,223 B2 | 3/2005 | Roberts et al. | |
| 6,893,459 B1 | 5/2005 | Macoviak | |
| 6,908,482 B2 | 6/2005 | McCarthy et al. | |
| 6,911,035 B1 | 6/2005 | Blomme | |
| 6,921,407 B2 | 7/2005 | Nguyen et al. | |
| 6,926,715 B1 | 8/2005 | Hauck et al. | |
| 6,942,694 B2 | 9/2005 | Liddicoat et al. | |
| 6,986,738 B2 | 1/2006 | Glukhovsky et al. | |
| 7,087,066 B2 | 8/2006 | Bolduc et al. | |
| 7,175,660 B2 | 2/2007 | Cartledge et al. | |
| 7,285,087 B2 | 10/2007 | Moaddeb et al. | |
| 7,297,150 B2 | 11/2007 | Cartledge et al. | |
| 7,335,213 B1 * | 2/2008 | Hyde et al. | 606/151 |
| 7,455,690 B2 | 11/2008 | Cartledge et al. | |
| 2001/0002445 A1 * | 5/2001 | Vesely | 623/2.11 |
| 2001/0044656 A1 * | 11/2001 | Williamson et al. | 623/2.11 |
| 2002/0128708 A1 | 9/2002 | Northrup, III et al. | |
| 2002/0151967 A1 | 10/2002 | Mikus et al. | |
| 2003/0050693 A1 | 3/2003 | Quijano et al. | |
| 2003/0050694 A1 * | 3/2003 | Yang et al. | 623/2.11 |
| 2003/0074012 A1 | 4/2003 | Nguyen et al. | |
| 2003/0083742 A1 | 5/2003 | Spence et al. | |
| 2003/0093148 A1 | 5/2003 | Bolling et al. | |
| 2003/0199974 A1 | 10/2003 | Lee et al. | |
| 2003/0233142 A1 | 12/2003 | Morales et al. | |
| 2004/0019378 A1 | 1/2004 | Hlavka et al. | |
| 2004/0030382 A1 | 2/2004 | St. Goar et al. | |
| 2004/0049210 A1 | 3/2004 | Van Tassel et al. | |
| 2004/0087965 A1 | 5/2004 | Levine et al. | |
| 2004/0088047 A1 | 5/2004 | Spence et al. | |
| 2004/0111099 A1 | 6/2004 | Nguyen et al. | |
| 2004/0127980 A1 | 7/2004 | Kowalsky et al. | |
| 2004/0133147 A1 | 7/2004 | Woo | |
| 2004/0148019 A1 | 7/2004 | Vidlund et al. | |
| 2004/0148021 A1 | 7/2004 | Cartledge et al. | |
| 2004/0153144 A1 | 8/2004 | Seguin | |
| 2004/0153147 A1 | 8/2004 | Mathis | |
| 2004/0162611 A1 | 8/2004 | Marquez | |
| 2004/0172046 A1 | 9/2004 | Hlavka et al. | |
| 2004/0176840 A1 | 9/2004 | Langberg et al. | |
| 2004/0181238 A1 | 9/2004 | Zarbatany et al. | |
| 2004/0193191 A1 | 9/2004 | Starksen et al. | |
| 2004/0249453 A1 | 12/2004 | Cartledge et al. | |
| 2005/0060030 A1 | 3/2005 | Lashinski et al. | |
| 2005/0065550 A1 | 3/2005 | Starksen et al. | |
| 2005/0070999 A1 | 3/2005 | Spence | |
| 2005/0075659 A1 * | 4/2005 | Realyvasquez et al. | 606/167 |
| 2005/0107871 A1 * | 5/2005 | Realyvasquez et al. | 623/2.11 |
| 2005/0119734 A1 | 6/2005 | Spence et al. | |
| 2005/0119735 A1 | 6/2005 | Spence et al. | |
| 2005/0131533 A1 | 6/2005 | Alfieri et al. | |
| 2005/0149114 A1 | 7/2005 | Cartledge et al. | |
| 2005/0154412 A1 | 7/2005 | Krueger et al. | |
| 2005/0192601 A1 | 9/2005 | Demarais | |
| 2006/0034511 A1 | 2/2006 | Verstraelen et al. | |
| 2006/0106405 A1 | 5/2006 | Fann et al. | |
| 2006/0135967 A1 * | 6/2006 | Realyvasquez | 606/142 |
| 2006/0241748 A1 | 10/2006 | Lee et al. | |
| 2006/0253142 A1 | 11/2006 | Bjerken | |
| 2007/0016287 A1 | 1/2007 | Cartledge et al. | |
| 2007/0203560 A1 * | 8/2007 | Forster et al. | 623/1.11 |
| 2007/0299543 A1 | 12/2007 | Cartledge et al. | |
| 2008/0027483 A1 | 1/2008 | Cartledge et al. | |
| 2008/0039681 A1 | 2/2008 | Moaddeb et al. | |
| 2008/0109076 A1 | 5/2008 | Cartledge et al. | |

(56) References Cited

U.S. PATENT DOCUMENTS

| | | |
|---|---|---|
| 2008/0306586 A1 | 12/2008 | Cartledge et al. |
| 2009/0125102 A1 | 5/2009 | Cartledge et al. |
| 2009/0234404 A1 | 9/2009 | Fitzgerald et al. |
| 2010/0305609 A1 | 12/2010 | Cartledge et al. |
| 2011/0009956 A1 | 1/2011 | Cartledge et al. |
| 2011/0022168 A1 | 1/2011 | Cartledge |
| 2011/0066231 A1 | 3/2011 | Cartledge et al. |
| 2011/0093062 A1 | 4/2011 | Cartledge et al. |
| 2011/0196480 A1 | 8/2011 | Cartledge |
| 2011/0202130 A1 | 8/2011 | Cartledge et al. |
| 2011/0208295 A1 | 8/2011 | Cartledge et al. |
| 2011/0257633 A1 | 10/2011 | Cartledge et al. |

FOREIGN PATENT DOCUMENTS

| | | |
|---|---|---|
| EP | 1607048 A1 | 12/2005 |
| WO | WO 97/16135 | 5/1997 |
| WO | WO 99/04730 | 2/1999 |
| WO | WO 99/30647 | 6/1999 |
| WO | WO 00/03759 | 1/2000 |
| WO | 01/26586 A1 | 4/2001 |
| Wo | WO 01/26586 A1 | 4/2001 |
| WO | WO 01/50985 | 7/2001 |
| WO | WO 2004/012583 A2 | 2/2004 |
| WO | WO 2004/019816 A2 | 2/2004 |
| WO | WO 2004/060217 A1 | 7/2004 |
| WO | WO 2004/112585 A2 | 12/2004 |
| WO | WO 2004/112651 A2 | 12/2004 |
| WO | WO 2004/112658 A2 | 12/2004 |
| WO | WO 2005/007036 A1 | 1/2005 |
| WO | WO 2005/007037 A1 | 1/2005 |
| WO | WO 2005/007219 A2 | 1/2005 |
| WO | WO 2005/009285 A2 | 2/2005 |
| WO | WO 2005/025644 A2 | 3/2005 |
| WO | WO 2005/046488 A2 | 5/2005 |
| WO | WO 2005/055883 A1 | 6/2005 |
| WO | WO 2005/062931 A2 | 7/2005 |

OTHER PUBLICATIONS

U.S. Appl. No. 13/123,768.
Letter dated Jan. 27, 2011 from Richard H. Levinstein, Esq.

* cited by examiner

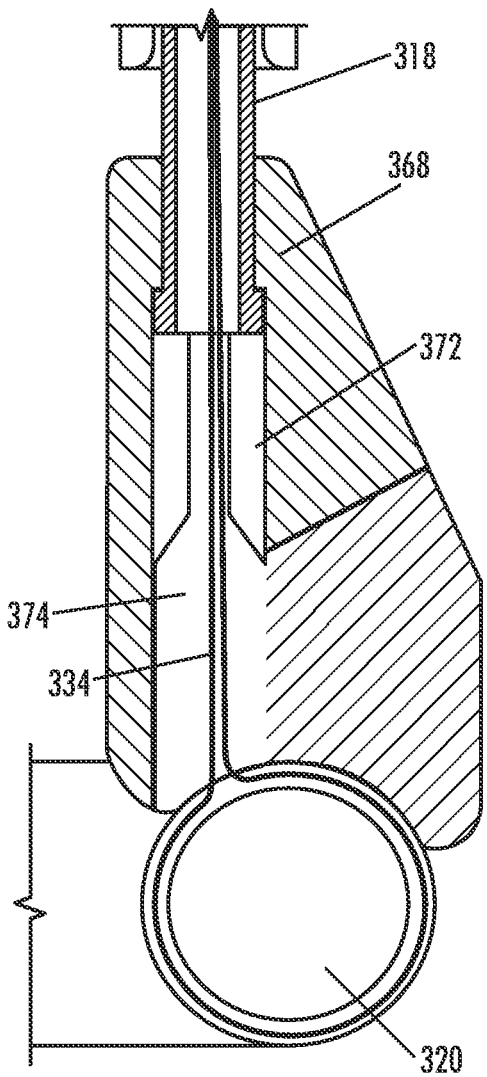
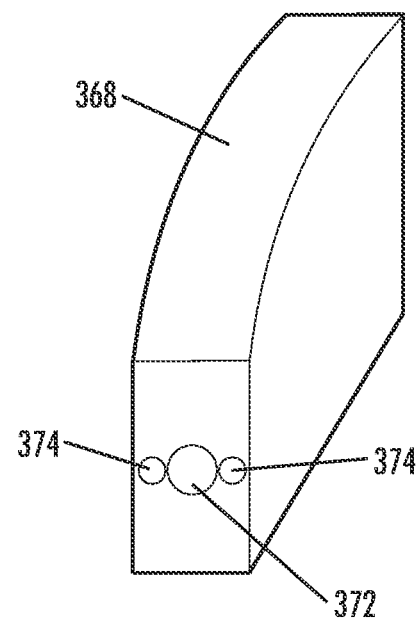
Fig. 26C
Fig. 26D
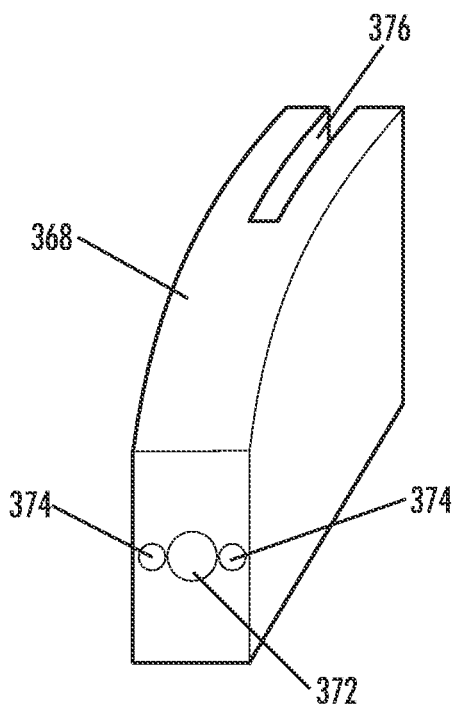
Fig. 26E

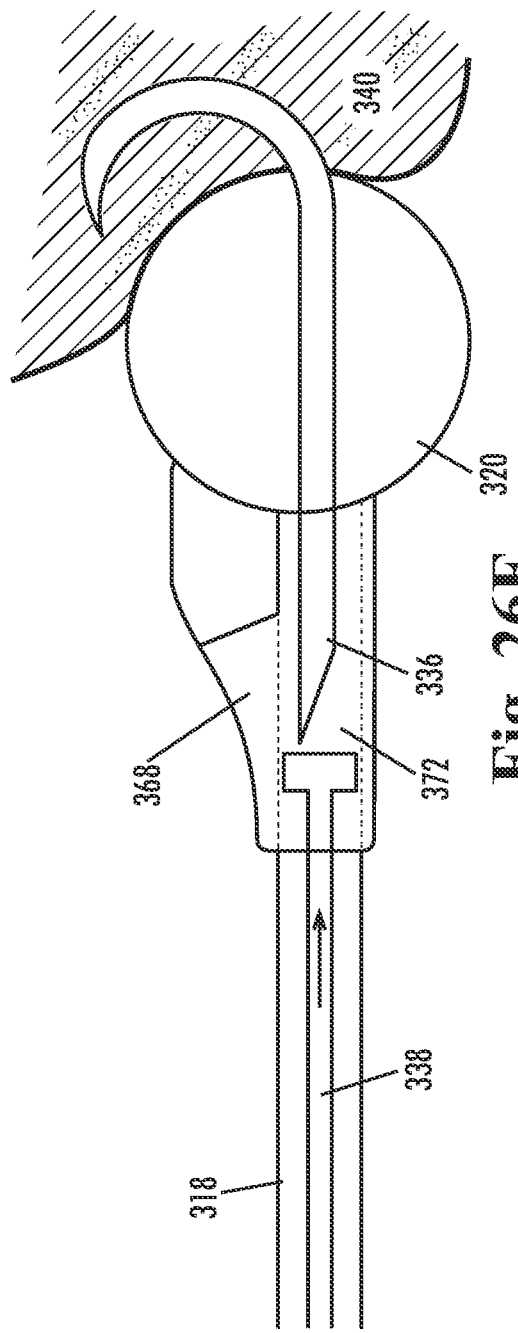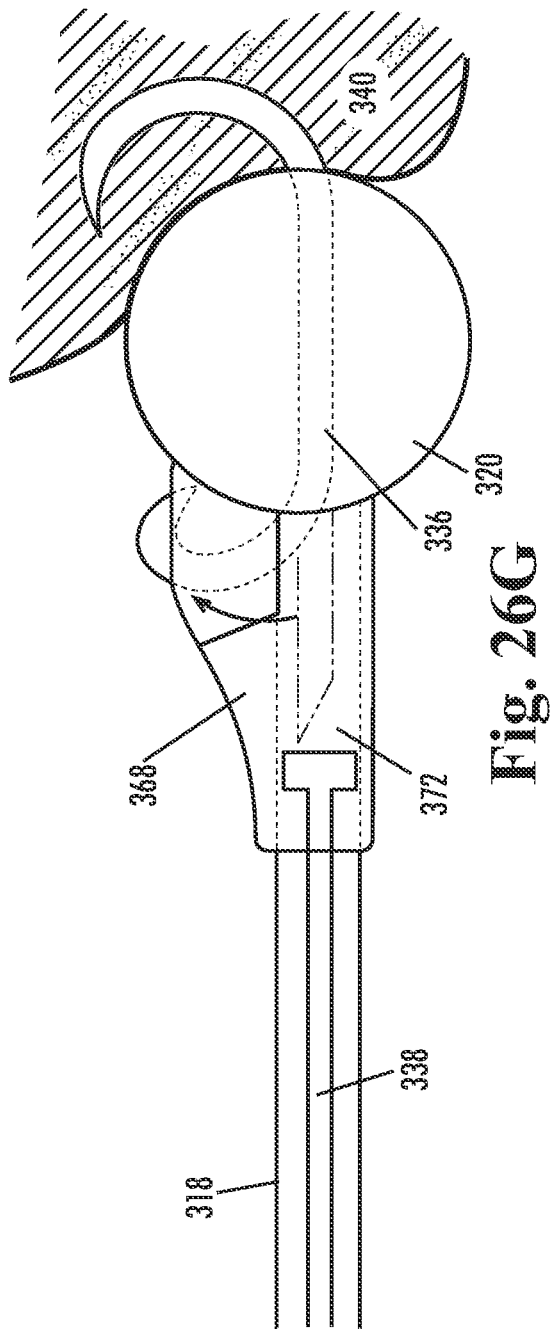

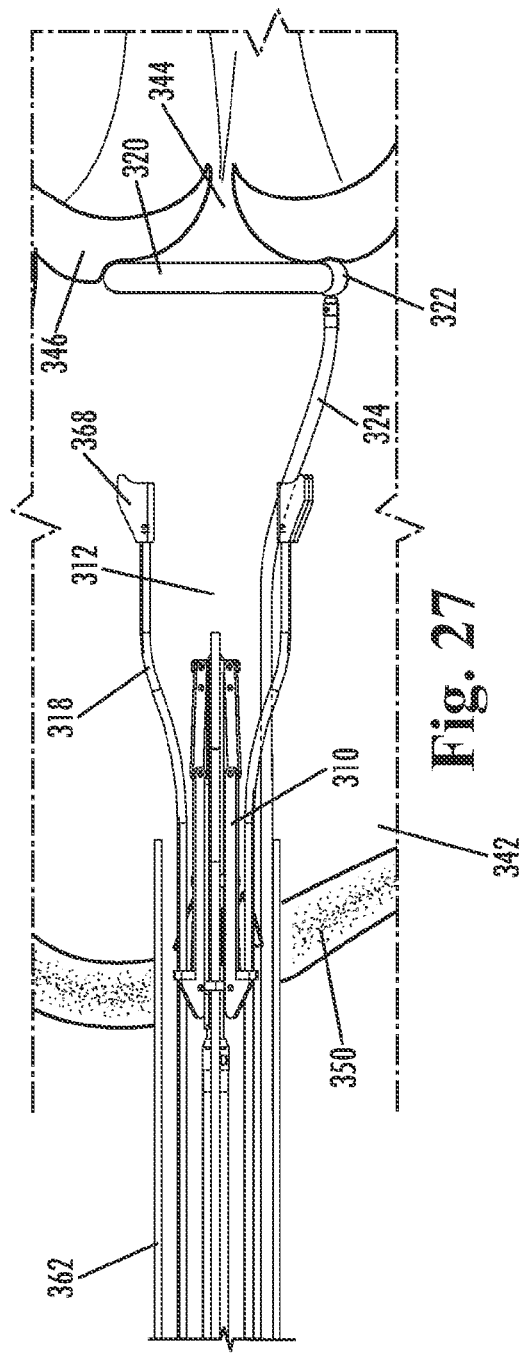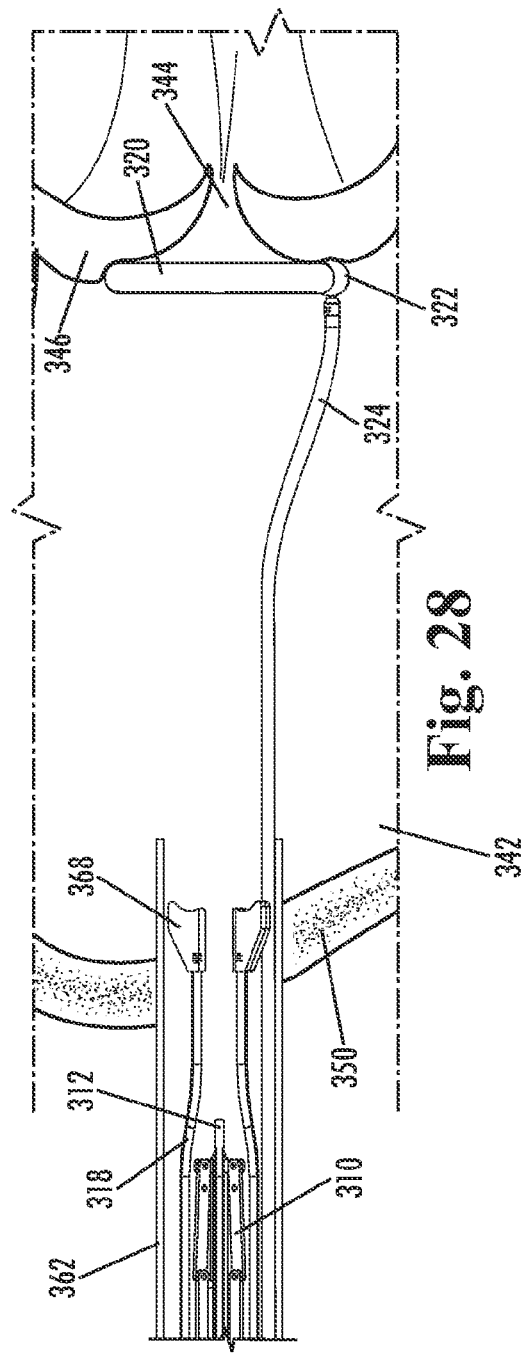

MINIMALLY INVASIVE SYSTEM FOR DELIVERING AND SECURING AN ANNULAR IMPLANT

CROSS REFERENCE TO RELATED APPLICATIONS

This application claims priority pursuant to 35 U.S.C. §119 based upon Provisional Application Ser. No. 60/888,214 filed Feb. 5, 2007, the entire disclosure of which is hereby incorporated by reference.

FIELD OF THE INVENTION

The present invention relates generally to the delivery of an implantable device, and more particularly to methods and devices for delivering and securing an annular implant to control the internal circumference of an annulus.

BACKGROUND OF THE INVENTION

Many anatomic structures in the mammalian body are hollow passages in which walls of tissue define an annulus, which serves as a conduit for blood, other physiologic fluids, nutrient matter, or waste matter passing within the structure. In many physiologic settings, dysfunction may result from a structural annulus which is either too large or too small. In most such cases, dysfunction can be relieved by interventional changes in the size of the annulus.

Thus in surgery, there is often a need to reduce the internal circumference of an annulus or other open anatomic structure to narrow the size of the annulus or opening to achieve a desired physiologic effect. Often, such surgical procedures require interruption in the normal physiologic flow of blood, other physiologic fluids, or other structural contents through the annulus or structure. The exact amount of the narrowing required for the desired effect often cannot be fully appreciated until physiologic flow through the annulus or structure is resumed. It would be advantageous, therefore, to have an adjustable means of achieving this narrowing effect, such that the degree of narrowing could be changed not only after its implantation, but after the resumption of normal physiologic flow in situ.

One example of a dysfunction within an anatomic lumen is in the area of cardiac surgery, and specifically valvular repair. Approximately one million open heart surgical procedures are now performed annually in the United States, and twenty percent of these operations are related to cardiac valves.

The field of cardiac surgery was previously transformed by the introduction of the pump oxygenator, which allowed open heart surgery to be performed. Valvular heart surgery was made possible by the further introduction of the mechanical ball-valve prosthesis, and many modifications and different forms of prosthetic heart valves have since been developed. However, the ideal prosthetic valve has yet to be designed, which attests to the elegant form and function of the native heart valve. As a result of the difficulties in engineering a perfect prosthetic heart valve, there has been growing interest in repairing a patient's native valve. These efforts have documented equal long-term durability to the use of mechanical prostheses, with added benefits of better ventricular performance due to preservation of the subvalvular mechanism and obviation of the need for chronic anticoagulation. Mitral valve repair has become one of the most rapidly growing areas in adult cardiac surgery today.

Mitral valve disease can be subdivided into intrinsic valve disturbances and pathology extrinsic to the mitral valve ultimately affecting valvular function. Although these subdivisions exist, many of the repair techniques for and overall operative approaches to the various pathologies are similar.

Historically, most valvular pathology was secondary to rheumatic heart disease, a result of a streptococcal infection, most commonly affecting the mitral valve, followed by the aortic valve, and least often the pulmonic valve. The results of the infectious process are mitral stenosis and aortic stenosis, followed by mitral insufficiency and aortic insufficiency. With the advent of better antibiotic therapies, the incidence of rheumatic heart disease is on the decline, and accounts for a smaller percentage of valvular heart conditions in the developed world of the present day. Commissurotomy of rheumatic mitral stenosis was an early example of commonly practiced mitral valve repair outside of the realm of congenital heart defects. However, the repairs of rheumatic insufficient valves have not met with good results due to the underlying valve pathology and the progression of the disease.

Most mitral valve disease other than rheumatic results in valvular insufficiency that is generally amenable to repair. Chordae rupture is a common cause of mitral insufficiency, resulting in a focal area of regurgitation. Classically, one of the first successful and accepted surgical repairs was for ruptured chordae of the posterior mitral leaflet. The technical feasibility of this repair, its reproducible good results, and its long-term durability led the pioneer surgeons in the field of mitral valve repair to attempt repairs of other valve pathologies.

Mitral valve prolapse is a fairly common condition that leads over time to valvular insufficiency. In this disease, the plane of coaptation of the anterior and posterior leaflets is "atrialized" relative to a normal valve. This problem may readily be repaired by restoring the plane of coaptation into the ventricle.

The papillary muscles within the left ventricle support the mitral valve and aid in its function. Papillary muscle dysfunction, whether due to infraction or ischemia from coronary artery disease, often leads to mitral insufficiency (commonly referred to as ischemic mitral insufficiency). Within the scope of mitral valve disease, this is the most rapidly growing area for valve repair. Historically, only patients with severe mitral insufficiency had their mitral valve repaired or replaced, but there is increasing support in the surgical literature to support valve repair in patients with moderate insufficiency that is attributable to ischemic mitral insufficiency. Early aggressive valve repair in this patient population has been shown to increase survival and improve long-term ventricular function.

In addition, in patients with dilated cardiomyopathy the etiology of mitral insufficiency is the lack of coaptation of the valve leaflets from a dilated ventricle. The resultant regurgitation is due to lack of coaptation of the leaflets. There is a growing trend to repair these valves, thereby repairing the insufficiency and restoring ventricular geometry, and thus improving overall ventricular function.

The two essential features of mitral valve repair are to fix primary valvular pathology (if present) and to support the annulus or reduce the annular dimension using an implantable device that is commonly in the form of a ring or band. The problem encountered in mitral valve repair is the surgeon's inability to fully assess the effectiveness of the repair until the heart has been fully closed, and the patient is weaned off cardiopulmonary bypass. Once this has been achieved, valvular function can be assessed in the operating room using transesophageal echocardiography (TEE). If significant residual valvular insufficiency is then documented, the surgeon must re-arrest the heart, re-open the heart, and then repair or replace the valve. This increases overall operative, anesthesia, and bypass times, and therefore increases the overall operative risks.

If the implant used to reduce the annulus is larger than the ideal size, mitral insufficiency may persist. If the implant is too small, mitral stenosis may result. The need exists, therefore, for an adjustable implant that would allow a surgeon to adjust the annular dimension in situ in a beating heart under the guidance of TEE or another diagnostic modality to achieve optimal valvular sufficiency and function.

Cardiac surgery is but one example of a setting in which adjustment of the annular dimension of an anatomic orifice in situ would be desirable. Another example is in the field of gastrointestinal surgery, where the Nissen fundoplication procedure has long been used to narrow the gastro-esophageal junction for relief of gastric reflux into the esophagus. In this setting, a surgeon is conventionally faced with the tension between creating sufficient narrowing to achieve reflux control, and avoiding excessive narrowing that may interfere with the passage of nutrient contents from the esophagus into the stomach. "Gas bloat," which causes the inability to belch, is also a common complication of over-narrowing of the gastro-esophageal junction. Again, it would be desirable to have a method and apparatus by which the extent to which the gastro-esophageal junction is narrowed could be adjusted in situ to achieve optimal balance between those two competing interests.

Another example of a surgical procedure in need of improvement for narrowing an anatomic space is that for gastric bypass used in obesity control. In such a procedure, the goal is to reduce the available stomach volume adjacent to the esophagus in order to earlier stimulate satiation signaling with less food consumption. Prior art technologies include externally suturing or stapling a line of opposing stomach walls together to form a pouch in the upper stomach. This surgical strategy has the disadvantage of requiring invasive surgery to access the exterior of the stomach, and both sides thereof in the case of stapling with a required anvil, in addition to the lack of post operative adjustability of the pouch size. Alternative prior art gastric bypass attempts include encircling the stomach with an inflatable lap band, or Angel Chick prosthesis ring, to compress the stomach into smaller compartments. These techniques are disadvantageous again due to the surgically invasive procedure for applying the bands externally to the stomach, in addition to the high incidence of necrosis as the result of constricting the tissues.

Aside from the problem of adjusting the internal circumference of body passages in situ, there is often a need in medicine and surgery to place an implantable device at a desired recipient anatomic site. For example, existing methods proposed for percutaneous mitral repair include approaches through either the coronary sinus or percutaneous attempts to affix the anterior mitral leaflet to the posterior mitral leaflet. Significant clinical and logistical problems attend both of these existing technologies. In the case of the coronary sinus procedures, percutaneous access to the coronary sinus is technically difficult and time consuming to achieve, with procedures which may require several hours to properly access the coronary sinus. Moreover, many of these procedures employ incomplete annular rings, which compromise their physiologic effect. Moreover, the coronary sinus approach does not address the correction of diseased annular tissues, particularly on the posterior annulus of the mitral valve. Such procedures are typically not effective for improving mitral regurgitation by more than one clinical grade. Finally, coronary sinus procedures carry the potentially disastrous risks of either fatal tears or catastrophic thrombosis of the coronary sinus.

Similarly, percutaneous procedures which employ sutures, clips, or other devices to affix the anterior mitral leaflets to the posterior mitral leaflets also have limited reparative capabilities. Such procedures are also typically ineffective in providing a complete repair of mitral regurgitation. These procedures also fail to address the pathophysiology of the dilated mitral annulus in ischemic heart disease. As a result of the residual anatomic pathology, no annular repair, ventricular remodeling or improved ventricular function is likely with these procedures.

The need exists, therefore, for a delivery system and methods for its use that would avoid the need for open surgery in such exemplary circumstances, and allow delivery, placement, and adjustment of a prosthetic implant to reduce the diameter of a such an annulus in a percutaneous or other minimally invasive procedure, while still achieving clinical and physiologic results that are at least the equivalent of the yields of the best open surgical procedures for these same problems. Further, the need exists for a system that allows remote attachment of such an implant to the desired anatomic recipient site in a percutaneous or other minimally invasive procedure.

The need exists for implant delivery systems and methods which permit improved certainty of correct placement location thereof by visual and/or physical sensations of the operator. There exists a need for improved delivery systems which permit reshaping of the annular tissue to match the delivery configuration of the implant and insure consistent contact therewith for proper attachment. Furthermore, there exists a need to provide a minimally invasive delivery system for attaching an implant to adjacent tissues without manual placement of sutures or staples requiring opposing forces against the target tissues.

As mentioned, the preceding cardiac applications are only examples in which such a delivery system is desirable. Another exemplary application is in the field of gastrointestinal surgery, where the aforementioned Nissen fundoplication procedure has long been used to narrow the gastro-esophageal junction for relief of gastric reflux into the esophagus. Gastric bypass surgery for treatment of moribund obesity is another field in need of improvement. There are many other potential applications in the broad fields of medicine and surgery. Among the other potential applications anticipated are adjustable implants for use in the treatment of urinary incontinence, anastomotic strictures, arterial stenosis, cervical incompetence, ductal strictures, and anal incontinence.

SUMMARY OF THE INVENTION

Devices and methods for delivering and securing an annular implant to control the internal circumference or shape of an annulus are provided by the present invention. The invention also provides devices and methods which permit improved certainty of preferred tissue placement location thereof by providing visual and/or physical information to the operator. The invention provides devices and methods which remove unintended tissues from the site of implantation attachment during delivery. The invention provides devices and methods which permit reshaping of the annular tissue to match the delivery configuration of the implant and insure more consistent contact therewith for proper attachment to the implant. Furthermore, the invention provides devices and methods which provide a minimally invasive delivery system for attaching an implant to adjacent tissues without sutures requiring additional remote manual access or staples requiring opposing forces against the target tissues. These and many other advantages and features of the invention will become apparent to those skilled in the art upon reading the present specification of the preferred embodiments.

In one aspect, the device of the present invention provides an annular implant having an adjustable dimension, such as the circumference of the annular implant. One embodiment of the delivery device of the present invention provides a plurality of movable elongated deployment members, each having a proximal end and a distal end and an annular implant deployment region therebetween releasably disposable within the annulus of the implant. In endoscopic situations where greater flexibility is desired, additional flexible joints can be interspersed along each of the deployment members. The annular implant is disposed about the deployment region of the deployment members in an approximately perpendicular planar relationship with respect to the elongated members. During implantation, which is described in greater detail below, the deployment region is removably disposed within the annulus of implant. The distal ends of the deployment members can be joined by a distal joining member. The deployment members are retractably expandable to an expanded configuration and incrementally contractable to a collapsed configuration, and the implant deployment regions of the deployment members are substantially parallel in an expanded configuration and in a collapsed configuration. Parallel configuration of the deployment regions of the members assists in proper placement of the surrounding implant within a desired tissue site, as discussed below in more detail. such that the implant deployment regions of the deployment members are substantially parallel in at least an expanded configuration.

In a preferred embodiment, the annular implant has an adjustment mechanism which is in communication with an elongated adjustment tool, which has a proximal end and a distal end releasably attached to the adjustment mechanism. The implant can be thereby adjusted in several different aspects, including adjustments of the circumference, the shape and/or planar orientation. The annular implant can be incrementally adjusted through a variety of known mechanisms, such as but not limited to interlocking gears, and gaseous or liquid inflation. For example, an expansive adjustment from a first smaller circumference to a second larger circumference causes the deployment members to expand from an insertion position through a range of motion to a delivery position. In one embodiment, the adjustment tool is re-attachable to the adjustment mechanism after release. Therefore, in one preferred embodiment, the annular implant itself is adjustable before, during, and after implantation, and is carried upon a delivery device which is substantially passive with respect to adjustment of the implant, such as circumferential expansion, shape and/or planar orientation. In another preferred embodiment, the delivery device itself provides active expansion, contraction, and orientation adjustments in addition to those provided by the adjustment mechanism on the annular implant.

In a preferred embodiment of the minimally invasive device, the delivery device further comprises at least one elongated barrel, which has a proximal end and a distal end. Each barrel is movably affixed adjacent its distal end to the deployment region of a deployment member. Each barrel contains at least one attachment element within a distal portion of the barrel for attaching the annular implant to annular tissue. This aspect of the invention eliminates problems in the prior art associated with manual access for suture placement, and tissue damage caused by opposing forces of stapling. The attachment element is fittingly situated within the barrel to guide the attachment element in a predetermined orientation with respect to the barrel. In one embodiment, the barrel has an internal surface configured to guide the attachment element in a predetermined orientation. In one embodiment, the attachment element is made of a shape memory alloy. In a preferred embodiment, the shape memory alloy is nitinol.

The barrel also contains an elongated attachment element release member that corresponds to the attachment element, and the attachment element is deployed from the distal end of the barrel by manipulating the attachment element release member. In one embodiment, the barrels have an elongated cut-out designed to allow a proximal portion of the attachment element to exit the barrel before the proximal end of the attachment element reaches the distal end of the barrel.

In another aspect, a method is provided for delivering and securing an annular implant to an annulus. The method includes inserting the delivery device into a patient's body, delivering the annular implant to the desired annulus of implant, and adjusting the size or shape of the deployment members from a first size or shape to a second size or shape to match the annulus to the size and shape of the annular implant. The method further comprises securing the implant to annular tissue and releasing the implant from the delivery device and withdrawing the delivery device from the patient's body.

In another aspect, an alternative method is provided for delivering and securing an annular implant to an annulus. The method includes delivering the annular implant to the desired annulus of implant and manipulating the attachment element release member(s) to deploy attachment elements into the annular implant and annular tissue. The method further includes securing the implant to annular tissue, then releasing the implant from the delivery device and withdrawing the delivery device from the patient's body.

In another aspect, a device is provided for delivering an annular implant, which comprises an annular implant having an adjustable dimension. The annular implant comprises an adjustment mechanism in connection with an elongated adjustment tool, which has a proximal end and a distal end releasably attached to the adjustment mechanism. The size or shape of the annular implant is incrementally adjusted using the adjustment tool. The device further comprises a spreading mechanism releasably disposable within the annular implant. The spreading mechanism is expandable to conform to the size and shape of the annular implant, and delivery of the annular implant on the spreading mechanism reshapes the annulus to conform to the size and shape of the implant.

In another aspect, a device is provided for delivering and attaching an annular implant, which comprises an annular implant having an adjustable dimension, a spreading mechanism releasably disposable within the annular implant, a plurality of barrels each with a proximal end and a distal end, and a control interface. The proximal end of each barrel is attached to a corresponding location on the control interface, and the distal end of each barrel is releasably attached to the annular implant. The spreading mechanism exerts an expanding force on the annular implant, and the extent of expansion of the spreading mechanism is limited by the size or shape of the annular implant. The control interface allows the annular implant to be advanced with the barrels and oriented independent of the spreading mechanism. In one embodiment, the control interface comprises a controller for adjusting the size or shape of the annular implant. The control interface may also comprise a display which shows a measurement corresponding to the size or shape of the annular implant.

In another aspect, a method is provided for delivering an annular implant to an annulus. The method includes inserting the delivery device into a patient's body, advancing the annular implant and barrels into the patient's left atrium using the control interface, orienting the annular implant as desired using the control interface, advancing the spreading mechanism through the implant using the control interface, and advancing the spreading mechanism and implant to the desired annulus of implant using the control interface.

BRIEF DESCRIPTION OF THE DRAWINGS

The objects and advantages of the present invention will be better understood and more readily apparent when considered in conjunction with the following detailed description and accompanying drawings which illustrate, by way of example, a preferred embodiment and in which:

FIG. 1A is a schematic view showing the embodiment in an expanded configuration. FIG. 1B is a schematic view showing the embodiment in the partially collapsed configuration. FIG. 1C is a schematic view showing the embodiment in a collapsed configuration.

FIG. 9A shows the barrel element before the attachment element release member has been engaged. FIG. 9B shows the barrel element after the attachment element release member has been engaged and the attachment element has entered the annular implant. FIG. 9C shows the barrel element after the attachment element has entered the annular implant and annular tissue. FIG. 9D shows the barrel element after the attachment element has fully exited the barrel and is securing the annular implant to the annular tissue.

FIG. 12A shows the anchoring element in the annular implant before its release has begun. FIG. 12B shows the anchoring element being deformed in the annular implant. FIG. 12C shows the anchoring element after it has been deformed and is releasing from the annular implant. FIG. 12D shows the anchoring element after it has fully released from the annular implant.

FIG. 15A is a schematic view of an embodiment with six deployment members, shown in an expanded configuration. FIG. 15B is a schematic view of an embodiment with six deployment members, shown in the partially collapsed configuration. FIG. 15C is a schematic view of an embodiment with six deployment members, shown in a collapsed configuration.

FIG. 16A is a perspective view showing the embodiment in an expanded configuration. FIG. 16B is a perspective view showing the deployment members advancing along the barrels and through the implant. FIG. 16C is a perspective view showing the embodiment in a partially expanded configuration.

FIGS. 26A-E are a series of views showing various embodiments of the barrel element of the annular implant delivery device of FIG. 16, and FIGS. 26F-H are a series of perspective views showing the operation of one embodiment of the barrel element. FIG. 26A is a cross-sectional side view showing an embodiment of the barrel element with two radially adjacent slots, one containing an attachment element and the other containing an anchoring element. FIG. 26B is a cross sectional side view showing an embodiment of the barrel element with three circumferentially adjacent slots, one containing an attachment element and the other two containing anchoring elements. FIG. 26C is a perspective view showing the embodiment of FIG. 26C. FIG. 26D is a cross-sectional side view showing an embodiment of the barrel element including the same slot configuration as the barrel of FIG. 26B, with an elongated groove. FIG. 26E is a perspective view showing the barrel embodiment of FIG. 26D. FIG. 26F is a schematic view showing the advancement of an attachment element from the barrel embodiment of FIG. 26D. FIG. 26G is a schematic view showing one embodiment of an attachment element exiting from the barrel embodiment of FIG. 26D.

FIG. 27 is a schematic view showing the annular implant delivery device of FIG. 16. The deployment members are anatomically positioned in the left atrium of a heart and being retracted back into the sheath. The annular implant and adjustment tool remain in place at the mitral annulus.

FIG. 28 is a schematic view showing the annular implant delivery device of FIG. 16. The deployment members and barrels have been retracted back into the sheath. The annular implant and adjustment tool remain in place at the mitral annulus.

FIG. 29A is a schematic view showing an embodiment of an annular implant delivery device anatomically positioned in the lower esophagus approaching the gastro-esophageal junction, with the device in a collapsed configuration. FIG. 29B is a schematic view showing an embodiment of an annular implant delivery device anatomically positioned in the lower esophagus approaching the gastro-esophageal junction, with the device in an expanded configuration. FIG. 29C is a schematic view showing an annular implant anatomically positioned in the gastro-esophageal junction to reduce the circumference of the opening.

FIG. 30A is a schematic view showing one embodiment of an annular implant delivery device anatomically positioned in the stomach, with the device in a collapsed configuration. FIG. 30B is a schematic view showing one embodiment of an annular implant delivery device anatomically positioned in the stomach, with the device in an expanded configuration. FIG. 30C is a schematic view showing one embodiment of an annular implant delivery device anatomically positioned in the stomach to reduce the circumference of the attachment site.

DETAILED DESCRIPTION OF THE PREFERRED EMBODIMENTS

Figure 1A:
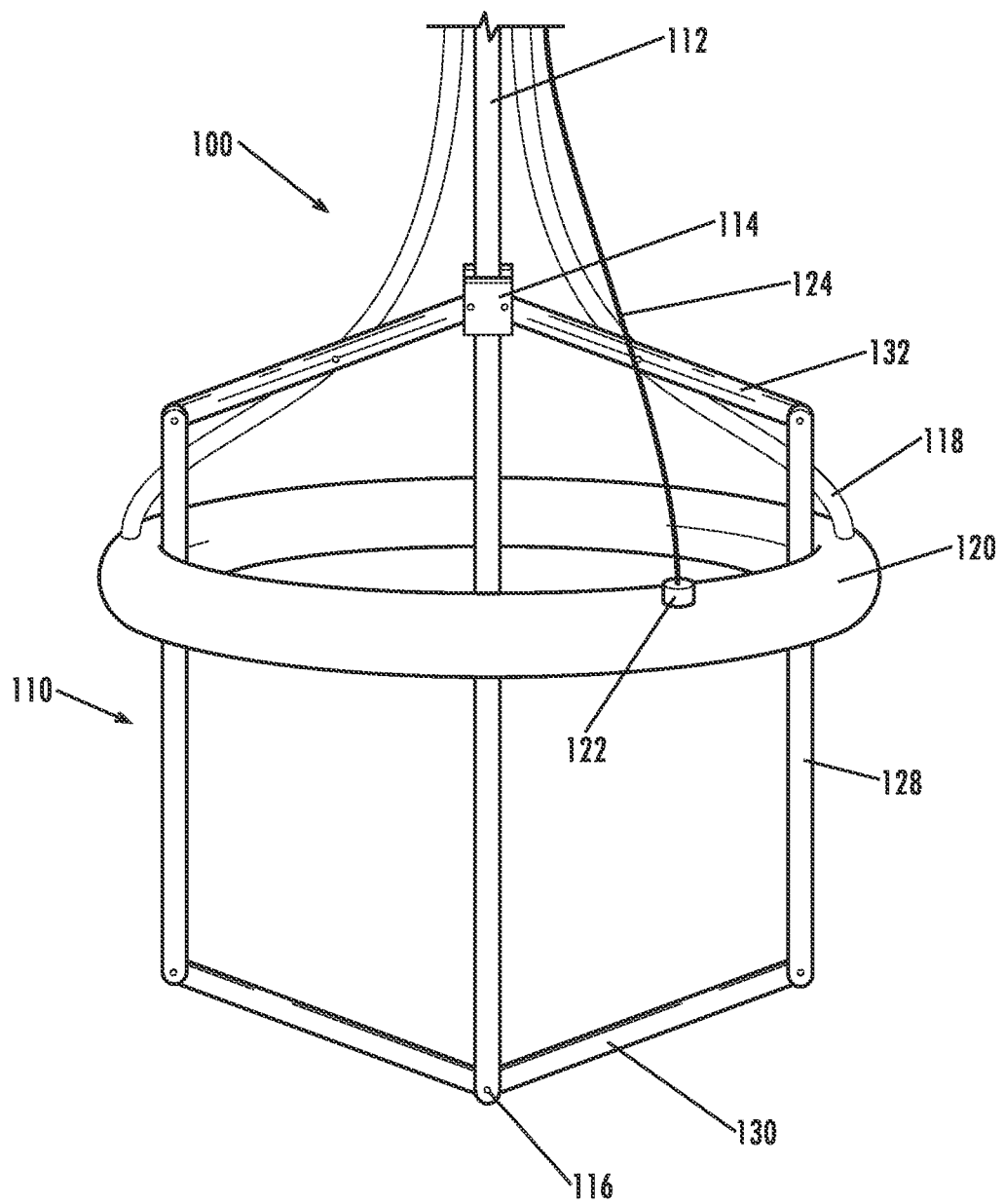
FIGS. 1A-C are a series of schematic views of one embodiment of the annular implant delivery device.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

An improved annular implant delivery device has been developed for use in delivering an annular implant to an annulus in a patient's body. The delivery device can be housed in an endoscopic sheath or trocar or other covering, which is inserted into a patient to deliver an annular implant to an annulus in a minimally invasive procedure. The delivery procedure can be performed endoscopically, percutaneously, or with an endoscope placed within a body cavity or organ, or by trans-abdominal or trans-thoracic approaches. Thus, advantageously, the delivery device can help eliminate the need for an invasive surgical procedure. The delivery device can thereby help reduce the anesthesia and operative times required for a delivery procedure, as well as the risk associated with such a procedure, and the patient pain and recovery time following a procedure.

Devices and methods for delivering and securing an annular implant to control the internal circumference or shape of an annulus are provided by the present invention. The invention also provides devices and methods which permit improved certainty of tissue placement of the implant by providing visual and/or physical information to the operator. The invention provides devices and methods which remove unintended tissues from the site of implantation attachment during delivery. The invention provides devices and methods which permit reshaping of the annular tissue to match the delivery configuration of the implant and insure more consistent contact therewith for proper attachment to the implant. Furthermore, the invention provides devices and methods which provide a minimally invasive delivery system for attaching an implant to adjacent tissues without sutures requiring additional remote manual access or staples requiring opposing forces against the target tissues.

Therefore, the delivery device advantageously provides a means for pushing anatomical structures, such as mitral valves, out of the path of the device as it approaches the annulus, to help avoid damage to tissue around the annulus.

The device also advantageously provides a means of redesigning the size and shape of an annulus during implantation. The delivery device provides a structure for forcing the annulus to conform to the shape and size of the annular implant before securing the implant to the tissue, thereby creating a precise fit. The device further provides a structure for adjusting and maintaining the size and shape of the annulus as desired after the procedure to achieve a desired physiologic effect.

The delivery device also advantageously provides a means of incrementally adjusting the shape or circumference of the annular implant during a beating-heart or "off-pump" procedure, as well as after the procedure once the normal physiologic flow has resumed in situ. The delivery device thereby allows the shape or circumference of the annulus to be affected until the desired physiologic effect has been achieved. Further, the circumference or shape of the annular implant can be adjusted post-operatively, preferably percutaneously, to accommodate changes in the size or physiologic needs of the annulus.

In various embodiments, the delivery device may be employed to deliver an implant to internally adjustably constrict or expand the circumference or other dimensions of an annulus in which a disease process tends to enlarge such circumference or other dimensions. In additional various embodiments, the delivery device may be employed to deliver an implant to adjustably enlarge or maintain the circumference or other dimensions of an annulus in which a disease process tends to narrow or constrict such circumference or other dimensions. As used herein, "annulus" includes any substantially ring-like valve, sphincter, lumen, orifice, or other opening in the body. By way of illustration and not by way of limitation, recipient sites include a heart valve, blood vessels, the esophagus near the gastro-esophageal junction, the stomach, the anus, and the cervix.

In one aspect, the device of the present invention provides an annular implant having an adjustable dimension, such as the circumference of the annular implant. One embodiment of the delivery device of the present invention provides a plurality of movable elongated deployment members, each having a proximal end and a distal end and an annular implant deployment region therebetween releasably disposable within the annulus of the implant. The delivery device can also have a distal joining member for joining the distal ends of the deployment members. The deployment members are retractably expandable by an expansion means to an expanded configuration, such that the implant deployment regions of the deployment members are substantially parallel in at least an expanded configuration. Parallel configuration of the deployment regions of the members assists in proper placement of the surrounding implant within a desired tissue site, as discussed below in more detail.

In a preferred embodiment, the annular implant has an adjustment mechanism which is in communication with an elongated adjustment tool, which has a proximal end and a distal end releasably attached to the adjustment mechanism. The implant can be thereby adjusted in several different aspects, including adjustments of the circumference, the shape and/or planar orientation. The annular implant can be incrementally adjusted through a variety of known mechanisms, such as but not limited to interlocking gears, and gaseous or liquid inflation. For example, an expansive adjustment from a first smaller circumference to a second larger circumference causes the deployment members to expand from an insertion position through a range of motion to a delivery position. In one embodiment, the adjustment tool is re-attachable to the adjustment mechanism after release. Therefore, in one preferred embodiment, the annular implant itself is adjustable before, during, and after implantation, and is carried upon a delivery device which is substantially passive with respect to adjustment of the implant, such as circumferential expansion, shape and/or planar orientation. In another preferred embodiment, the delivery device itself provides active expansion, contraction, and orientation adjustments in addition to those provided by the adjustment mechanism on the annular implant.

In a preferred embodiment, the delivery device further comprises an elongated central support member, which has a proximal end and a distal end. A distal portion of the central support member is attached to the distal joining member. The central support member is substantially parallel to the implant deployment regions of the deployment members. In another preferred embodiment, the device further comprises a proximal joining member for joining the proximal ends of the deployment members. The proximal joining member is slidably attached along the central support member. In one embodiment, the proximal joining member is movable distally to expand the deployment members and proximally to contract the deployment members.

In another embodiment, the deployment members are each attached to a biasing member which experts an expanding force, and the deployment members are thereby biased to expand when unsheathed from a delivery trocar. Biased expansion of the deployment members may be limited by the size or shape of the annular implant. Expansion of the deployment members may cause the annulus to conform to the size and shape of the annular implant.

In a preferred embodiment, the device comprises at least three deployment members. The deployment members, in conjunction with the optional distal joining member, provide structural support for the annular implant, and also serve to guide errant tissues, such as a heart valve leaflet, away from the target site of attachment during insertion of the delivery device. In another embodiment, the implant deployment regions of the deployment members are substantially parallel in an expanded configuration to provide an even degree of resistance during insertion of the implant to target tissues. In yet another embodiment, at least a portion of the deployment members comprise a radio-opaque or echo-opaque material for operator visualization of proper placement within an annulus or other target tissue.

In a preferred embodiment of the minimally invasive device, the delivery device further comprises at least one elongated barrel, which has a proximal end and a distal end. Each barrel is movably affixed adjacent its distal end to the deployment region of a deployment member. Each barrel contains at least one attachment element within a distal portion of the barrel for attaching the annular implant to annular tissue. This aspect of the invention eliminates problems in the prior art associated with manual access for suture placement, and tissue damage caused by opposing forces of stapling. The attachment element is fittingly situated within the barrel to guide the attachment element in a predetermined orientation with respect to the barrel. In one embodiment, the barrel has an internal surface configured to guide the attachment element in a predetermined orientation. In one embodiment, the attachment element is made of a shape memory alloy. In a preferred embodiment, the shape memory alloy is nitinol. In a further embodiment, there are a plurality of attachment elements aligned within the distal portion of each barrel. In another embodiment, the attachment elements comprise a radio-opaque or echo-opaque material on at least a portion thereof, preferably below the annular implant.

The barrel also contains an elongated attachment element release member that corresponds to the attachment element, and the attachment element is deployed from the distal end of the barrel by manipulating the attachment element release member. In one embodiment, the barrels have an elongated cut-out designed to allow a proximal portion of the attachment element to exit the barrel before the proximal end of the attachment element reaches the distal end of the barrel.

In one embodiment, the distal end of each barrel is fixedly attached to the deployment region of a deployment member such that the distal end of each barrel is facing the annular implant when the deployment members are in an expanded configuration. In one embodiment, each barrel is slidably attached to a corresponding deployment member proximal to the deployment region of the deployment member for maintaining the orientation of the distal end of the barrel with respect to the annular implant throughout a range of expansion of the deployment members. In one embodiment, there is more than one barrel affixed to the deployment region of a deployment member to provide multiple points of tissue attachment. In alternative embodiments, the deployment members are slidably attached to respective barrels.

In another embodiment, the delivery device further comprises an anchoring element in connection with each barrel. The barrels may include a plurality of separate slots, with at least one slot containing an attachment element and at least one slot containing an anchoring element. In one embodiment, the anchoring element extends from each barrel into the annular implant, which releasably attaches the annular implant to the barrel. In a further embodiment, the delivery device further comprises an anchoring element which wraps around the annular implant, releasably attaching the annular implant to the barrel. In alternative embodiments, the annular implant is anchored to the barrels by removable sutures or coiled wire elements. The anchoring elements maintain the annular implant on the deployment region of the deployment members. Additionally, the anchoring elements maintain the implant in alignment with the distal ends of the elongated barrels, which provides stabilizing forces for the implant against the barrel during distally advancing delivery motion, and provides hinged alignment forces for the implant against the barrel during expansion of the deployment members and during deployment of the attachment elements. In one embodiment, the anchoring element releases from the annular implant when the annular implant is attached to annular tissue and a force is applied to the barrel in a proximal direction.

In another aspect, a method is provided for delivering and securing an annular implant to an annulus. The method includes delivering the annular implant to the desired annulus of implant and manipulating the attachment element release member(s) to deploy attachment elements into the annular implant and annular tissue. The method further includes securing the implant to annular tissue, then releasing the implant from the delivery device and withdrawing the delivery device from the patient's body.

In another aspect, a device is provided for delivering and attaching an annular implant that delivers the annular implant to a desired annulus of implant and attaches the annular implant to the annulus by deploying at least one memory shape attachment element into the annular implant and annulus. In one embodiment, the deployment members conform the annulus to match the size and shape of the annular implant prior to attaching the annular implant to the annulus.

In another aspect, a device is provided for delivering an annular implant, which comprises an annular implant having an adjustable dimension. The annular implant comprises an adjustment mechanism in connection with an elongated adjustment tool, which has a proximal end and a distal end releasably attached to the adjustment mechanism. The annular implant size or shape is incrementally adjusted using the adjustment tool. The device further comprises a spreading mechanism releasably disposable within the annular implant. The spreading mechanism is expandable to conform to the size and shape of the annular implant, and delivery of the annular implant on the spreading mechanism reshapes the annulus to conform to the size and shape of the implant.

In another aspect, a device is provided for delivering and attaching an annular implant, which comprises an annular implant having an adjustable dimension, a spreading mechanism releasably disposable within the annular implant, a plurality of barrels each with a proximal end and a distal end, and a control interface. The proximal end of each barrel is attached to a corresponding location on the control interface, and the distal end of each barrel is releasably attached to the annular implant. The spreading mechanism exerts an expanding force on the annular implant, and the extent of expansion of the spreading mechanism is limited by the size or shape of the annular implant. The control interface allows the annular implant to be advanced with the barrels and oriented independent of the spreading mechanism. In one embodiment, the control interface comprises a controller for adjusting the size or shape of the annular implant. The control interface may also comprise a display which shows a measurement corresponding to the size or shape of the annular implant.

In another aspect, a method for delivering an annular implant to an annulus. The method includes inserting the delivery device into a patient's body, advancing the annular implant and barrels into the patient's left atrium using the control interface, orienting the annular implant as desired using the control interface, advancing the spreading mechanism through the implant using the control interface, and advancing the spreading mechanism and implant to the desired annulus of implant using the control interface.

In another aspect, a method is provided for delivery of an annular implant. The method includes inserting the delivery device into a patient's body, delivering the annular implant to the desired annulus of implant, and adjusting the size or shape of the annular implant from a first size or shape to a second size or shape to match the annulus to the size and shape of the annular implant. The method further includes securing the implant to annular tissue, then releasing the implant from the delivery device and withdrawing the delivery device from the patient's body.

The annular implant delivery device can be further understood with reference to the exemplary, non-limiting embodiments illustrated in FIGS. 1-30.

Figure 1B:
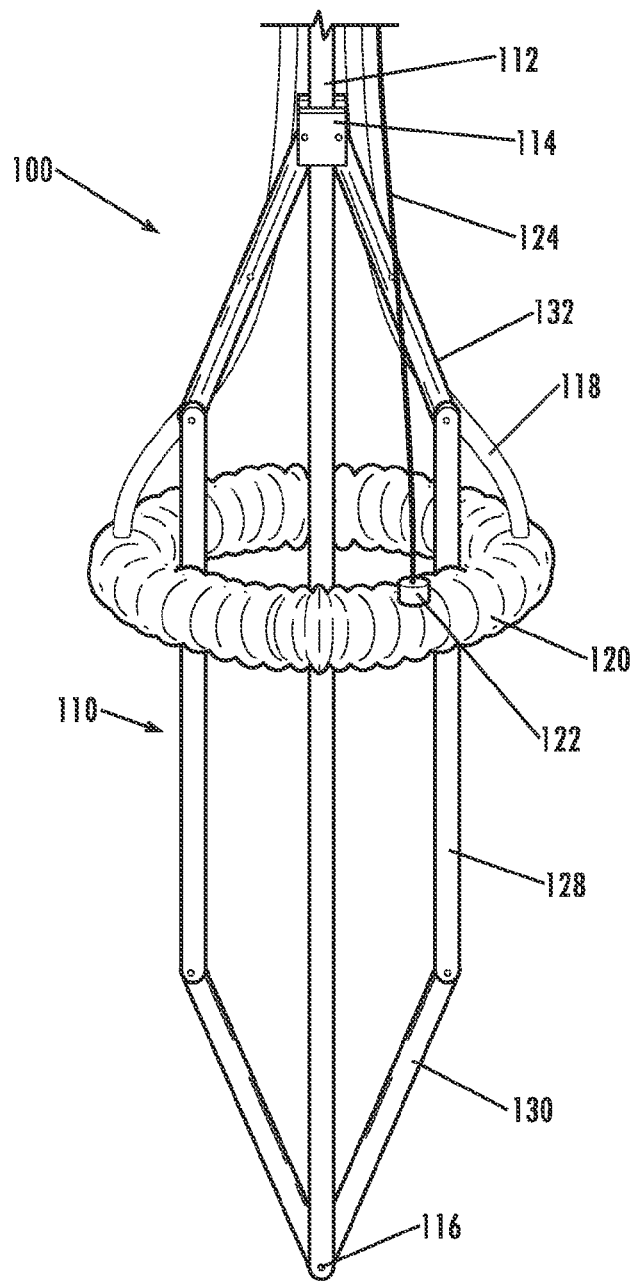
Figure 1C:
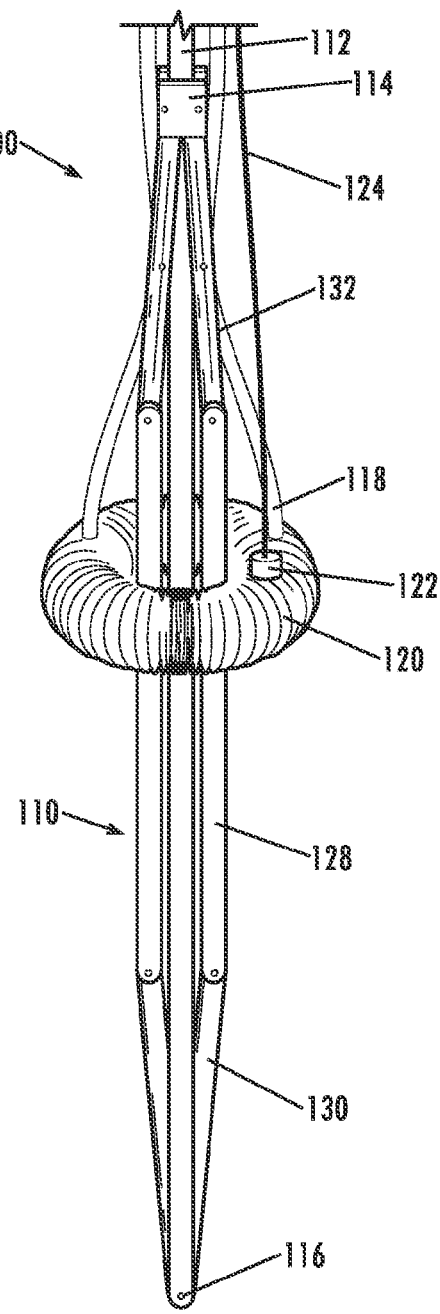

One embodiment of the annular implant delivery device is shown in FIG. 1A in an expanded configuration, in FIG. 1B in a partially collapsed configuration, and in FIG. 1C in a collapsed configuration. The embodiment shown is designed for delivery of an annular implant to the mitral annulus of a heart. In other embodiments, the delivery device is designed for any other annulus within the human body that is creating dysfunction that might be relieved by an implant capable of changing the size and shape of that site and maintaining a desired size and shape after surgery.

The annular implant delivery device 100 shown in FIGS. 1A-C includes deployment members 110, a central support member 112, a proximal joining member 114, a distal joining member 116, and barrels 118, as well as an annular implant 120 with a coupled adjustment mechanism 122 and adjustment tool 124. The number of deployment members 110 can vary. The delivery device 100 is shown to include two deployment members 110 for simplicity, but the device can include several deployment members 110. In preferred embodiments, the device includes three to twelve or more deployment members 110. With an increasing number of deployment members 110, the device is increasingly cylindrical in an expanded configuration, and the cross-sectional shape of the annular implant 120 around the perimeter of the deployment regions 128 of the deployment members 110 tends to approximate a circle. The deployment members 110 may be configured to other similar shapes such as oval, kidney bean or saddle shaped, depending on the desired shape of the recipient annulus.

Deployment members 110 can have a multiplicity of forms. The deployment members 110 may be jointed or non-jointed. In a preferred embodiment, each deployment member 110 contains flexible joints at both ends of the deployment region 128 that allow the angles between contiguous regions of the deployment members 110 to vary, thereby allowing the deployment members 110 to expand and contract. Additional jointed members can be provided to increase flexibility of the device, such as for vascular endoscopic applications. Furthermore, any aspects of the deployment members 110 can be telescopically configured to expand and contract as desired. The deployment members 110 may be a metallic, plastic, synthetic, or any other biologically-compatible material, or combination thereof. In one embodiment, the deployment members 110 are made of titanium.

The deployment members 110 are joined at the proximal joining member 114. The proximal joining member 114 is slidably attached to the central support member 112. The proximal joining member 114 can have a multiplicity of forms. In one embodiment, the proximal joining member 114 is a cuff surrounding the central support member 112. The proximal joining member 114 is connected to a deployment articulation member, such as a wire (not shown) that extends along or within the central support member 112 to a control interface outside the patient's body (not shown). The control interface provides a means of remotely controlling the movement of the proximal joining member 114. Using the control interface, the deployment articulation member can be manipulated to slide the proximal joining member 114 along the central support member 112 toward its proximal end or toward its distal end. Further, the deployment articulation member can be manipulated to cause the proximal joining member 114 to slide incrementally, allowing partial contraction or expansion of the deployment members 110. Moving the proximal joining member 114 proximally causes the deployment members 110 to contract and ultimately to reach a collapsed configuration. Moving the proximal joining member 114 distally causes the deployment members 110 to expand and ultimately to reach an expanded configuration.

The deployment members 110 are also joined at the distal joining member 116. The distal ends of the deployment members 110 themselves may or may not be in contact with each other. The distal joining member 116 is attached to or incorporated within the central support member 112. The distal joining member 116 can have a multiplicity of forms. In one embodiment, the distal joining member 116 is a flexible multi-sided hinge secured in the central support member 112. In another embodiment, the distal joining member is a portion of material, preferably in the shape of a circle, triangle or square, for example, to which each of the deployment members 110 is attached. The distal regions 130 of the deployment members 110 extending from the distal joining member 116 to the start of the deployment regions 128 are angled outward from the distal joining member 116. Preferably, the deployment members 110 are flexibly attached to the distal joining member 116, allowing the angle between the central support member 112 and the distal region 130 of the deployment member 110 to change. The angle is more acute when the delivery device 100 is in a collapsed configuration than when the delivery device 100 is in an expanded configuration. This angled distal region 130 can act as a spreader at the anatomic recipient site, to push anatomical structures out of the path of the device 100 as the implant 120 approaches the annulus. This feature is advantageous for use of the delivery device 100 in mitral valve applications, for example, because the distal region 130 pushes the mitral leaflets apart to ensure safe passage of the device 100 through the mitral valve.

The length of the deployment regions 128 of the deployment members 110 should be selected such that the deployment regions 128 extend through the annulus, such as that supporting the mitral valve. The length of the deployment regions 128 can be adjusted to accommodate a range of types of annuli and a range of annulus sizes. The length of the regions contiguous to the deployment region 128 on each of the distal and proximal sides should be selected such that the width of the device in an expanded configuration approximates the diameter of the target annulus of implant. The length of these contiguous regions can also be adjusted to accommodate a range of types of annuli and a range of annulus sizes.

The portion of the deployment regions 128 of the deployment members 110 distal to the annular implant 120 can be constructed of or labeled with an echo-opaque and/or a radio-opaque material (not shown). Alternatively, the distal aspects of the deployment members 110 can be constructed of thicker or thinner material to contrast with the portions of the deployment members proximal to the annular implant 120. Such distinguishing marking enables a surgeon to visualize the location of the deployment members 110 and correspondingly, the annular implant 120, with respect to the recipient site during the delivery procedure using TEE or other imaging modalities.

The shape and size of the annular implant 120 should be chosen according to the anatomic needs of the intended recipient site. Like the deployment members, the implant may be round or have other similar shapes such as oval, kidney bean or saddle shaped, depending on the desired shape of the recipient annulus. Use of the terms "circumference" and "radius" and modifications thereof does not denote that the referenced structure, in most cases the implant 120, is circular. For non-circular shapes, such as a kidney bean, "circumference" is used to mean the distance around the perimeter of the shape.

The composition of the annular implant 120 should also be chosen according to the needs of the recipient site. The implant 120 can be accordian-like, as shown in FIGS. 1A-C, or it may have a smooth surface. In various embodiments, the annular implant 120 may be a solid structure, a tubular or otherwise hollow structure, or a structure with an outer member and an inner member. In the latter embodiment, the outer member of the implant body may serve as a covering for the implant 120, and may be designed to facilitate and promote tissue ingrowth and biologic integration to the annulus. The outer member in such an embodiment may be fabricated of a biologically compatible material, such as Dacron, PTFE, malleable metals, other biologically compatible materials, or a combination of such biologically compatible materials in a molded, woven, or non-woven configuration. The outer member in such an embodiment also serves to house the inner member. In such an embodiment, the inner member provides an adjustment means that, when operated by an adjustment tool 124, is capable of altering the shape and/or size of the outer member in a defined manner, or vice versa. Further, at least some portions of the adjustable inner or outer member may be elastic to provide an element of variable, artificial muscle tone to a valve, sphincter, orifice or lumen in settings where such variability would be functionally valuable, such as in the treatment of rectal incontinence or vaginal prolapse.

There can be a variety of known mechanisms for adjustment of the annular implant 120, such as the rack and pinion system described in Application No. WO 2004/019816 A3, incorporated by reference herein, or the telescoping system or other systems described in application Ser. No. 11/802,264, also incorporated by reference in its entirety.

During delivery of the annular implant 120, the annular implant 120 is secured to the delivery device 100. In one embodiment, the annular implant 120 is attached to the barrels 118 by anchoring elements 134 (shown in detail in FIGS. 12A-D). An anchoring element 134 is attached to the distal portion of a barrel 118 and extends therefrom into the annular implant 120. The anchoring elements 134 preferably hold the annular implant 120 in contact with the deployment region 128 of each of the deployment members 110. A barrel 118 may have zero, one, or a plurality of anchoring elements 134 attached to it. The distal end of each anchoring element 134 is releasably attached to the annular implant 120 such that the anchoring element 134 releases from the annular implant 120 when the delivery device 100 is retracted following delivery and securing of the annular implant 120 to the annulus, as shown in FIGS. 12A-D. The anchoring elements 134 may be a metallic, plastic, synthetic, or any other biologically-compatible material, or combination thereof. In one embodiment, the anchoring elements 134 are made of a partially deformable plastic.

The annular implant 120 includes an adjustment gear or adjustment mechanism 122 that is in communication with a selectively engageable elongated adjustment tool 124. In alternate embodiments, the adjustment mechanism 122 may be external to or incorporated within the annular implant 120. Further, the adjustment mechanism 122 can have a multiplicity of forms apparent to one skilled in the art. The adjustment tool 124 extends from the adjustment mechanism 122 along the central support member 112 to a control interface outside of the patient's body. Using the control interface, the adjustment tool 124 can be used to adjust the size or shape, including the circumference, of the annular implant 120 from outside the patient's body. The size or shape of the annular implant 120 can be adjusted during the delivery procedure and after the delivery procedure. The adjustment tool 124 can temporarily remain in place, attached to the adjustment mechanism 122 and extending outside the patient's body, following the procedure such that the size or shape of the annular implant 120 can be adjusted after normal physiologic flow has resumed in situ. In one embodiment, the adjustment tool 124 interfaces with the adjustment mechanism 122 in an approximately perpendicular orientation or at least an orientation which is off-plane to the plane defined by the annulus or the implant 120.

In one embodiment, the annular implant 120 delivery device 100 includes at least one barrel 118. The delivery device 100 in FIG. 1 is shown to include two barrels 118, but it can include several barrels 118. As shown, each barrel 118 corresponds to a deployment member 110. However, there can be more than one barrel 118 corresponding to a given deployment member 110. In a preferred embodiment, the number of barrels 118 is equal to the number of deployment members 110, and each barrel 118 corresponds to a different deployment member 110. The invention contemplates that some deployment members 100 may have no barrels 118 associated therewith. The barrels 118 extend along the central support member 112 from the proximal end of the central support member 112 to a point proximal to the proximal joining member 114. The barrels 118 then extend away from the central support member 112 and each cross their corresponding deployment member 110 at a location on the proximal region 132 of the deployment member 110. The barrel 118 can be attached to the proximal region 132 of the corresponding deployment member 110. In certain embodiments, the barrel 118 is slidably attached to the proximal region 132 of the corresponding deployment member 110, or vice versa, such that the location of crossing can change when the deployment members 110 are expanded and contracted. In another embodiment, the barrels 118 are fixedly attached to the proximal region 132 of the corresponding deployment member 110 at the location of crossing. The barrel 118 may be attached to the proximal region 132 using any fastening means, including an adhesive, one or more screws, or one or more pins. In another embodiment, the barrels 118 are not attached to the proximal region 132 of the corresponding deployment member 110.

The distal portion of each barrel 118 is attached to the deployment region 128 of the corresponding deployment member 110. The distal portion of the barrel 118 may be attached such that the distal end of the barrel 118 is limited in its range of movement with respect to the deployment region 128 of the deployment member 110. The barrel 118 may be attached to the deployment region 128 using any fastening means, including an adhesive, one or more screws, or one or more pins. Preferably, the distal end of each barrel 118 remains in substantial contact with the annular implant 120 throughout the range of deployment member 110 expansion and contraction.

Figure 11A:
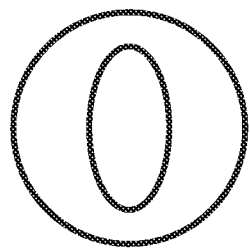
FIGS. 11A-F are cross-sectional views of various embodiments of the lumen of the barrel element shown in FIGS. 9A-D.
Figure 11B:
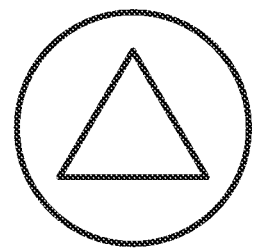
Figure 11C:
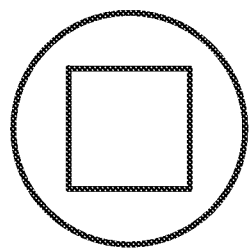
Figure 11D:
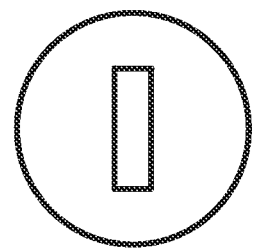
Figure 11E:
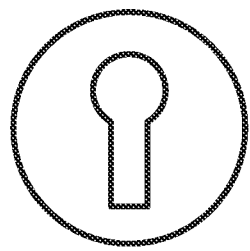
Figure 11F:
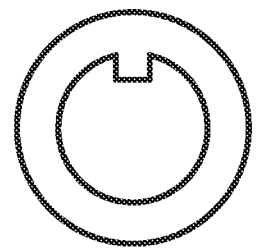

The distal portion of each barrel 118 contains at least one attachment element 136 (shown in detail in FIGS. 9A-D). The attachment element 136 is fittingly situated within the barrel 118 such that it is maintained in a desired orientation with respect to the barrel 118. The lumen of the barrel 118 can have a variety of configurations which keep the attachment element 136 fittingly situated. In various embodiments, the lumen of the barrel 118 has the shape of an oval, as shown in FIG. 11A; a triangle, as shown in FIG. 11B; a square, as shown in FIG. 11C, a rectangle, as shown in FIG. 11D, a keyhole, as shown in FIG. 11E, or an inverted keyhole, as shown in FIG. 11F, in order to maintain the orientation of the attachment element 136.

The location of the distal end of the barrel 118 with respect to the annular implant 120, which is controlled by the point of attachment of the barrel 118 to the deployment region 128, determines the location at which the attachment element 136 penetrates the annular implant 120. If there is more than one barrel 118 corresponding to a given deployment member 110, the location of attachment of the distal portions of the barrels 118 to the deployment region 128 should be selected to deliver the attachment elements 136 to the annular implant 120 at varying locations. Depending upon the desired points of attachment of the implant 120 to adjacent tissue, the distal ends of the barrels 118 may be oriented at different angles. For example, for mitral valve annular repair, the annular implant 120 is generally attached to the upper or atrial surface of the annulus and the barrels would be generally angled downward to project attachment elements 136 distally through the implant 120 and into the tissue. For gastric bypass procedures, however, the attachment points may be lateral to the annular implant 120, and the barrels 118 would be generally angled outwardly to project the attachment elements 136 laterally through the implant and into the adjacent tissue.

Figure 10A:
FIGS. 10A-H are perspective views of various embodiments of the attachment element shown in FIGS. 9A-D.
Figure 10B:
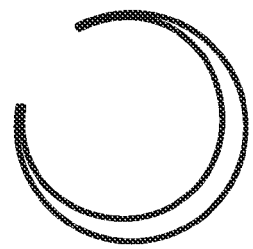
Figure 10C:
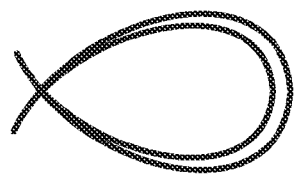
Figure 10D:
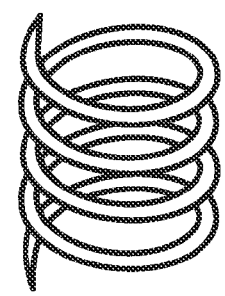
Figure 10E:
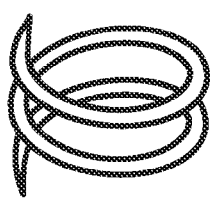
Figure 10F:
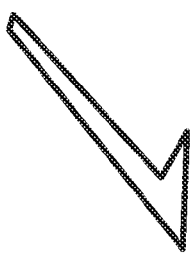
Figure 10G:
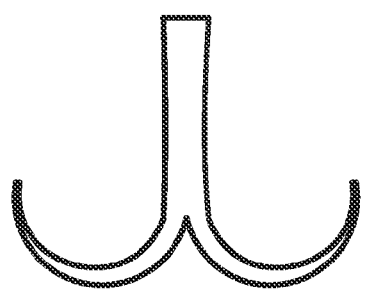
Figure 10H:
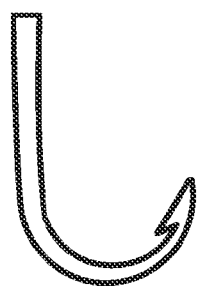

Attachment elements 136 can have a multiplicity of forms. The attachment elements 136 may be a metallic, plastic, synthetic, or any other biologically-compatible material, or combination thereof. In one embodiment, the attachment element 136 is made of a shape memory alloy. In a preferred embodiment, the shape memory alloy is nitinol. The configuration of the attachment element 136 can also vary. Examples of various embodiments of the attachment element 136 are shown in FIGS. 10A-H. The attachment element 136 in its relaxed position can be in the shape of a curve, as shown in FIG. 10A; a loop, as shown in FIG. 10B; a coil, as shown in FIG. 10C; a multi-coiled spiral, as shown in FIG. 10D; a two-coiled spiral, as shown in FIG. 10E; a rod with a barb, as shown in FIG. 10F; a bifurcated rod, as shown in FIG. 10G; or an anchor, as shown in FIG. 10H. The attachment element 136 can also be a pin or screw. In some embodiments, the attachment element 136 penetrates only tissue. In other embodiments, the attachment element 136 penetrates both tissue and an implantable device, and the order of penetration can vary.

Figure 2:
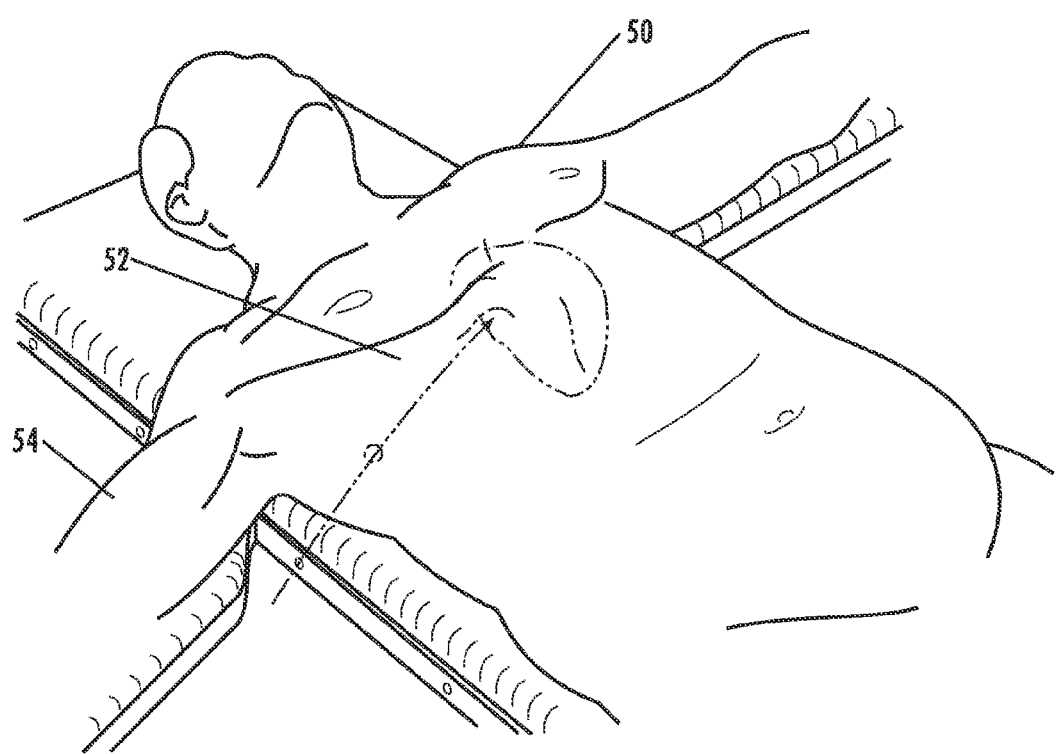
FIG. 2 is a schematic view of a patient in the supine position preparing for implantation of an annular device.

FIG. 2 shows a patient 50 in supine position preparing to undergo a minimally invasive procedure for mitral valve repair provided by one embodiment of the device of the present invention. The right lateral aspect of the patient's chest 52 is exposed by raising the right arm 54. The patient 50 has been sedated, anesthetized and intubated for surgery. The right lung has been deflated. An initial incision between the ribs is made for insertion of an endoscopic camera for viewing of the pericardium. Additional incisions are made for insertion of forceps and scissors for the removal of a portion of the pericardium. A purse string stitch is made in the left atrial wall, and an incision is made into the atrial wall of the heart while tensioning the purse string with a Ramel. A housing sheath, such as a trocar, is then advanced through the atrial wall incision while sufficiently loosening and then re-tightening the Ramel.

Figure 3:
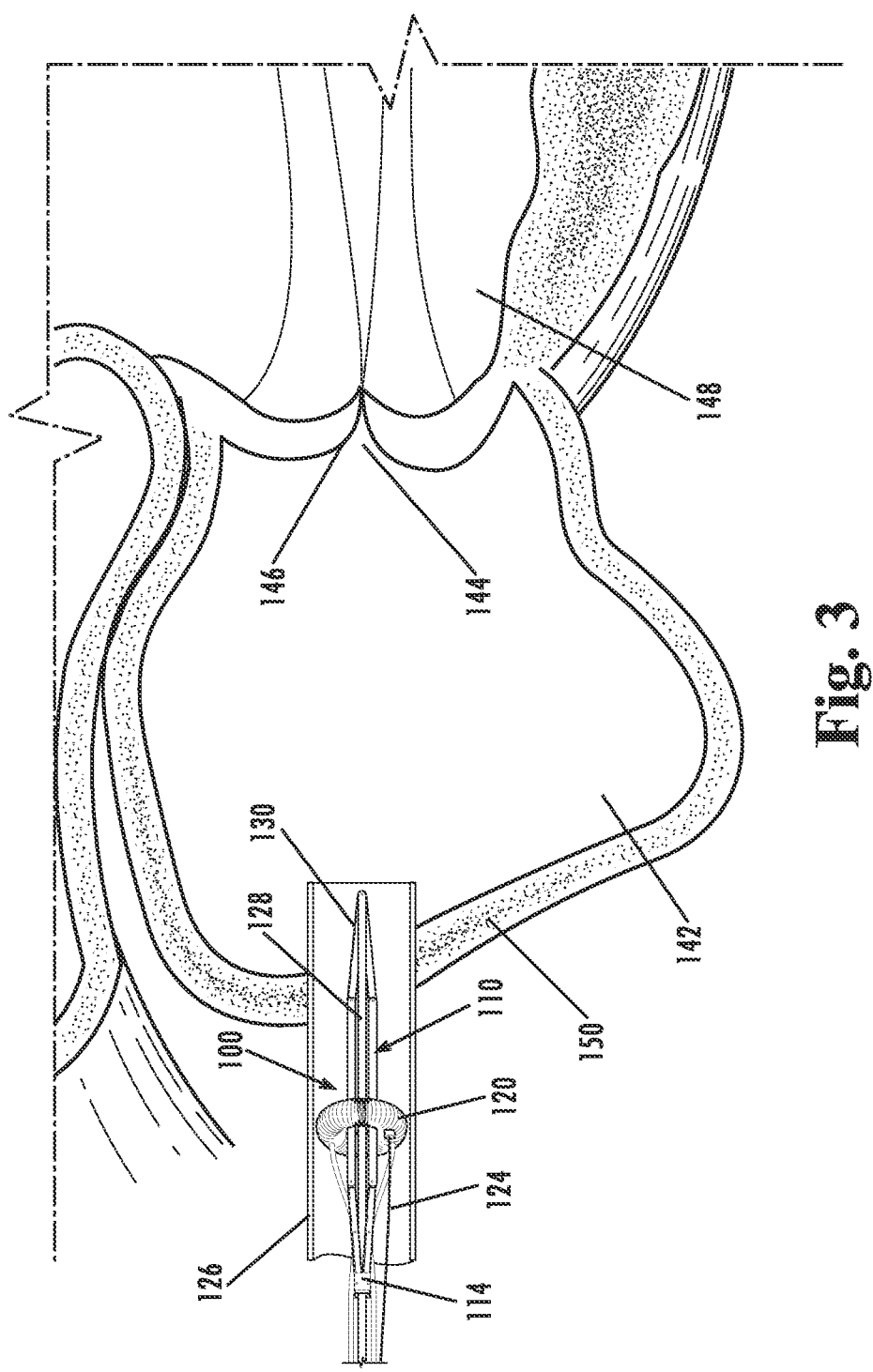
FIG. 3 is a schematic view showing the annular implant delivery device of FIG. 1 anatomically positioned in a wall of the left atrium of a heart with the device in a collapsed configuration inside a sheath.
Figure 4:
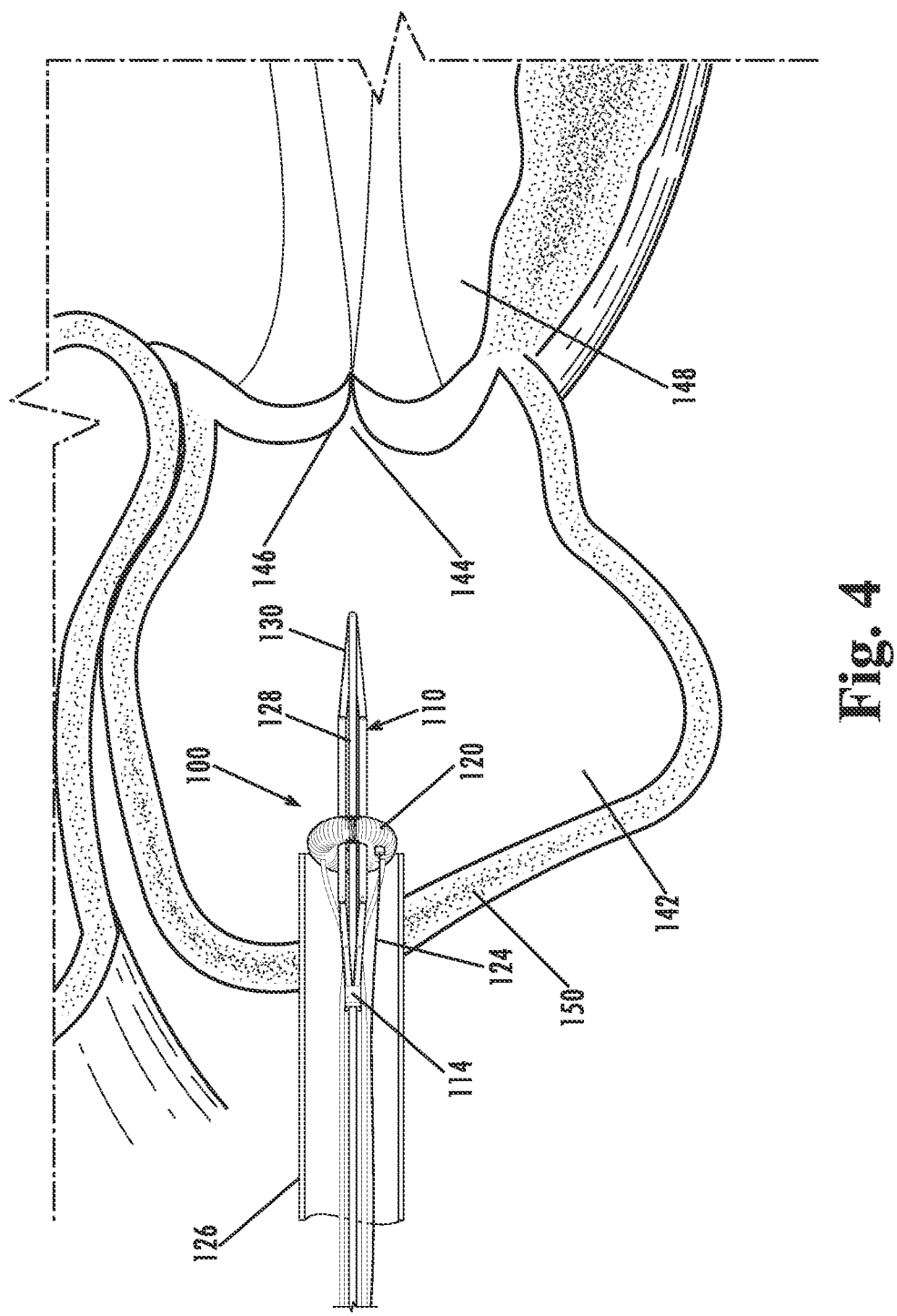
FIG. 4 is a schematic view showing the annular implant delivery device of FIG. 1 anatomically positioned in the left atrium of a heart and advancing out of the sheath, with the device in a collapsed configuration.

FIGS. 3-8 depict a sequence of the delivery and implantation of an annular implant in the mitral annulus of a heart using one embodiment of the delivery device. FIG. 3 begins the delivery of an annular implant 120 to the mitral annulus of a heart through the trocar or housing sheath 126. FIG. 3 shows the annular implant delivery device 100 anatomically positioned in the wall 150 of the left atrium 142 of a heart, with the delivery device 100 in a collapsed configuration within the housing sheath 126. The delivery device 100 is slidably mounted within the housing sheath 126. The housing sheath 126 is inserted into a patient through an incision in the patient's chest. The sheath 126 is directed into the left atrium 142 of the patient's heart through a myocardial incision in the wall 150 of the left atrium 142. The myocardial incision has been prepared with a Ramel or pursestring tourniquet, as is typical for incisions of this type, to prevent bleeding. Preferably, the sheath 126 is inserted into the patient to a predetermined point, such as by a marking on the outer surface of the sheath 126. The delivery device 100 is then advanced, without moving the sheath 126, as shown in FIG. 4. The delivery device 100 is still in a collapsed configuration. The delivery device 100 is advanced further until the entirety of the deployment members 110 is in the cavity of the left atrium 142. As the device 100 is advanced through the left atrium 142, the device 100 may remain in a collapsed configuration.

Before the delivery device 100 is advanced into contact with the mitral leaflets 146, the surgeon can confirm the position of the mitral leaflets 146 by TEE or other imaging modalities to ensure that they will not be damaged by the passage of the delivery device 100 through the mitral valve 144. Advantageously, the device 100 can be partially expanded before advancing the device 100 into contact with the mitral leaflets 146. By manipulating the deployment articulation member (not shown) from the control interface outside the patient's body, the proximal joining member 114 can be moved distally to partially expand the deployment members 110. Alternatively, the size or shape of the annular implant 120 can be increased using the adjustment tool 124 to passively expand the deployment members 110. Therefore, the device 100 includes multiple means of annular expansion and control. Such partial expansion is appropriate when the mitral leaflets 146 are billowy and need to be pushed toward the left ventricle 148 to ensure safe passage of the device through the mitral valve 144. Even in a collapsed configuration, the distal regions 130 of the deployment members 110 may serve to spread apart the mitral leaflets 146 and create space for the deployment region 128 to enter the mitral valve 144.

The surgeon may also confirm that the deployment regions 128 of the deployment members 110 are substantially perpendicular to the plane of the mitral annulus before advancing the device through the mitral valve 144. The region of each deployment member 110 distal to the annular implant 120 can be labeled with an echo-opaque or radio-opaque material, allowing the surgeon to view the location of the deployment members 110 and implant 120 using TEE or other imaging modalities. The substantially parallel nature of the deployment members 110 is advantageous for positioning and implantation. The deployment members 110 can be used to confirm correct positioning of the device 100—aligned to proceed straight through the mitral valve 144—before they are advanced further or are expanded to open the annulus. Also, advancing the substantially parallel deployment members 110 through the mitral valve 144 prior to the implant 120 can ensure that the implant 120 evenly contacts the intended area of the annulus. The substantially parallel deployment members also assist in evenly shape matching the surrounding, expanded annulus tissue to the shape of the annular implant 120 prior to attachment.

Figure 5:
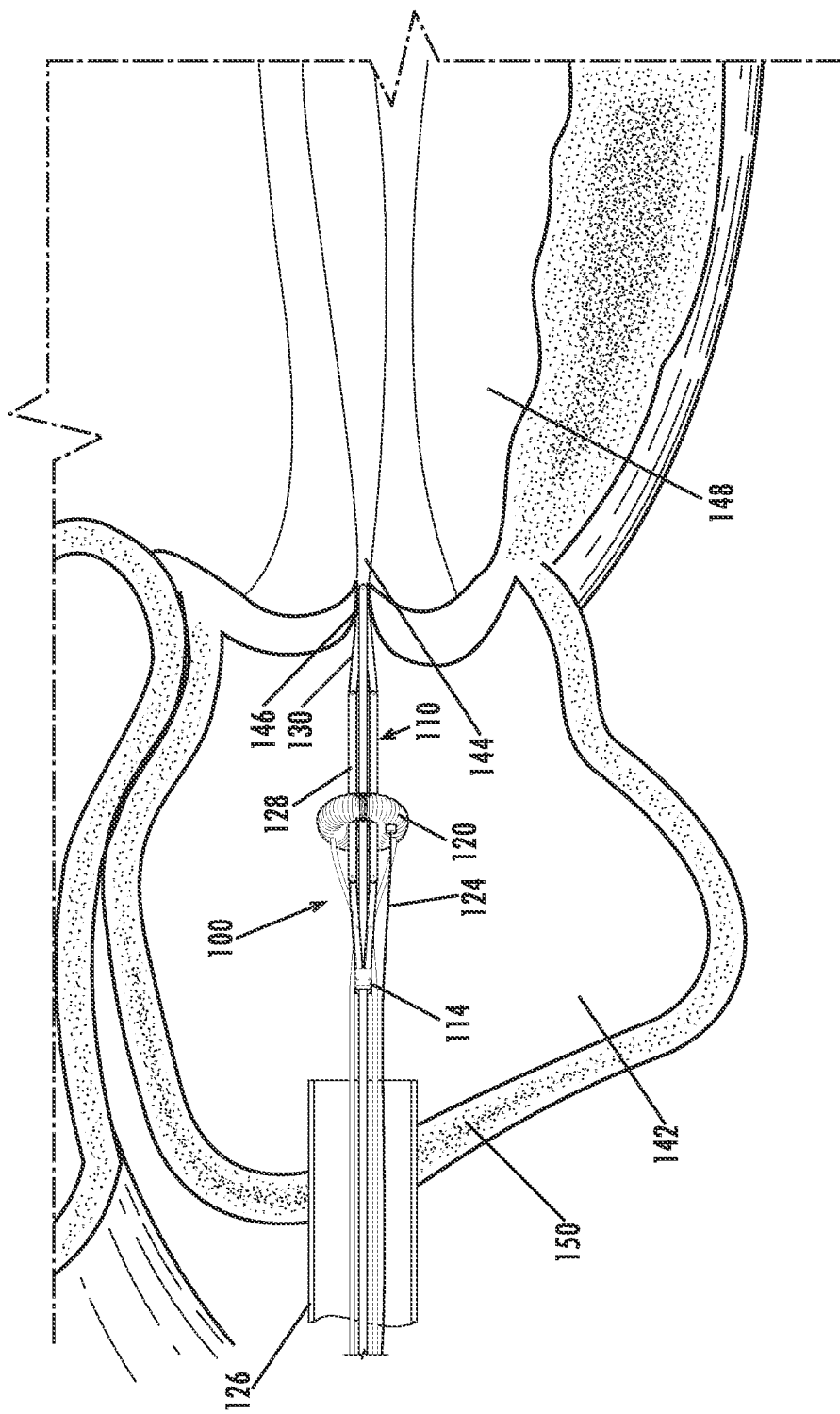
FIG. 5 is a schematic view showing the annular implant delivery device of FIG. 1 anatomically positioned in the left atrium of a heart and approaching the mitral annulus, with the device in a collapsed configuration.
Figure 6A:
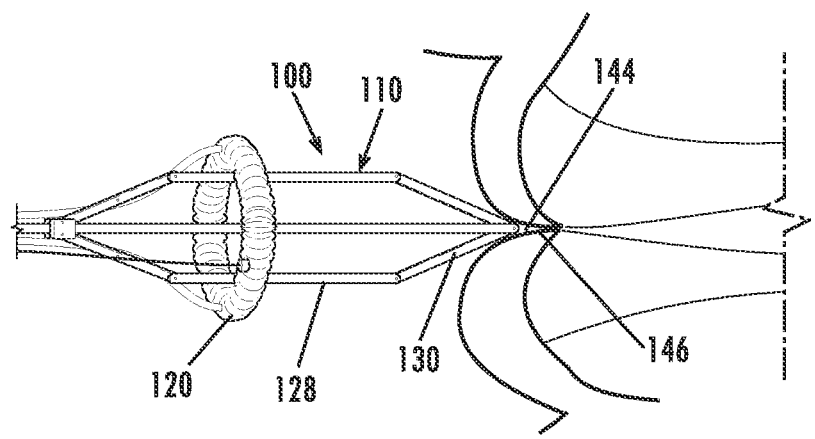
FIGS. 6A-C are a series of schematic views showing the annular implant delivery device of FIG. 1 pushing the mitral leaflets apart and entering the mitral valve.
Figure 6B:
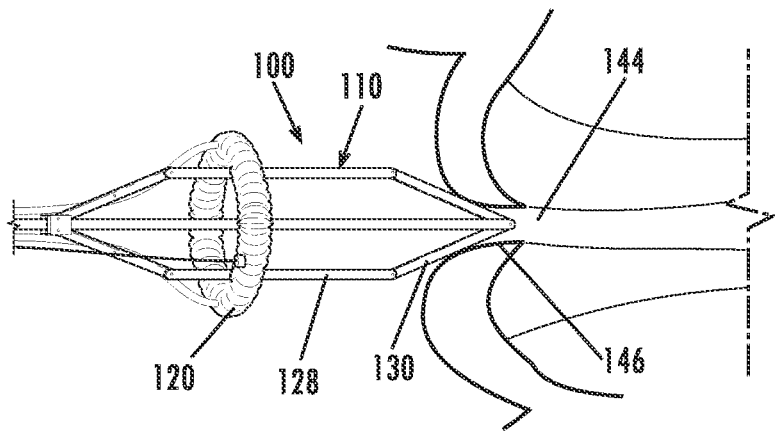
Figure 6C:
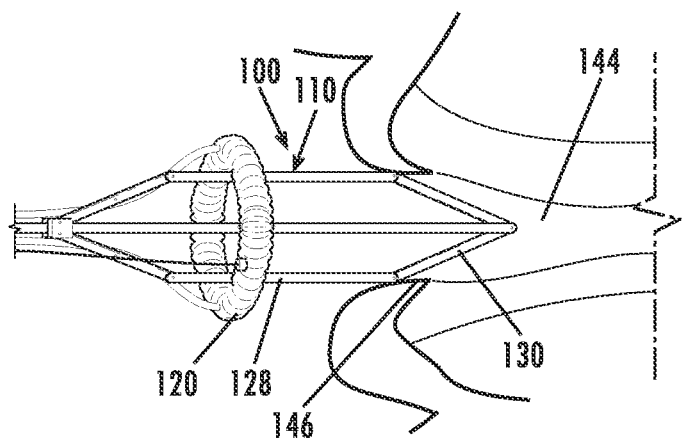

Ultimately, the device 100 is advanced into contact with the mitral leaflets 146, as shown in FIG. 5, and through the mitral valve 144. A sequence of the distal regions 130 of the partially expanded deployment members 110 contacting the mitral leaflets 146 and spreading them apart down and laterally is shown in FIGS. 6A-C.

Figure 7:
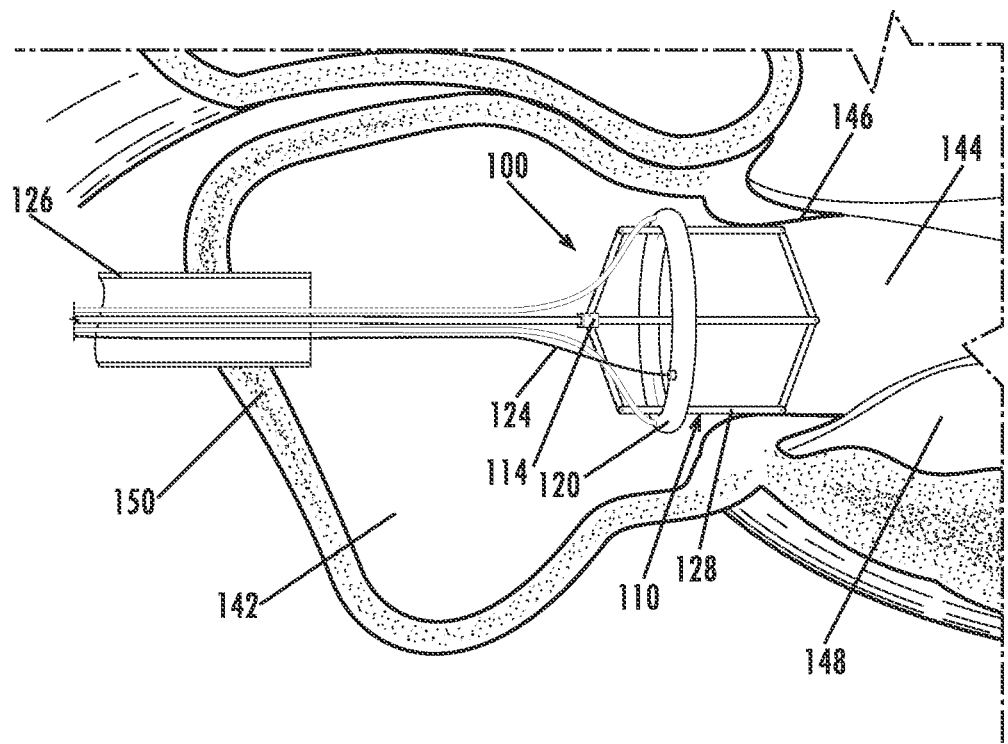
FIG. 7 is a schematic view showing the annular implant delivery device of FIG. 1 anatomically positioned in the mitral valve of a heart, with the device in an expanded configuration.

FIG. 7 continues the sequence. Once the deployment regions 128 of the deployment members 110 are extending through the mitral valve 144, the deployment members 110 may be expanded to an expanded configuration by moving the proximal joining member 114. At this point, the annular implant 120 is not yet in contact with the mitral annulus, and the annular implant 120 itself has not been adjusted outward, as shown in FIG. 7. Alternatively, the deployment members 110 may have been passively expanded by adjusting the size or shape of the annular implant 120 using the adjustment tool 124.

Figure 8:
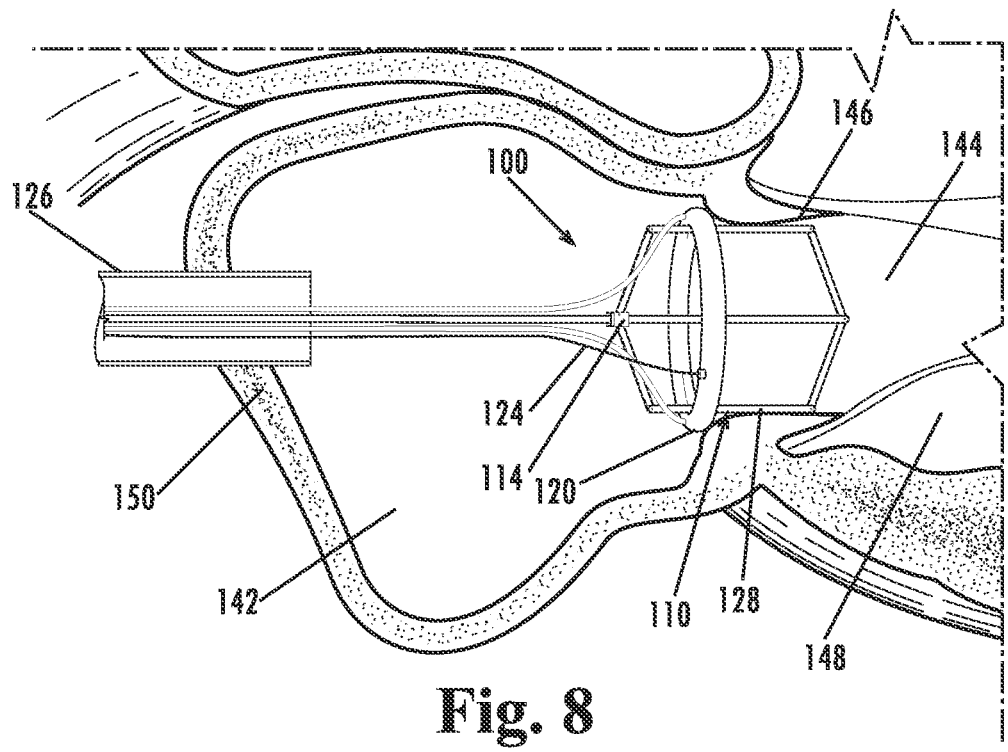
FIG. 8 is a schematic view showing the annular implant delivery device of FIG. 1 anatomically positioned in the mitral valve of a heart, with the device in an expanded configuration. The annular implant is shown anatomically positioned in the mitral annulus after it has been adjusted to its maximum circumference and advanced to contact the annulus.

With the annular implant 120 at its partially deployed state, the delivery device 100 is advanced further into the mitral valve 144 until the implant 120 is blocked by the top of the annulus from advancing further. The annulus acts as a physical signal, stopping the delivery device 100 once the implant 120 is snug against the annulus, as shown in FIG. 8. Visual confirmation of the proper placement may be confirmed, such as with TEE.

The deployment members 110 can then be passively fully expanded by adjusting the annular implant 120 to its maximum deployment circumference using the adjustment tool 124. The device 100 thus includes multiple means of annular control: by movement of the deployment members 110 to a more expanded or collapsed configuration and by adjustment of the implant 120 to a larger or small size or shape. Prior to implantation, the size of the annular implant 120 is increased until a predetermined tension is reached, which permits reshaping of the annular tissue to match the delivery configuration of the implant 120. In one embodiment, the tension is measured by a slip clutch as a maximal radial force limitation for the implant. The slip clutch can be programmed for a maximum radial force determined based upon the fragility of the annular tissues with which it is in contact. Once the slip clutch measures the programmed maximum radial force, it releases and prevents the adjustment tool 124 from expanding the annular implant 120 further. The circumference of the annular implant 120 at that time is its maximum deployment circumference.

With the annular implant 120 at its deployment circumference, this expansion procedure advantageously forces the annulus to conform to the shape and size of the implant 120, ensuring that the annulus is stretched to a point that creates proper interfacing of the implant 120 with the annulus. At its maximum deployment circumference, the implant 120 is contiguous to the annulus at all attachment points and non-targeted leaflet tissues have been pushed aside, allowing secure attachment of the implant 120 to the annulus, for proper implant function and safety.

The deployment members 110, barrels 118 or the annular implant 320 may include touchdown sensors that detect contact with the annulus, to confirm that there is contact between the implant 320 and the annulus at each point of attachment. The touchdown sensors can incorporate any mechanism known in the art, such as compressible buttons, resistance meters, or EKG sensors. In one embodiment, the touchdown sensors communicate with the control interface.

Once the surgeon is satisfied with the placement of the annular implant 120, the annular implant 120 is secured to the annular tissue 140 using attachment elements 136, as shown in FIGS. 9A-D. The number of attachment elements can vary. In a preferred embodiment, there is one attachment element 136 per barrel 118, making the number of attachment elements 136 the same as the number of barrels 118. The attachment elements 136 can be deployed individually or simultaneously, as described in more detail below. The deployment regions 128 continue to push the mitral leaflets 146 apart and toward the left ventricle 148 during the expansion and securing processes.

Figure 9A:
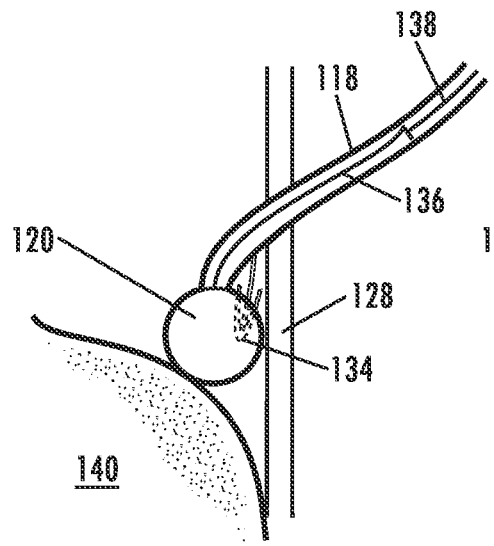
FIGS. 9A-D are a series of perspective views showing the barrel element of the annular implant delivery device of FIG. 1. In all of these views, the anchoring element is shown securing the annular implant to the delivery device.

FIGS. 9A-D shows the operation of one embodiment of an attachment element 136 being deployed from a barrel 118 to secure an annular implant 120 to annular tissue 140. In all of these views, the anchoring element 134 is shown securing the annular implant to the barrel 118. As shown in FIG. 9A, the barrel 118 contains an attachment element 136 in a distal portion and a corresponding attachment element release member 138 in contact with the proximal end of the attachment element 136. The release member 138 extends from the proximal end of the attachment element 136 through the proximal end of the barrel 118 to a control interface outside the patient's body. Using the control interface, the attachment element release member 138 can be manipulated to deploy the attachment element 136.

The embodiment shown is a nitinol attachment element 136 with a memory coil shape. The attachment element 136 is fittingly situated within the barrel 118 in biased position such that it is kept relatively straight and cannot move with respect to the barrel 118. The shape and size of the lumen can be chosen to fit the attachment element 136 and maintain its position, as described above. The barrel 118 thus prevents the nitinol attachment element 136 from assuming the coiled configuration it would assume if unrestrained.

The nitinol attachment element 136 can be designed to coil any amount sufficient to secure the annular implant 120 to the annular tissue 140, including ranging from about 270 to over 1000 degrees or optionally 360 degrees, 540 degrees, or 720 degrees. In a preferred embodiment, the attachment element 136 extends through the annular implant 120 into the annular tissue 140 and back into the annular implant 120 in an approximately 360 degree coil. Similarly, the length of the attachment element 136 should be selected according to the type of configuration to be long enough to properly secure the annular implant 120 to the annular tissue 140. In the embodiment shown, the nitinol attachment element 136 is long enough to extend through the annular implant 120 into the annular tissue 140 and back into the annular implant 120 when in its memory curled configuration.

Figure 9B:
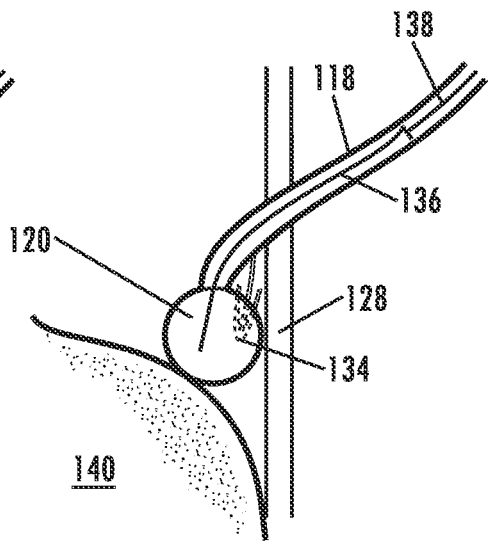
Figure 9C:
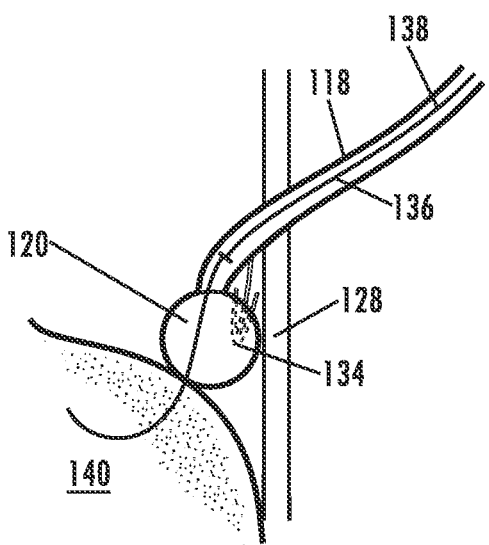
Figure 9D:
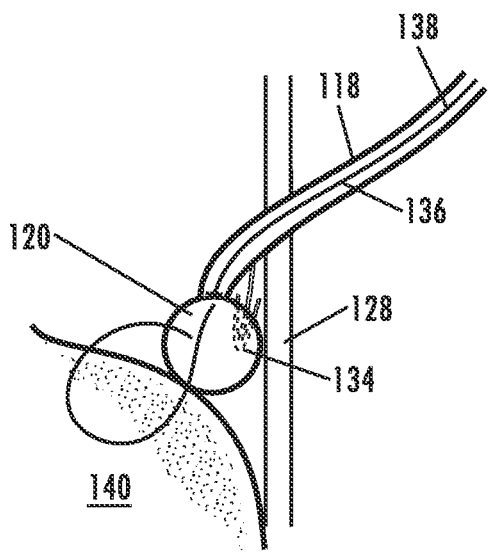

To begin deploying the attachment element 136, the attachment element release member 138 is manipulated to advance the attachment element 136 toward the distal end of the barrel 118. The release member 138 pushes the attachment element 136 to advance its distal tip out of the distal end of the barrel 118. The distal tip of the attachment element 136 then penetrates the annular implant 120, as shown in FIG. 9B. As the release member 138 is advanced further, more of the attachment element 136 exits the barrel and enters the annular implant 120. The attachment element 136 can remain relatively straight as it passes through the annular implant 120, as shown in FIG. 9B, due to the thickness of the implant material. The attachment element 136 proceeds through the annular implant 120 and reaches a point of contact between the annular implant 120 and the annular tissue 140. The attachment element 136 then extends from the annular implant 120 into the annular tissue 140. Once the attachment element 136 enters the annular tissue 140, it begins to curl due to the softness of the tissue 140. As the attachment element 136 proceeds through the annular tissue 140, the attachment element 136 curls significantly, as shown in FIG. 9C. Given its curled configuration, the distal tip of the attachment element 136 extends out of the annular tissue 140 and can ultimately re-enters the annular implant 120, as shown in FIG. 9D. At this time, the attachment element 136 has secured that point of attachment between the annular implant 120 and tissue 140.

After each of the attachment elements 136 has been deployed, the annular implant 120 is securely attached to the mitral annulus. Using the adjustment tool 224, the size or shape of the annular implant 120 can be modified to achieve the desired degree of annular reduction. In other embodiments, the planar orientation can be adjusted by the tool and adjustment mechanism. A variety of modalities for assessing mitral function, such as real time TEE, intravascular echocardiography, and intracardiac echocardiography, may be used to assess the physiologic effect of the implant 120 on mitral function. Further adjustments may be performed accordingly. Once a desired result has been achieved, the delivery device 100 may be retracted.

Figure 12A:
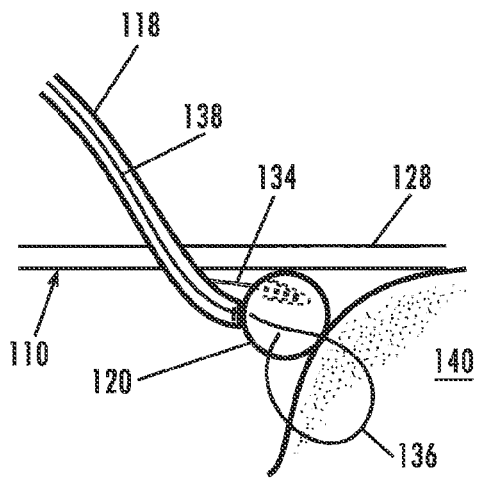
FIGS. 12A-D are a series of perspective views showing the anchoring element of the annular implant delivery device of FIG. 1. In all of these views, the attachment element remains in its secured position of FIG. 9D.
Figure 12B:
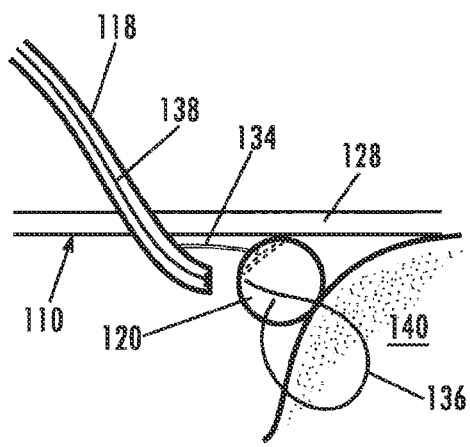
Figure 12C:
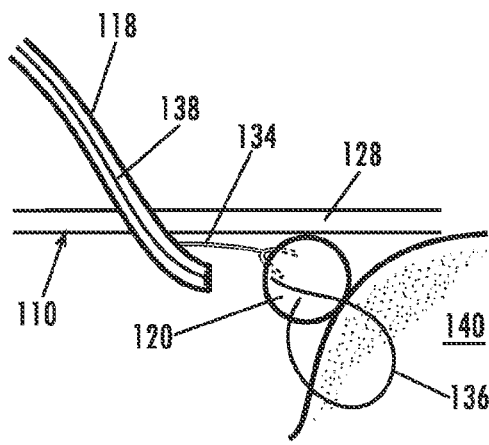
Figure 12D:
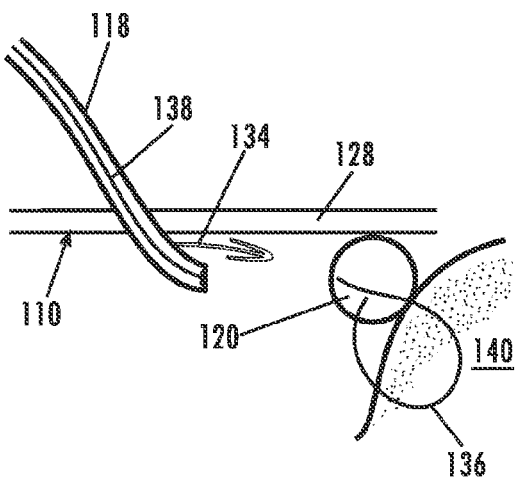

When the surgeon begins to retract the delivery device 100 into the left atrium 142 of the heart, the anchoring elements 134 are still attaching the annular implant 120 to the distal portions of the barrels 118. FIGS. 12A-D show the operation of an anchoring element 134 deformably releasing from the annular implant 120 as the deployment members 110 are retracted. In all of these views, the attachment element 136 remains secured in the annular implant 120 and tissue 140 as in FIG. 9D. FIG. 12A shows the anchoring element 134 attached to the annular implant 120, as it would be throughout the delivery procedure until this time. As the deployment members 110 pull away from the annular implant 120, the anchoring element 134 deforms within the annular implant 120, as shown in FIG. 12B. As the deployment members 110 are retracted further, the anchoring element 134 continues to deform until the prongs begin to exit the annular implant 120, as shown in FIG. 12C. Finally, the anchoring element 134 exits the annular implant 120 completely, and the annular implant 120 releases from the anchoring element 134. The anchoring element 134 may resume its original configuration, as shown in FIG. 12D. Once all of the anchoring elements 134 have released from the annular implant 120, the annular implant 120 is no longer secured to the deployment members 110.

Figure 13:
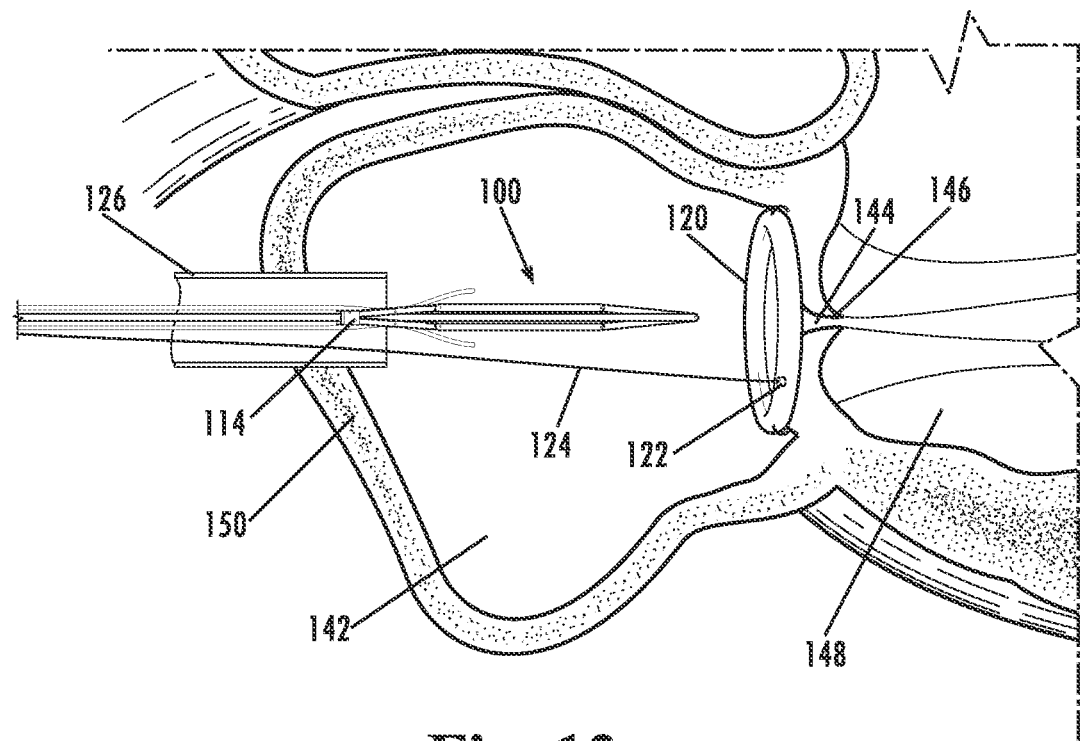
FIG. 13 is a schematic view showing the annular implant delivery device of FIG. 1 anatomically positioned in the left atrium of a heart, with the device in a collapsed configuration being retracted back into the sheath. The annular implant and adjustment tool remain in place at the mitral annulus.
Figure 14:
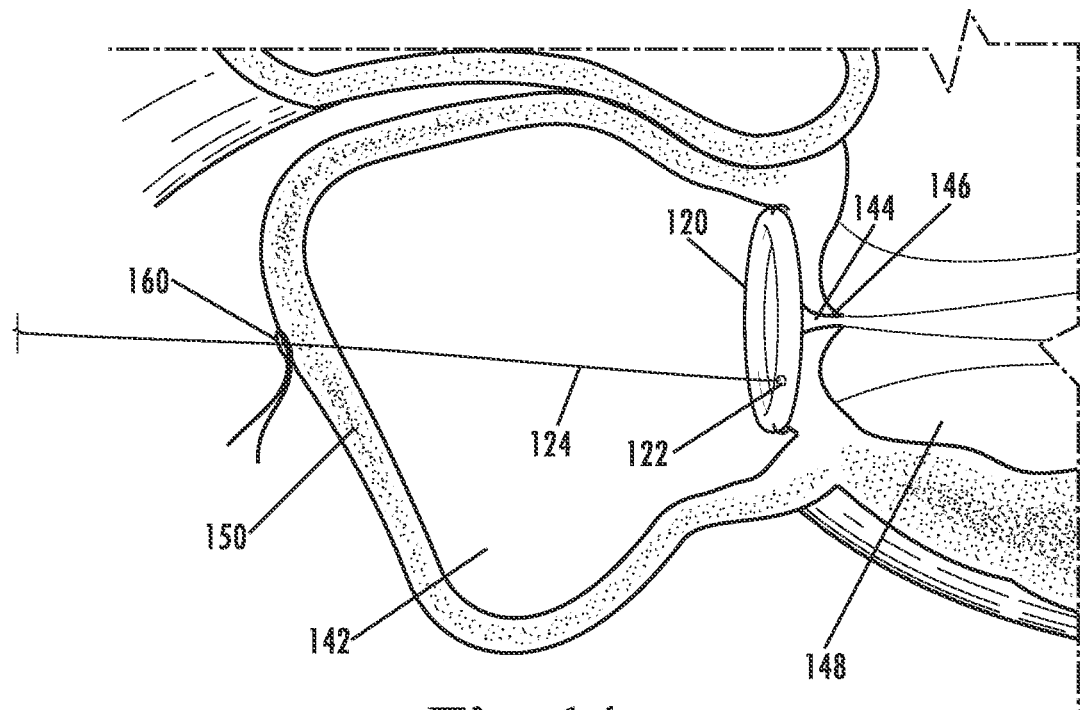
FIG. 14 is a schematic view showing the annular implant and adjustment tool of FIG. 1 anatomically positioned in the mitral annulus of a heart after the annular implant delivery device has been removed. The adjustment tool extends through the left atrium and out of the heart.

As shown in FIG. 13, the delivery device 100 can be fully removed from the patient, leaving the annular implant 120 and adjustment mechanism 122 coupled to the adjustment tool 124 in place at the mitral annulus. Upon release of the anchoring elements 136, when the delivery device 100 is in the left atrium 142, the proximal joining member 114 is moved distally to bring the delivery device 100 back to a collapsed configuration. A collapsed delivery device 100 is then retracted further toward the wall 150 of the left atrium 142 and back into the sheath 126. Once a collapsed device 100 is housed in the sheath 126, the sheath 126 is removed from the patient's body through the myocardial and chest incisions. The sheath 126 is removed from the myocardial incision, using a Ramel or purse-string tourniquet 160 previously placed at the site as is typical in the art to prevent bleeding, as shown in FIG. 14. The annular implant 120 and coupled adjustment mechanism 122 are left secured to the annulus, and the adjustment tool 124 extends through the closed myocardial incision for post-operative adjustment, as also shown in FIG. 14.

Post-operative adjustment allows the size or shape of the implant 120 to be further affected after the delivery device 100 has been removed and normal physiologic flow through the heart has resumed. Adjustment of the adjustable implant 120 contemplates the use by the surgeon of diagnostic tools to provide an assessment of the nature of adjustment needed to achieve a desired effect. Such diagnostic tools include, but are not limited to, TEE, echocardiography, diagnostic ultrasound, intravascular ultrasound, virtual anatomic positioning systems integrated with magnetic resonance, computerized tomographic, or other imaging technologies, endoscopy, mediastinoscopy, laparascopy, thoracoscopy, radiography, fluoroscopy, magnetic resonance imaging, computerized tomographic imaging, intravascular flow sensors, thermal sensors or imaging, remote chemical or spectral analysis, or other imaging or quantitative or qualitative analytic systems.

Once satisfactory adjustments have been made, the adjustment tool 124 is disengaged from the adjustment mechanism 122 and removed from the patient's body and the Ramel or purse-string tourniquet is further tightened and tied off. The chest incision can then be closed, if it is not already closed. The adjustment tool 124 can be capable of removal from the body, or might be retained within the body indefinitely. In various embodiments, the adjustment mechanism 122 may be configured to allow re-introduction of the adjustment tool 124 for adjustment. Furthermore, alternate methods for use of an adjustable implant may provide for the periodic, post-implantation adjustment of the size of the implant to fit the annulus as needed to accommodate growth of the site in a juvenile patient or other physiologic changes and needs of the patient.

Figure 15A:
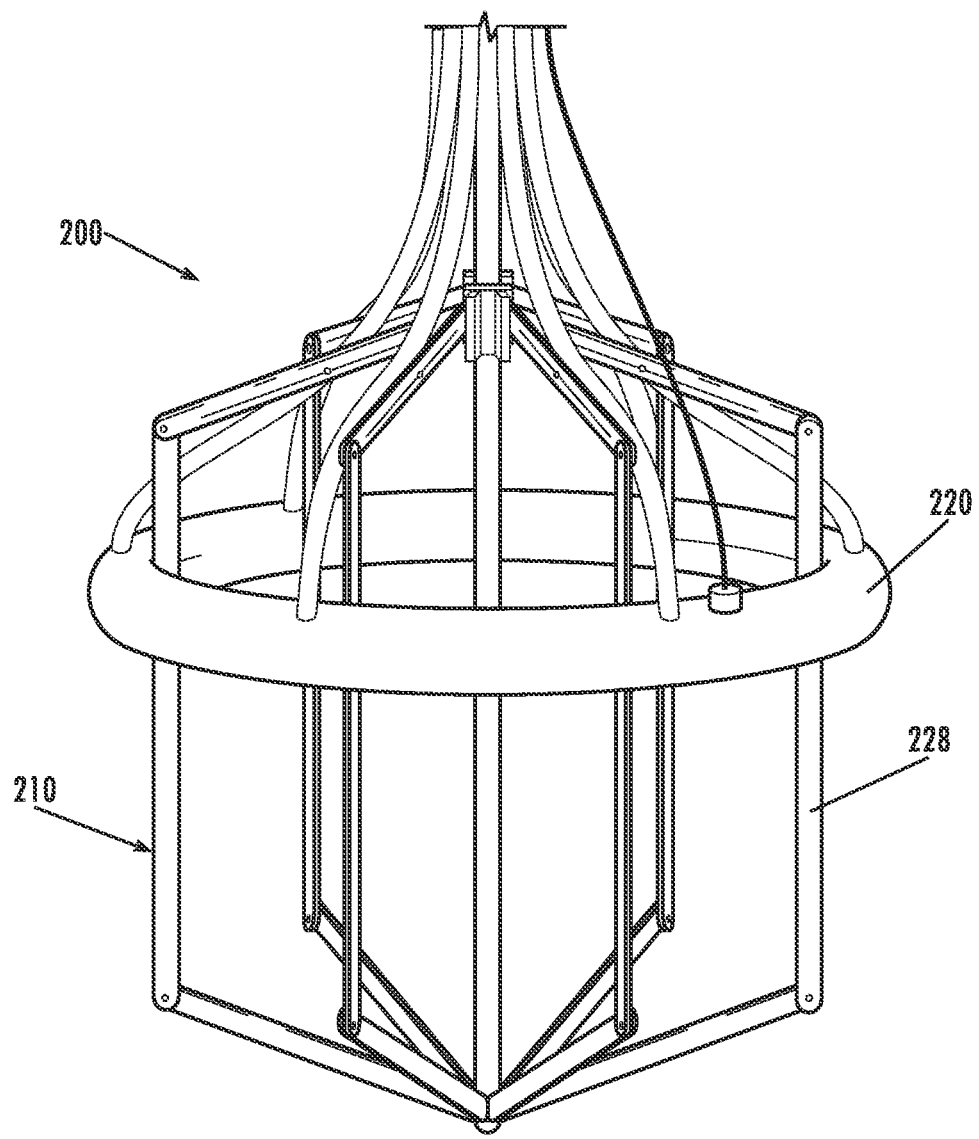
FIGS. 15A-C are a series of schematic views showing an embodiment of the annular implant delivery device with six deployment members.
Figures 15B, 15C:
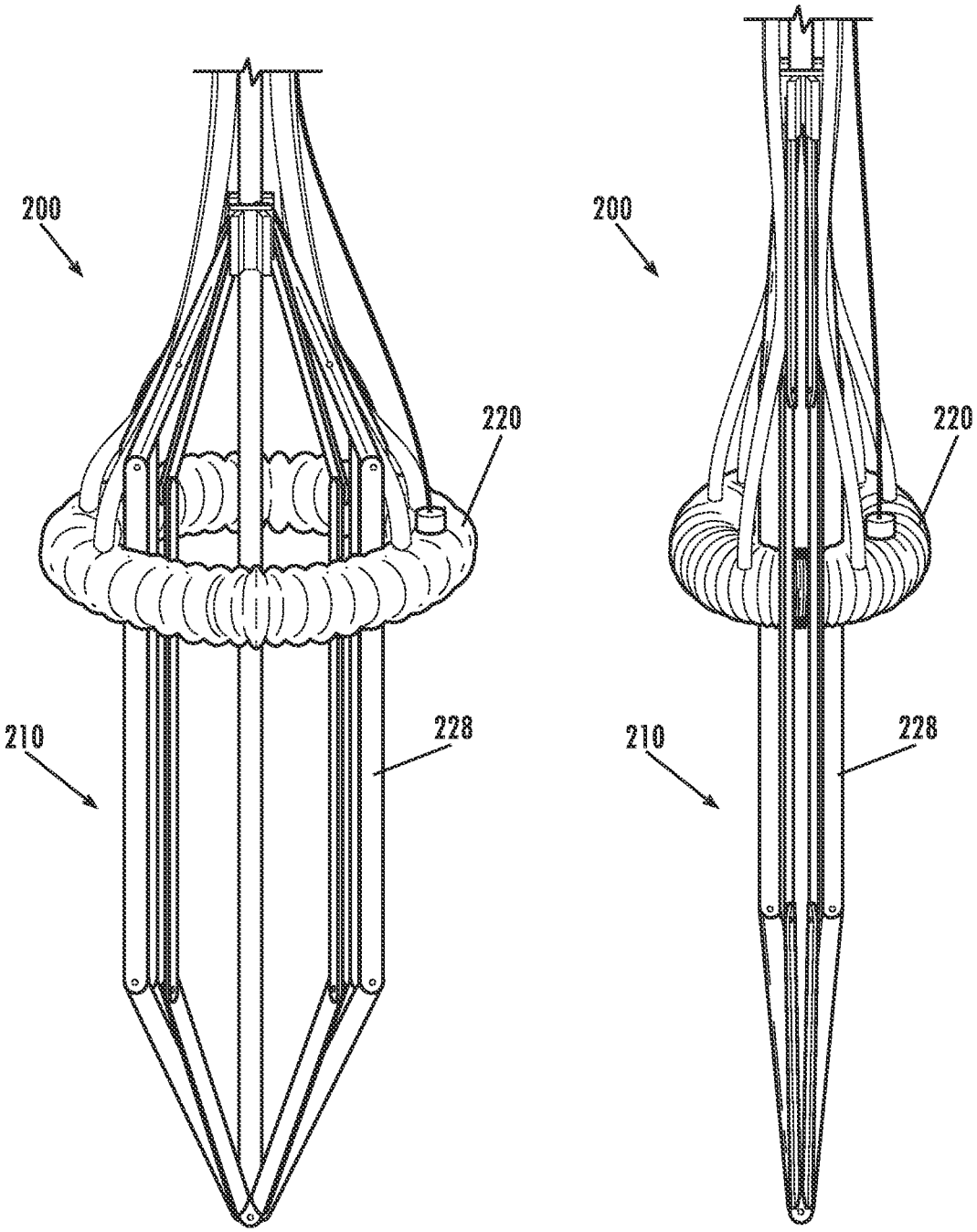

Another embodiment of the annular implant delivery device is shown in FIG. 15A in an expanded configuration, in FIG. 15B in the partially expanded configuration, and in FIG. 15C in a collapsed configuration. The delivery device 200 is shown to include six deployment members 210. This embodiment functions similarly to the embodiment discussed above and is also suited for use in mitral valve applications. With six deployment members 210, the shape of the deployment regions 228 of the deployment members 210 approximates a cylinder when the deployment members 210 are in an expanded configuration. The embodiment with six deployment members 210 provides multiple points of attachment between the annular implant 220 and the annulus.

Figure 16A:
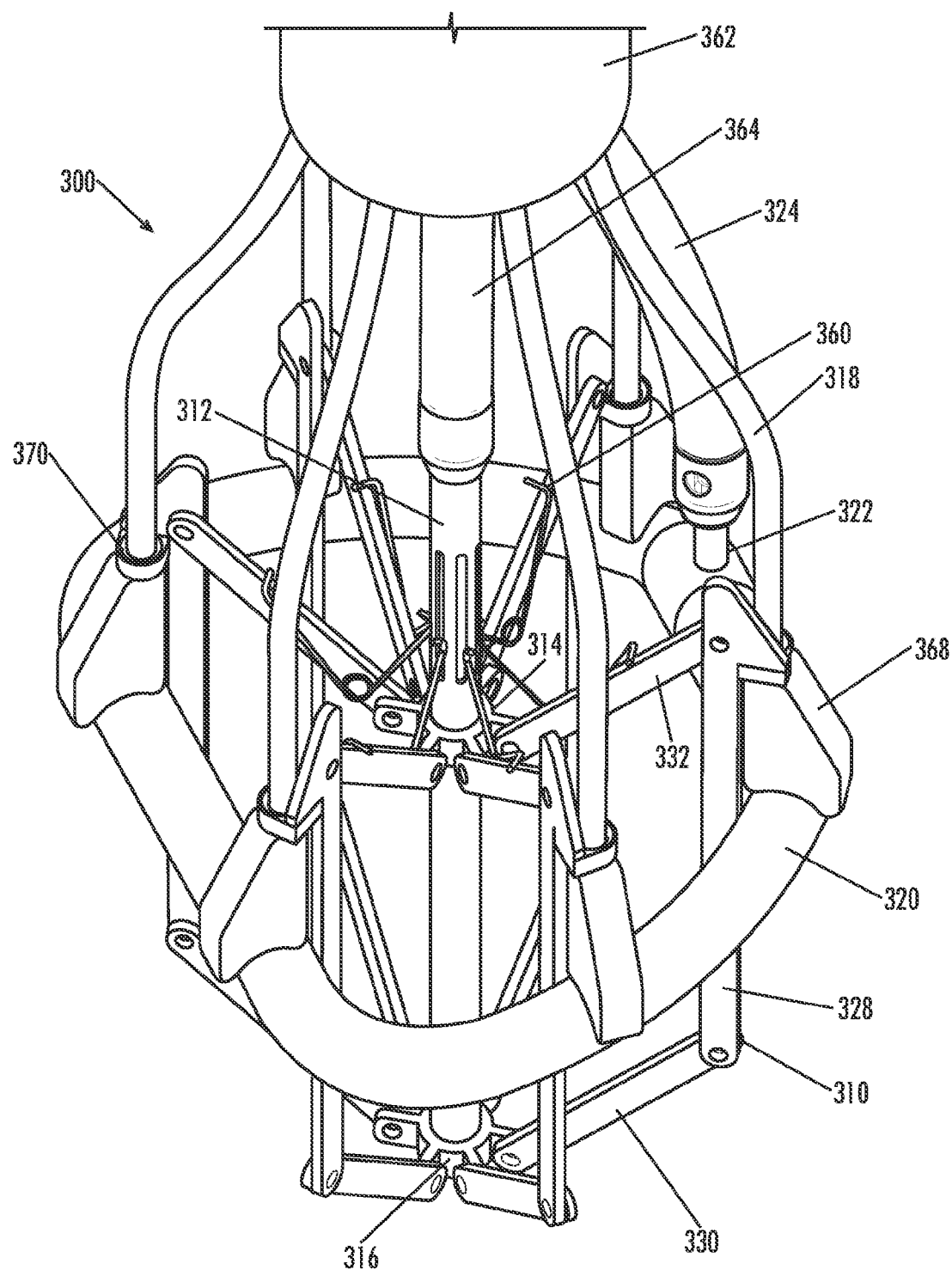
FIGS. 16A-C are a series of perspective views of another embodiment of the annular implant delivery device.
Figure 16B:
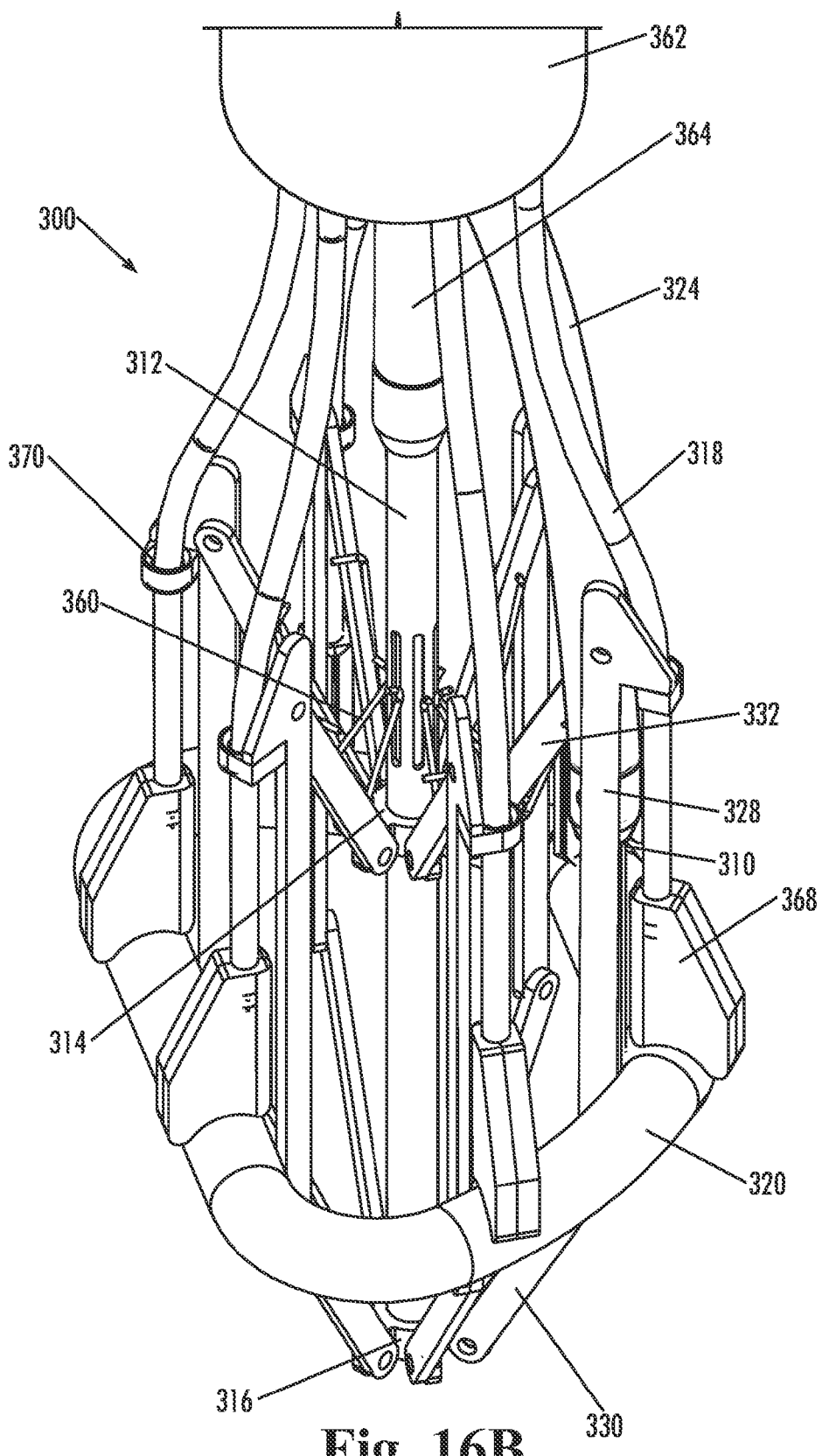
Figure 16C:
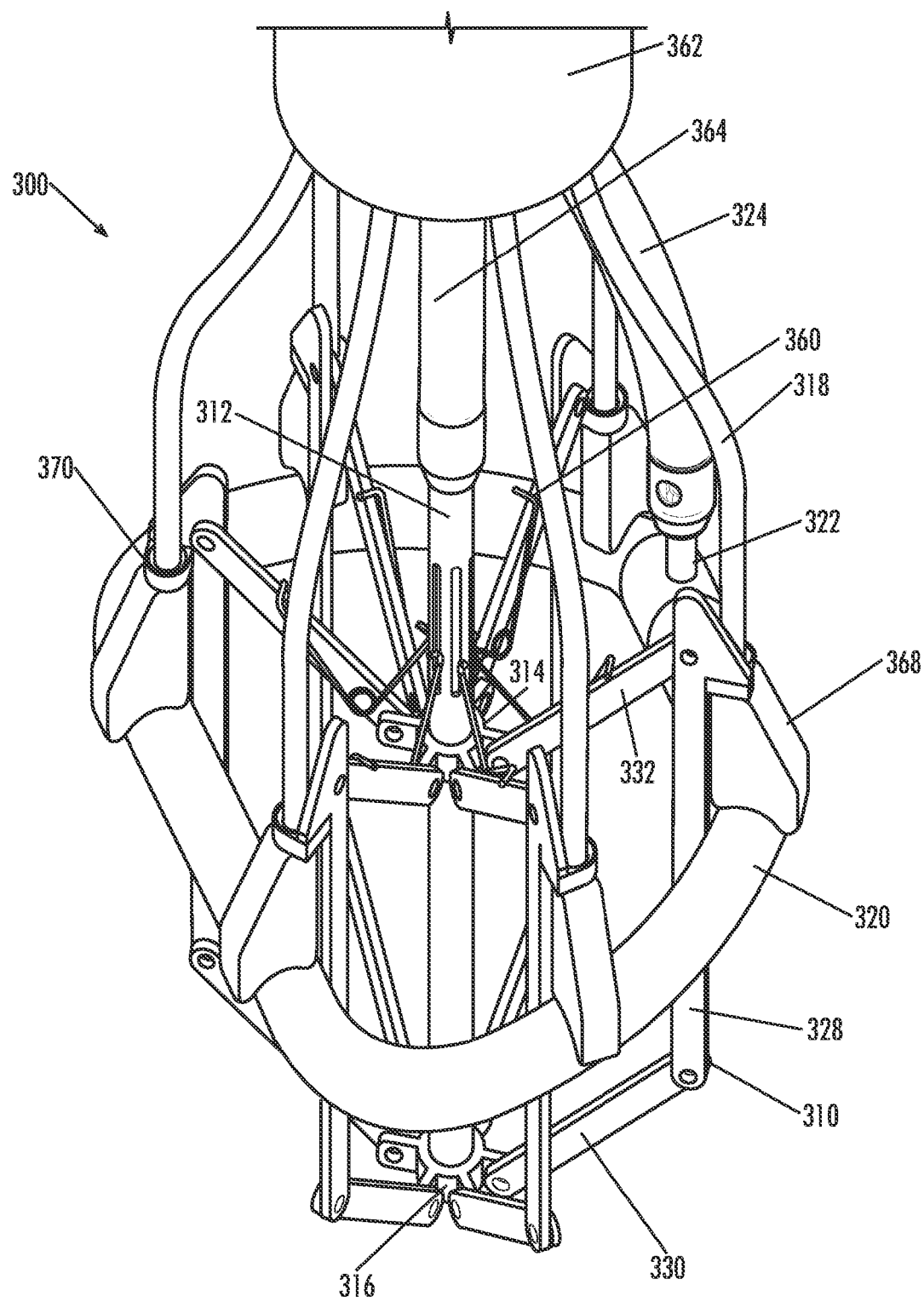

FIGS. 16A-C show another embodiment of the delivery device, which is also designed for delivery of an annular implant to the mitral annulus of a heart. All of the options discussed for the previous embodiments and for each component part thereof are applicable to the following embodiment, although they may not be expressly restated. Also, the details of the surgical delivery and implantation procedure discussed above are applicable to the following embodiment, although they may not be expressly restated. FIG. 16A shows the annular implant delivery device 300 in an expanded configuration. FIG. 16B shows the annular implant delivery device 300 in a partially expanded configuration with the deployment members advancing along the barrels. FIG. 16C shows the annular implant delivery device 300 in a partially expanded configuration.

The delivery device 300 includes deployment members 310, a central support member 312, a proximal joining member 314, a distal joining member 316, biasing members 360, a sleeve 364, barrels 318 having slidably mounted thereon directing cuffs 370, as well as an annular implant 320. The annular implant 320 includes a coupled adjustment mechanism 322 and a selectively engageable adjustment tool 324. The delivery device 300 is shown extending from a sheath 362. The delivery device 300 is shown to include six deployment members 310. However, alternative embodiments can contain any number of a plurality of deployment members 310. The deployment members 310 contain a flexible joint at each end of the deployment region 328 that allow the angles between contiguous regions of the deployment members 310 to vary, thereby allowing the deployment members 310 to expand and contract.

The deployment members 310 are joined at the proximal joining member 314, which is a cuff surrounding the central support member 312 with an extension corresponding to each deployment member 310, to which the deployment members 310 attach. The deployment members 310 are also joined at the distal joining member 316, which is another cuff surrounding the central support member 312 with extensions to which the deployment members 310 attach. Both the proximal joining member 314 and the distal joining member 316 shown are fixed to the central support member 312 such that they cannot slide along the central support member 312. However, the invention contemplates embodiments wherein said cuffs 370 have a limited range of axial freedom along the central support member 312.

The deployment members 310 are flexibly attached to the proximal joining member 314 and distal joining member 316, allowing the angle between the central support member 312 and the proximal regions 332 and distal regions 330, respectively, to change. The distal regions 330 are shown to extend upward and outward toward the deployment regions 328, such that they spread the mitral leaflets 346 when inserted into the mitral valve 344. The proximal regions 332 are shown to extend inward and downward toward the central support member 312, such that the proximal ends of the deployment members 310 and, in turn, the proximal joining member 314, do not extend proximally beyond the deployment regions 328. The location of the proximal ends and the proximal joining member 314 with respect to the deployment regions 328 will change as the deployment members 310 are expanded and contracted. For example, when fully expanded, the proximal regions 332 may extend perpendicular to the deployment regions 328, and they may extend at a more downward angle the more the deployment members 310 collapse.

The biasing members 360 extend between the central support member 312 and the proximal regions 332 of the deployment members 310. The biasing members 360 may be attached to the proximal region 332 using any known means of attachment. Preferably, each biasing member 360 is attached to the central support member 312 through an elongated slot, along which the biasing member 360 can slide. Unrestrained, the biasing members 360 exert a constant outward force on the proximal regions 332, tending to force the deployment members 310 to expand. The biasing members 360 can be coiled, hairpin, or any other known configuration imparting a biasing force. In a preferred embodiment, the biasing members 360 include a single coil, as shown. Although the outward force created by the biasing members 360 is constant, expansion of the deployment members 310 is limited by the size and shape of the annular implant 320. The biasing members 360 each apply an equal force, but because each deployment member 310 can move independently, the deployment members 310 as a whole will take the size and shape of the annular implant 320. The strength of the biasing force can vary and should be chosen to suit the surgical application.

The barrels 318 and central support member 312 are shown extending proximally into the sheath 362. The sheath 362 houses the delivery device 300 for insertion into a patient and upon retraction from a patient after the annular implant 320 has been implanted. It is desirable to restrain the movement and outward force of the biasing members 360 when the device 300 is being advanced from the sheath 362 and being withdrawn back into the sheath 362, to enable the deployment members 310 to collapse. The sleeve 364 covers and holds part of each biasing member 360 within the slot in the central support member 312 when it is pushed distally toward the proximal joining member 314 to effect contraction of the deployment members 310. The sleeve 364 can also retract along the central support member 312 to effect expansion of the deployment members 310. Advancement and retraction of the deployment members 310 will be discussed further below, in the context of a series of figures showing operation of the device 300.

Figure 17:
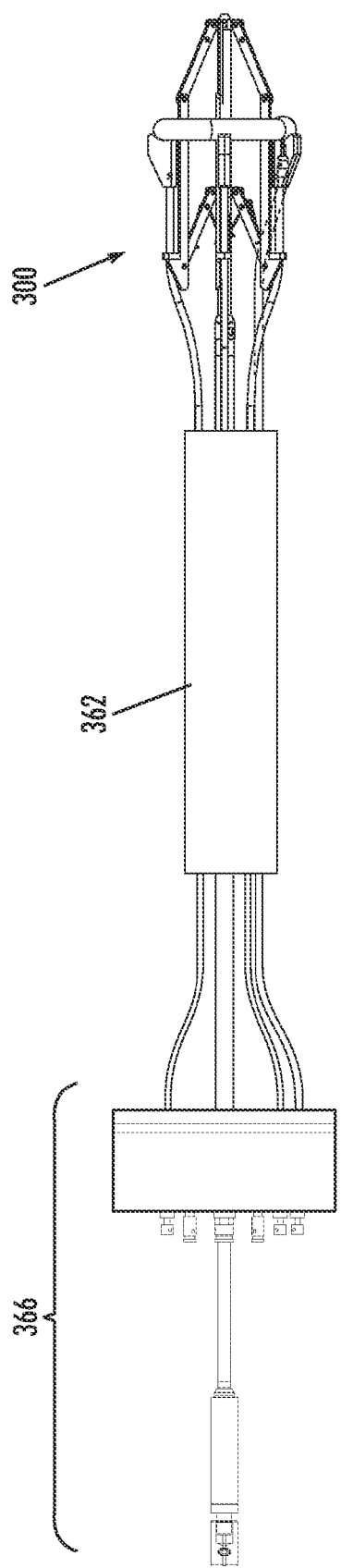
FIG. 17 is a schematic view showing the annular implant delivery device of FIG. 16 extending through a sheath to an attached control interface.

FIG. 17 shows an overhead view of the annular implant delivery device 300 of FIG. 16, including the sheath 362 from which the device 300 extends and the control interface 366 to which the device 300 is connected. The device 300 is fully housed in the sheath 362 when inserted into a patient, as discussed below, and the control interface 366 remains outside of the patient at all times. The control interface 366 includes a control switch, such as a button or joystick, corresponding to each barrel 318 and to the adjustment tool 324, as well as an elongated handle corresponding to the central support member 312. The control interface 366 acts as the main controller for each part of the delivery device 300, and its uses include: to advance the delivery device 300 out of the sheath 362, to adjust the orientation of the annular implant 320, to advance and steer the delivery device 300 to the annulus, to adjust the size and shape of the annular implant 320 to shape match and annulus with the implant 320, to deploy attachment elements to attach the implant 320 to the annular tissue, and to withdraw the deployment members 310 from the annulus upon implantation of the implant 320. These uses will be further explained below at the appropriate point during operation of the device.

Figure 18:
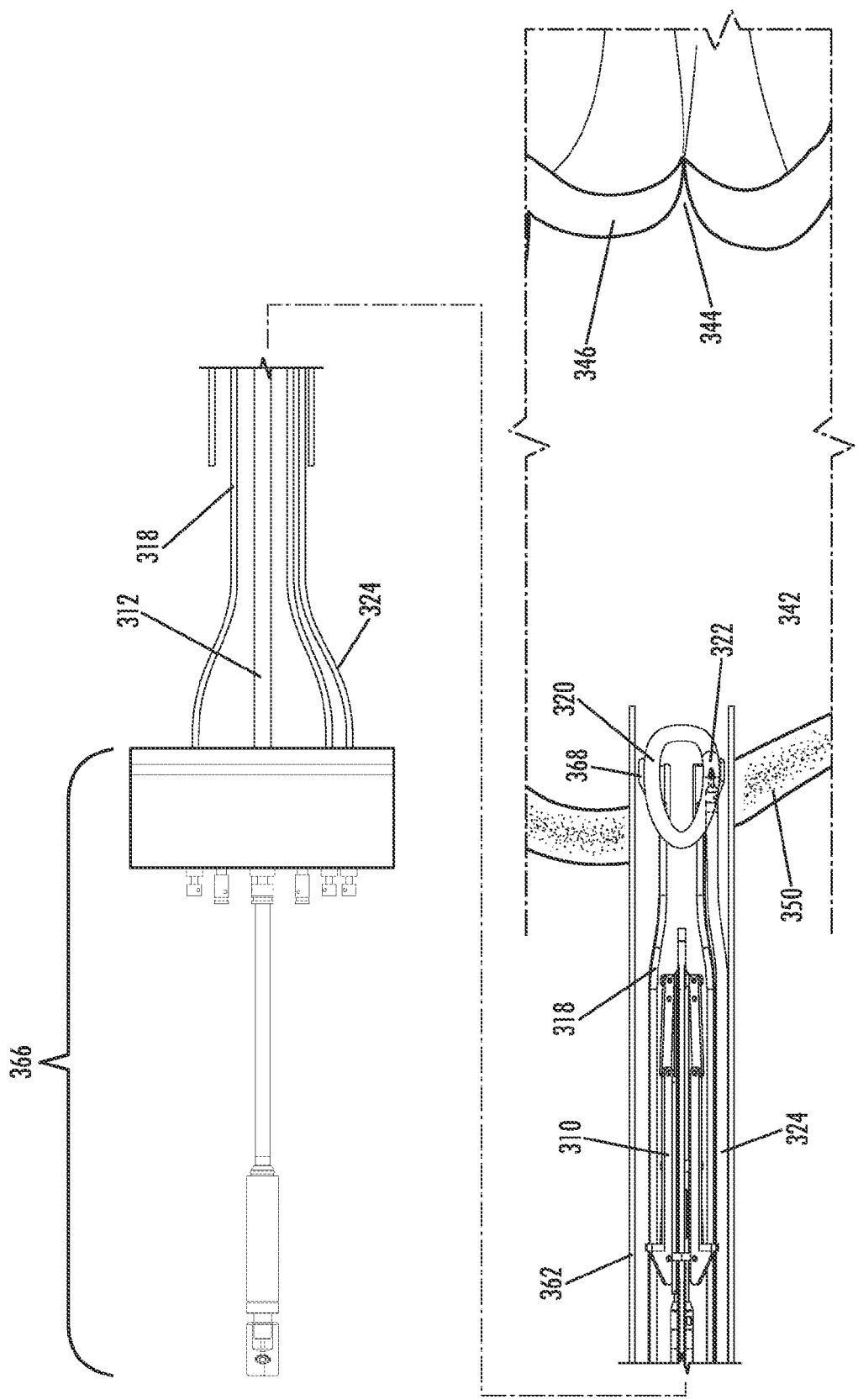
FIG. 18 is a schematic view showing the annular implant delivery device of FIG. 16 anatomically positioned in a wall of the left atrium of a heart with the device in a collapsed configuration inside a sheath, and the attached control interface outside of a patient.

FIGS. 18-28 depict a sequence of the operation of the annular implant delivery device of FIG. 16 to deliver an implant to the mitral annulus of a patient's heart. FIG. 18 shows the annular implant delivery device 300 anatomically positioned in the wall 350 of the left atrium 342 of a heart, with the delivery device 300 in a collapsed configuration inside of a sheath 362. As explained in connection with a previous embodiment, the sheath 362 can be inserted into a patient through an incision in the patient's chest and is directed into the left atrium 142 of the patient's heart through a myocardial incision in the wall 150 of the left atrium 142. The invention also contemplates other minimally invasive percutaneous, trans-atrial or pulmonary artery delivery routes.

As shown in FIG. 18, inside the sheath 362 the deployment members 310 are in a collapsed configuration, as is the annular implant 320, and the deployment members 310 do not extend through the implant 320. The deployment members 310 are surrounded by the barrels 318, which extend from their attachment points on the implant 318 proximally through the sheath 362 to the control interface 366. The annular implant 320 is closer to the tip of the sheath 362 than the deployment members 310 so that the implant 320 can be advanced from the sheath 362 first. If the annular implant 320 is not round, the longer axis of the implant 320 extends in the direction parallel to the sheath 362. The implant 320 can be made of a variety of materials and have a variety of structures and surfaces as discussed above.

The distal portion of each barrel 318 is designed to fittingly sit on the implant 320 with the saddle members 368. The barrels 318 are attached to the annular implant 320 by anchoring elements (shown in detail in FIGS. 26A-C) such that the implant 320 and barrels 318 advance from the sheath 362 together. The anchoring element can be any known attachment mechanism. In one embodiment, the anchoring element is a suture which extends from the control interface 366 distally through the barrel 318, around the implant 320, and back through the barrel 318 proximally to the control interface 366. The suture may be tied at the control interface 366, creating a single connected thread. To detach the barrel 318 from the implant 320, the suture is cut at the control interface 366, and one side is pulled through the barrel 318 until the suture no longer contacts the implant 320. The suture may be pulled until the entire thread is removed from the barrel 318. In another embodiment, the anchoring element is a wire which extends from the control interface 366 distally through the barrel 318 and wraps around the implant 320 at least one time. To detach the barrel 318 from the implant 320, the wire is pulled at the control interface 366 to unwrap the wire from the implant 320, and the wire may be fully removed from the barrel 318. The strength and thickness of the wire can be chosen to ensure secure attachment and to allow removal by a pulling force. The wire or a portion of the wire may be made of a shape memory material.

Figure 19:
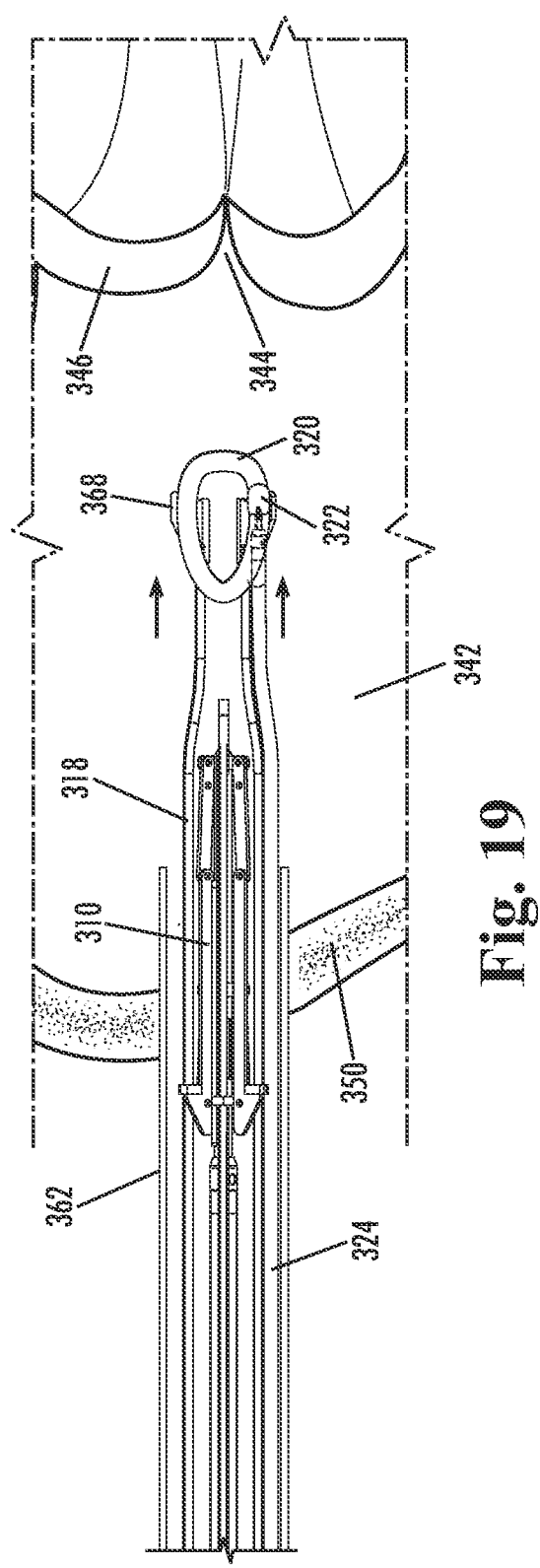
FIG. 19 is a schematic view showing the annular implant delivery device of FIG. 16 anatomically positioned in the left atrium of a heart with the annular implant and barrel elements advanced out of the sheath and the deployment members in a collapsed configuration advancing from the sheath.
Figure 20:
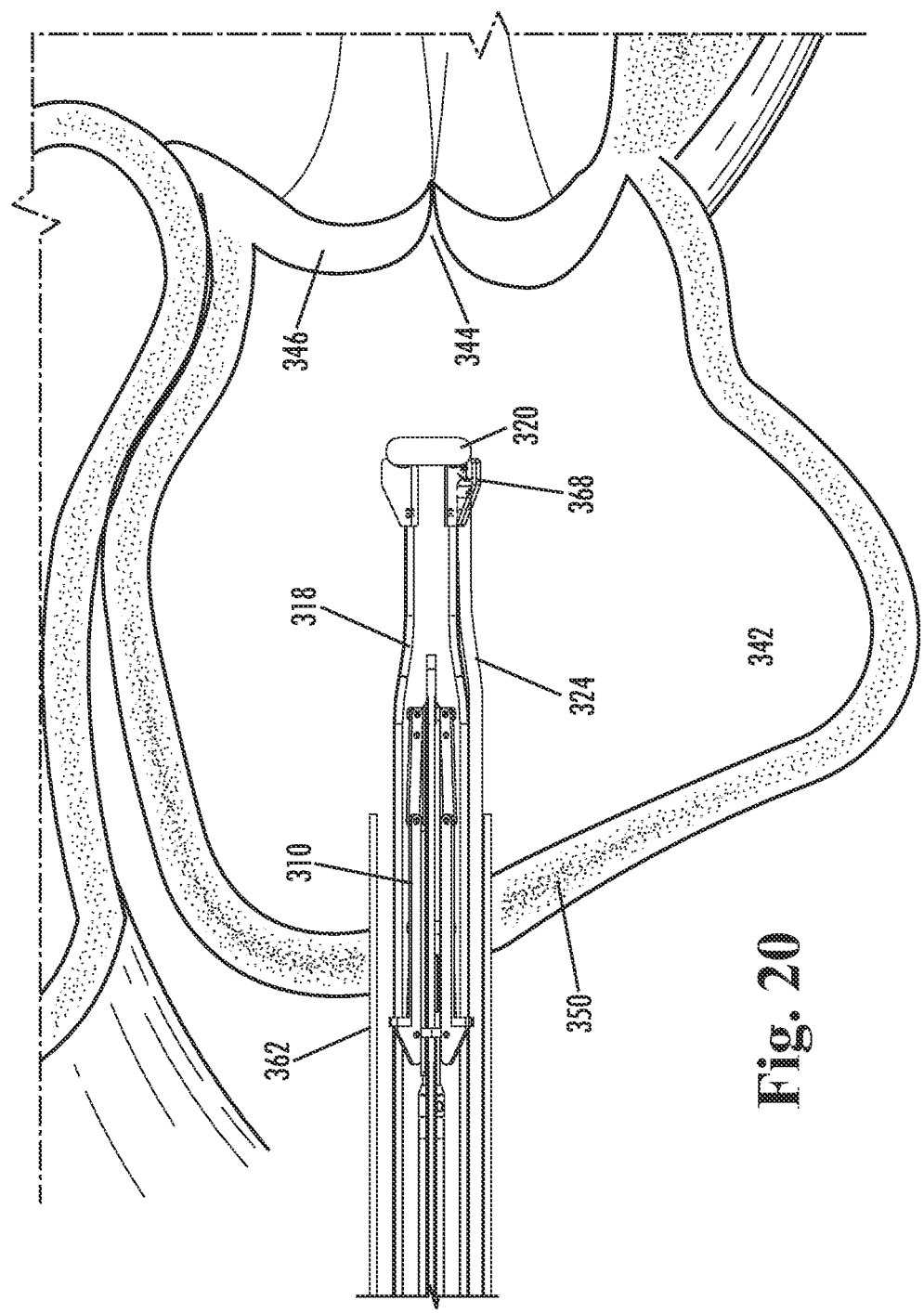
FIG. 20 is a schematic view showing the annular implant delivery device of FIG. 16 anatomically positioned in the left atrium of a heart with the annular implant and barrel elements advanced out of the sheath, with the implant in a perpendicular orientation, and the deployment members in a collapsed configuration advancing from the sheath.

As shown in FIG. 19, the annular implant 320 and barrels 318 are advanced from the sheath 362 in a direction parallel to the sheath 362 by manipulating the control interface 366. The deployment members 310 remain in the sheath 362. By manipulating the angle of the control interface 366, affecting the relative movement of the barrels 318, the orientation of the annular implant 320 is adjusted until it is approximately perpendicular to the sheath 362, as shown in FIG. 20. In one embodiment, pushing the control interface 366 forward advances the implant 320 forward, and angling the control interface 366 to one side in a manner analogous to a marionette board moves the corresponding side of the implant 320, such as to make it perpendicular to the sheath 362.

Figure 21:
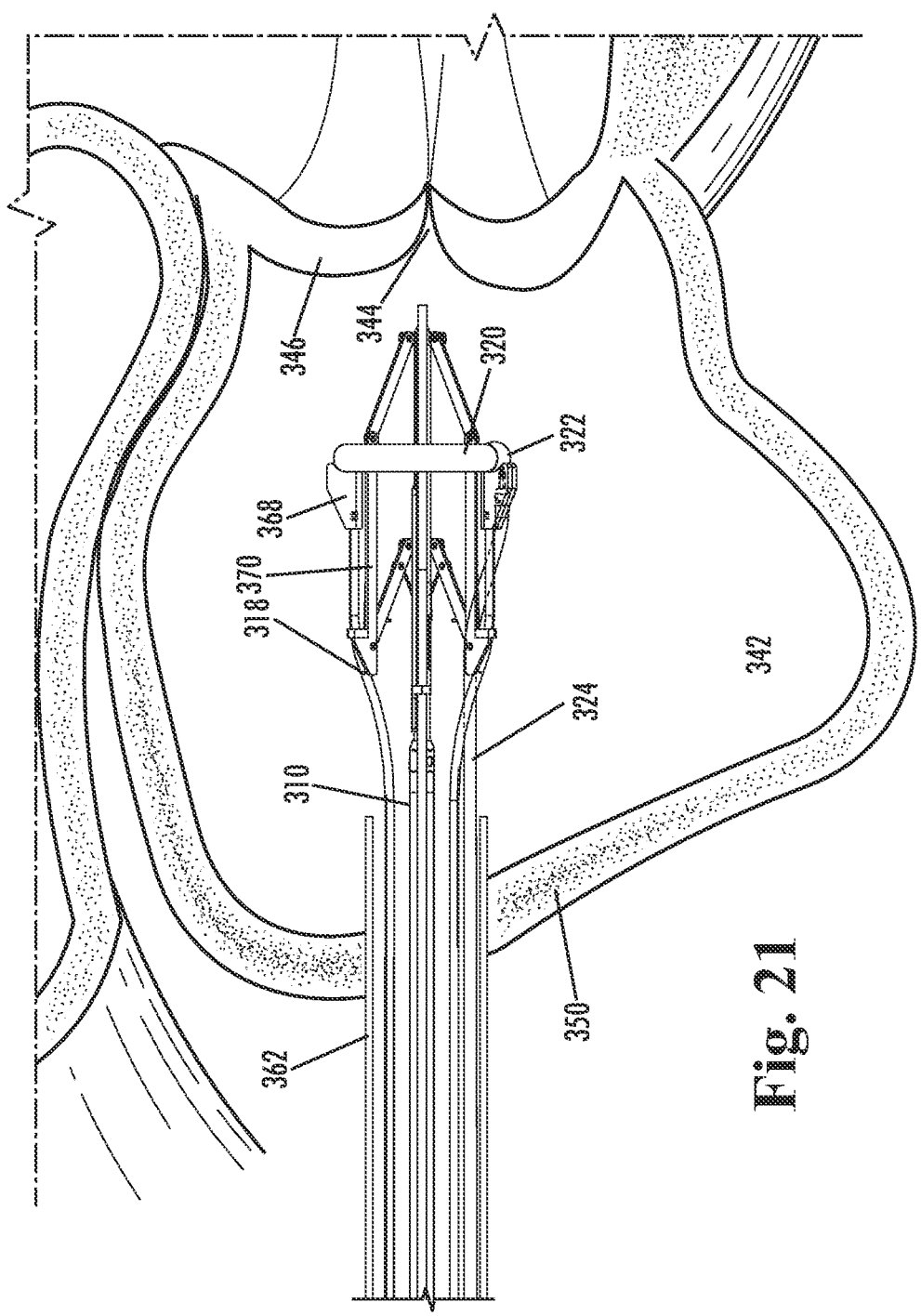
FIG. 21 is a schematic view showing the annular implant delivery device of FIG. 16 anatomically positioned in the left atrium of a heart with the deployment members advancing along the barrels toward the annular implant in a collapsed configuration.
Figure 22:
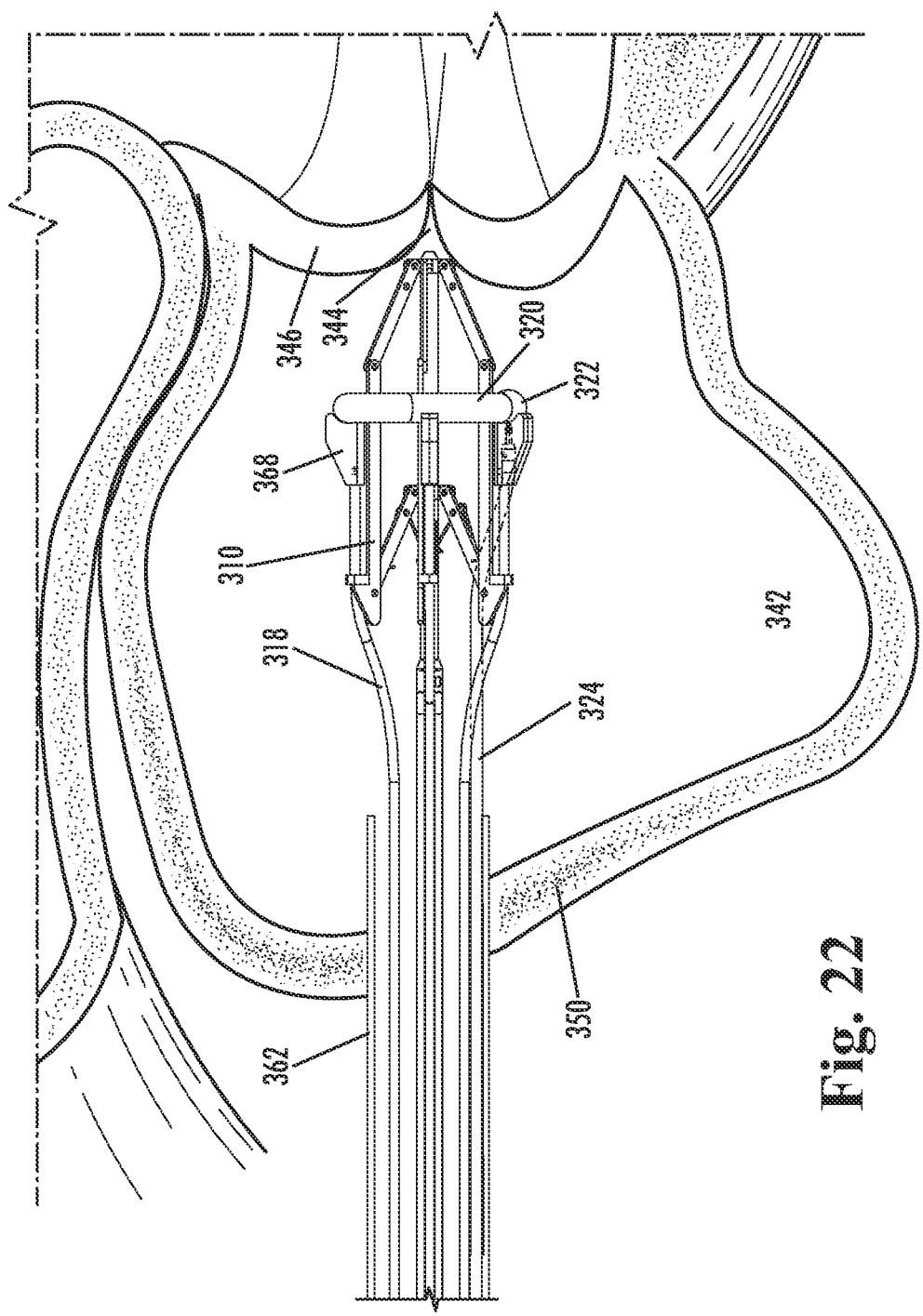
FIG. 22 is a schematic view showing the annular implant delivery device of FIG. 16 anatomically positioned in the left atrium of a heart with the deployment members advancing along the barrels through the annular implant in a partially expanded configuration.
Figure 23:
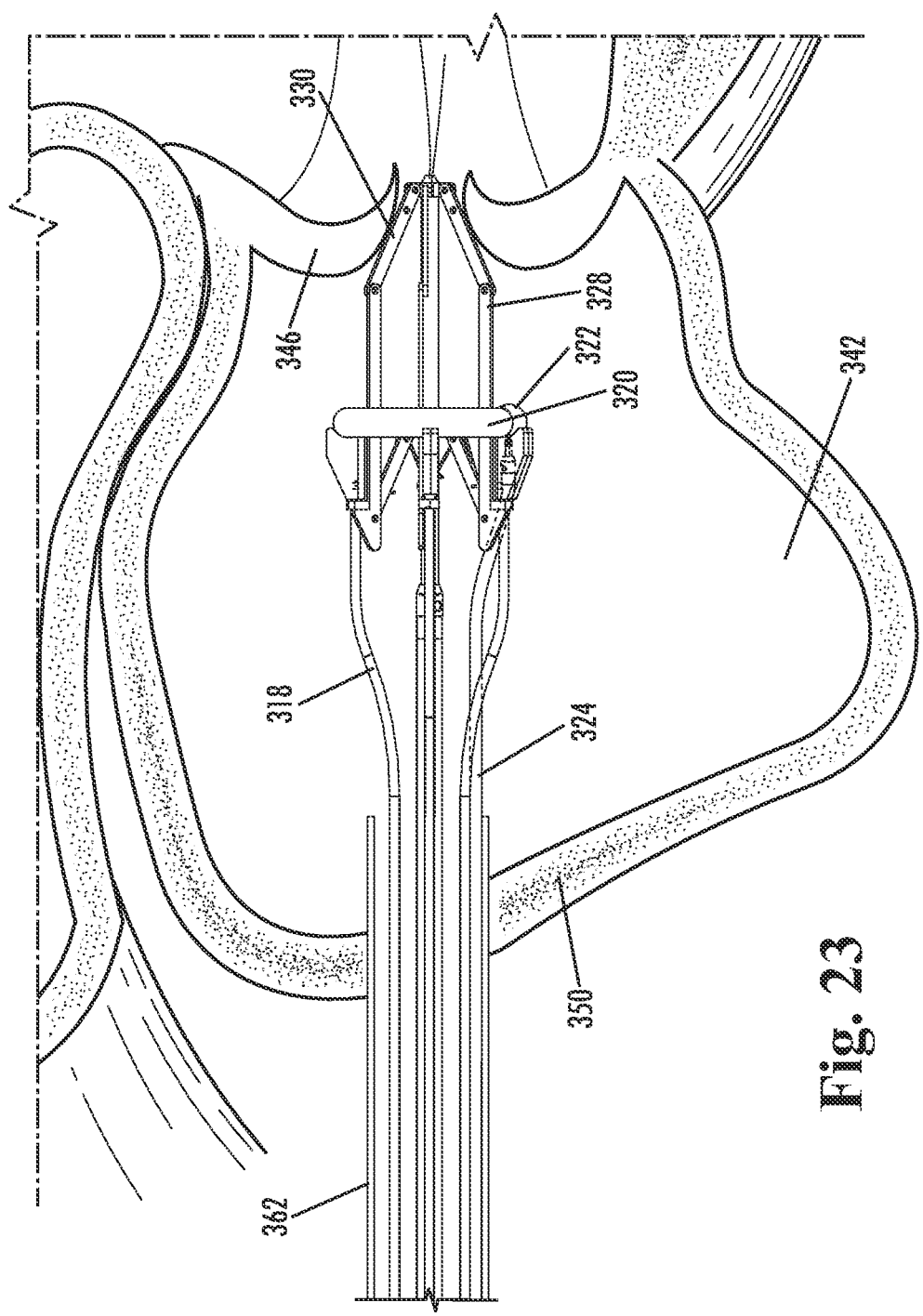
FIG. 23 is a schematic view showing the annular implant delivery device of FIG. 16 anatomically positioned in the left atrium of a heart and contacting the mitral leaflets with the device in a partially expanded configuration.

As shown in FIGS. 21-23, when the annular implant 320 and barrels 318 are in the desired perpendicular orientation, they create a pathway for advancing the deployment members 310. Using the handle on the control interface 366 which corresponds to the central support member 312, the deployment members 310 are advanced out of the sheath 362 along the barrels 318 and through the implant 320, as shown in FIG. 21. In one embodiment, pushing the handle forward moves the central support member 312 and, in turn, the deployment members 310, forward and out of the sheath 362. The sleeve 364 may still be covering the biasing members 360 while the deployment members 310 are advanced through the implant 320, to limit their outward force. The deployment members 310 are slidably connected to the barrels 318 by directing cuffs 370. This sliding connection allows the deployment members 310 to move separately from the barrels 318, such as staying within the sheath 362 while the barrels 318 advance with the implant 320 in the initial stages of the procedure discussed above. As the deployment members 310 are advanced forward through the implant 320, the directing cuffs 370 slide along the barrels 318, as shown in more detail in FIG. 16B. The deployment members 310 are advanced until the directing cuffs 370 contact the saddle members 368, as shown in more detail in FIG. 16C. The saddle members 368 act as stops for the directing cuffs 370, ensuring that the deployment members 310 advance the proper distance into the implant 320.

Once the directing cuffs 370 are in place at the saddle members 368, the delivery device 300 is advanced forward through the left atrium 342 toward the mitral annulus, as shown in FIG. 22. The deployment members may be in a partially expanded or expanded configuration. The sleeve 362 is retracted from the biasing members 360, if this has not already been done.

Once the sleeve 364 is retracted, the deployment members 310 will expand due to the outward force exerted by the biasing members 360. The size and shape of the annular implant 320 controls the expansion of the deployment members 310 throughout delivery and implantation. Each deployment member 310 expands to track the inner diameter of the implant 320 at the corresponding point, and the number and placement of the deployment members 310 can be chosen such that they substantially recreate the size and shape of the implant 320. Given the consistent outward force by the biasing members 360, the deployment members 310 substantially recreate the shape of the implant 320 for the remainder of the delivery and implantation procedure after the sleeve is retracted.

In a preferred embodiment, the implant 320 is substantially close to its maximal circumference when it is advanced from the sheath 362 and thus the deployment members 310 reach an expanded configuration immediately upon retraction of the sleeve 364. In another embodiment, the annular implant 320 is compressed when it is advanced from the sheath 362 and when the deployment members 310 are advanced through it such that the deployment members 310 expand only slightly upon retraction of the sleeve 364, such as in the position shown in FIG. 16C.

The adjustment tool 324 extends from the implant 320 in the left atrium 342 through the sheath 362 to the control interface 366. The adjustment tool 324 is connected to the adjustment mechanism 322 on the annular implant 320 and allows adjustment of the annular implant's size or shape through a corresponding controller on the control interface 366. Preferably, the connection between the adjustment tool 324 and the adjustment mechanism 322 allows for varying angles of connection. The varying angle connection can have a multiplicity of forms. In one embodiment, the adjustment tool 324 is connected to the adjustment mechanism 322 by a rotating, or universal, hinge at the distal end of the adjustment tool 324. When the implant 320 is housed in the sheath 362 and when it is advanced from the sheath 362, the adjustment tool 324 extends at an approximately 45° angle to the long axis of the implant 320. Alternatively, when the implant 320 is oriented perpendicular to the sheath 362, the adjustment tool 324 extends perpendicular to the long axis of the implant 320, and the hinge is straight.

Figure 24:
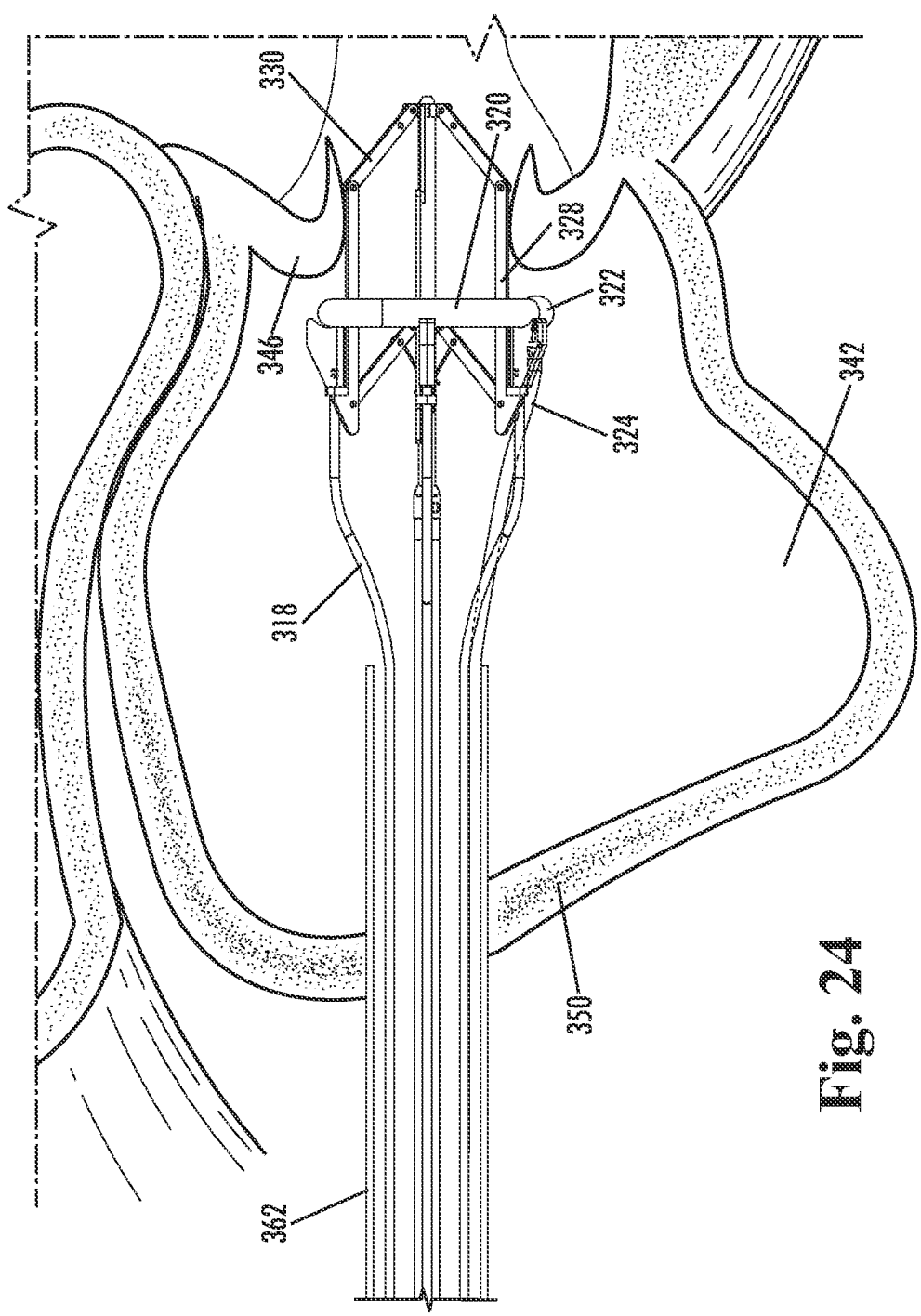
FIG. 24 is a schematic view showing the annular implant delivery device of FIG. 16 anatomically positioned in the mitral annulus of a heart with the device in an expanded configuration.

As shown in FIG. 23, the delivery device 300 is advanced further such that the distal regions 330 of the deployment members 310 contact and spread the mitral leaflets 346. The device 300 is then advanced until the deployment regions 328 of the deployment members 310 extend through the mitral valve 344 but the implant 320 does not yet contact the annulus, as shown in FIG. 24.

While the deployment members 310 extend through the annulus, but prior to contacting the implant 320 with the annulus, the implant 320 may be adjusted to a larger circumference, as desired for the surgical application. In one embodiment, the circumference of the implant 320 is adjusted by rotating a handle or knob on the proximal end of the adjustment tool 324. The adjustment tool 324 can include a display mechanism, either connected to a counting mechanism in the implant 320 or with an internal counting mechanism, to show the number of rotations made in the implant 320. The number of rotations correlates to size of the implant 320 such that the display can be used to determine the size of the implant 320 before and during implantation. Alternatively, or in addition, the control interface 366 can include a display mechanism, connected to a measuring mechanism in the implant 320, to show a force on or inside the implant 320, such as torsion or radial force or pressure at a given point, which can be used to gauge what type of adjustment is appropriate. The adjustment tool 324 can also have a slip-clutch to disengage further adjustment if the forces would otherwise damage the implant 320.

Figure 25:
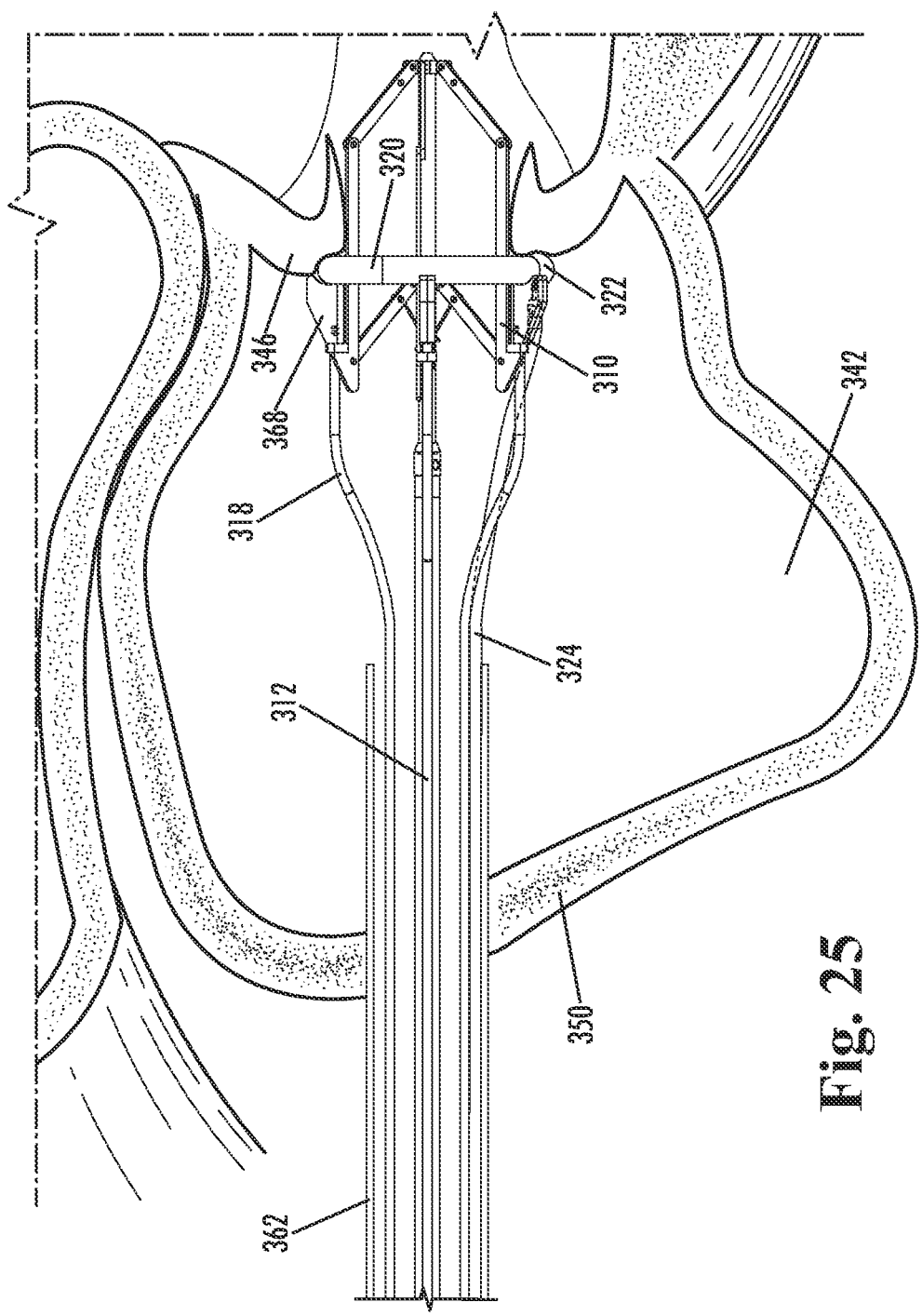
FIG. 25 is a schematic view showing the annular implant delivery device of FIG. 16 anatomically positioned in the mitral annulus of a heart with the device in an expanded configuration. The annular implant is shown anatomically positioned in the mitral annulus after it has been advanced to contact the mitral annulus.

The device 300 is then advanced such that the implant 320 contacts the annulus and the top of the annulus blocks the implant 320 from advancing further, as shown in FIG. 25. Alternatively or in addition to the above expansion, the implant 320 can be adjusted to a larger circumference once the implant 320 contacts the annulus. Contact with the annulus can be confirmed visually using TEE or by touchdown sensors, as described above. The outward force from the biasing members 360 tracking the shape of the implant 320 forces the annulus to conform from its natural configuration to the size and shape of the implant 320. The adjustment mechanism 322 on the implant 320 permits expansion control. Furthermore, the angle of the implant 320 can be controlled with the orientation of the control interface 366. This makes the annulus more suitable for implantation by placing it in a desired orientation and by creating definitive points of attachment between the implant 320 and the annulus.

Figure 26A:
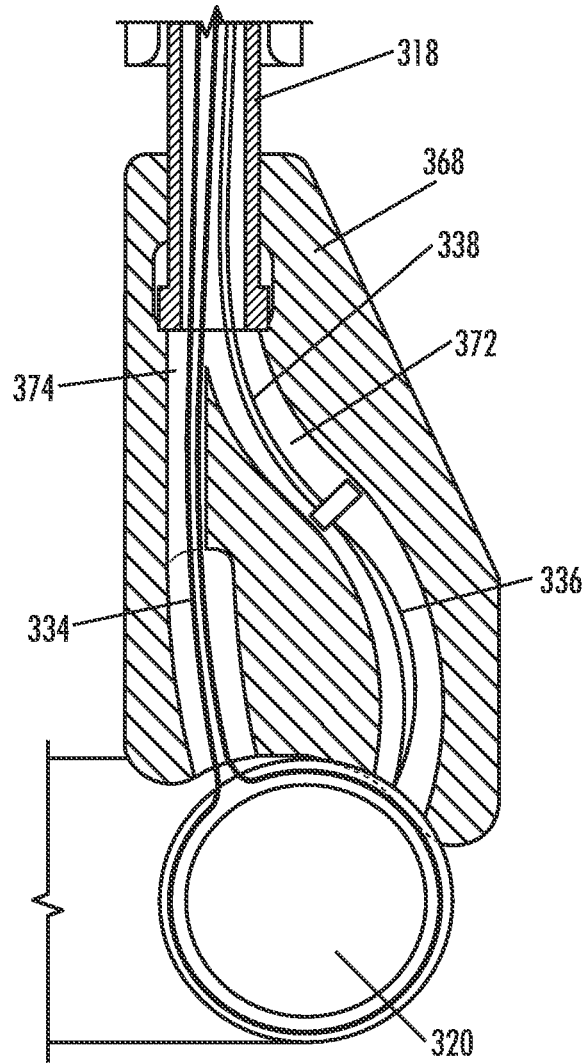
Figure 26B:
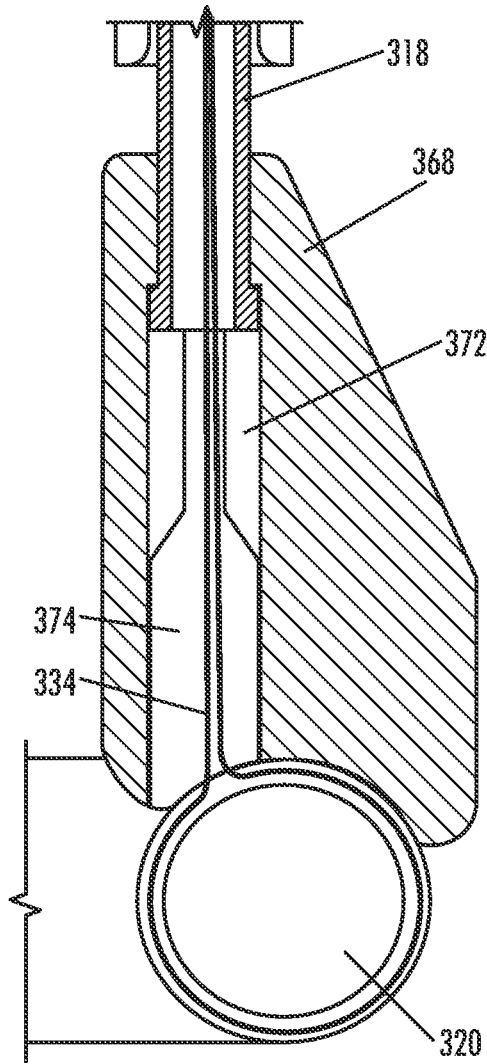

As shown in FIG. 25, when the annular implant 320 is at the desired position within the annulus and has the desired implant circumference, the implant 320 is secured to the annulus using attachment elements (shown in detail in FIGS. 26A-C). The saddle members 368 hold the distal portions of the barrels 318 in a constant orientation with respect to the implant 320, such that the distal end of each barrel 318 is facing the implant 320 in the desired position for deployment of the attachment elements into the implant 320. Prior to deploying attachment elements to attach the implant 320 to the annular tissue 340, the control interface 366 can be used to exert a downward force on all or part of the annular implant 320 to create a snug interface and aid secure attachment of the implant 320 to the annular tissue 340. Because it includes a controller corresponding to each barrel 318, the control interface 366 has multi-point control over the implant 320, like a marionette board.

The attachment elements are deployed from the barrels 318 into the implant 320 and the annular issue to attach the implant 320 to the tissue 340. Each barrel 318 can have one or more attachment elements, or certain barrels 318 can have no attachment elements. The attachment elements are located in the distal portion of the barrels 318 and are deployed using attachment element release members located in each barrel 318 proximal to the attachment elements. The control interface 366 contains a controller corresponding to each barrel 318, which includes a mechanism for advancing the attachment element release member to deploy the attachment element from the barrel 318. In one embodiment, the attachment elements are made of nitinol and have a memory coil shape such as those shown in FIGS. 9A-D, described in the context of another device embodiment. Attachment elements made of a memory shape material can have a variety of relaxed configurations, such as those shown in FIGS. 10A-H. The lumen of the barrels 318 can have a variety of configurations which keep the memory shape attachment elements 336 fittingly situated, such as those shown in FIGS. 11A-F.

The barrels 318 may contain separate compartments along the entire length of the barrel 318, or the barrels 318 may have a junction at which they split into separate slots at a point in their distal region. Various embodiments of the barrel 318 and saddle member 368 are shown in FIGS. 26A-D. FIG. 26A shows a cross-section of a barrel 318 embodiment which splits into two adjacent slots, one slot 372 containing an attachment element 336, shown as a shape memory clip, and the other slot 374 containing an anchoring element 334, shown as a suture. The slots 372, 374 are adjacent to one another in a radial direction, the suture-containing slot 374 being toward the center of the device 300 and the clip-containing slot 374 between toward the outside of the device. The suture 334 exits the barrel 318, wraps around the implant 320, and re-enters the barrel 318, securing the implant 320 to the barrel 318. Once it is desired to detach the implant 320, the suture 324 may be cut and removed, as described above. The attachment element 336 remains fittingly situated in the distal portion of the slot 372 until it is deployed.

FIG. 26B shows a cross-section of an embodiment of the barrel 318 which splits into three adjacent slots, one slot 372 containing an attachment element 336 and the other two slots 374 containing anchoring elements 334. Instead of being adjacent in a radial direction, as in the embodiment of FIG. 26A, the slots 372, 374 are adjacent in a circumferential direction, such that the attachment element 336 will deploy between the two points where the sutures 334 wrap around the implant 320. It may be desirable to use such an orientation to avoid contact between the suture(s) 334 and the attachment element 336 when the attachment element 336 is deployed. The cross-section is taken through one of the slots 374 containing a suture anchoring element 334. A portion of the attachment element-containing slot 372 is visible behind it. The third slot, also containing an anchoring element 334, is behind those in the cross-section and is not visible. FIG. 26C is a perspective view showing the circumferential slots 372, 374 in the embodiment of FIG. 26B. In one embodiment, the barrel 318 splits into only two slots 372, 374—one containing an attachment element 336 and the other containing an anchoring element 334—that are adjacent in a circumferential direction.

FIG. 26D shows an embodiment with the barrel 318 containing three circumferentially adjacent slots 372, 374, as in FIG. 26B, and containing an elongated groove cut into the outside of the attachment element-containing slot 372 and into the outside of the saddle member 368. The groove 376 creates an opening through which a portion of the attachment element 336 can exit prior to reaching the distal portion of the barrel 318. The groove 376 advantageously allows more secure attachment of the proximal end of the attachment element 336. FIG. 26E is a perspective view showing the embodiment of FIG. 26D. The cross-section in FIG. 26D is taken through the elongated groove 376 and through the middle slot 372. Operation of an embodiment with an elongated groove 376 is shown in FIGS. 26F-G. In FIG. 26F, the attachment element release member 338 has partially advanced the attachment element 336, shown as a nitinol clip, through the appropriate slot 372 in the barrel 318. The distal tip of the attachment element 336 has proceeded through the implant 320 into the annular tissue 340 and has begun curling to take on its memory coil shape. The proximal end of the attachment element 336 remains fittingly situated within the slot 372 in the barrel 318. The proximal end of the attachment element 336 exits the barrel 318 as soon as the proximal tip reaches the groove 376. In FIG. 26G, the proximal end of the attachment element 336 has exited the barrel 318 through the elongated groove 376 and has begun to take its memory coil shape, which curls the proximal tip into the implant 320.

Figure 26H:
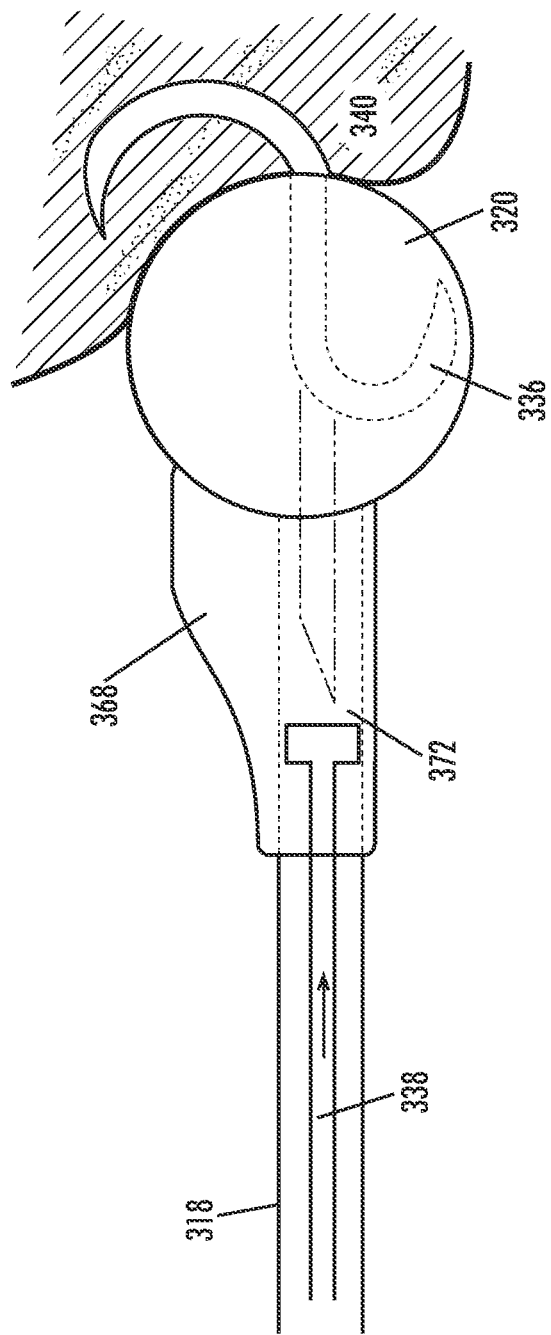
FIG. 26H is a schematic view showing another embodiment of an attachment element exiting from the barrel embodiment of FIG. 26D.

In a preferred embodiment, each end of the attachment element 336 has a memory coil shape in an opposite direction, such that the relaxed shape resembles a "S," as shown in FIG. 26H. The distal end of the attachment element 336 curls in the tissue 340 toward the implant 320. The proximal end of the attachment element 336 curls in the opposite direction back into the implant 320, thereby enabling more secure attachment because a greater length of the attachment element 336 remains within the implant 320. The attachment element 336 can also have different memory shapes in different regions. The attachment element 336 can also possess barbs or hooks at the ends to assist retention.

To prevent the distal end of the attachment element 336 from exiting through the groove 376 before or during deployment, the distal end may be encased, such as in a pin, so that it does not have a memory shape effect and thereby remains straight as it proceeds through the slot 372 into the implant 320, instead of curling out through the groove 376. Alternatively, the distal tip of the attachment element 336 can be secured in the implant 320 while housed in the sheath 362 prior to use in a surgical procedure. With a sufficiently stiff material used inside the implant 320, analogous to a hollow pin carrying the attachment element 336, the distal tip can be secured in the implant 320 so that it does not begin curling until it is advanced into the tissue 340.

After each of the attachment elements 336 has been deployed and the implant 320 is attached to the annulus, the implant 320 is detached from the barrels 318. To detach the implant 320 from the barrels 318, the suture anchoring elements 334 must be removed from around the implant 320. The sutures 334, which extend from the control interface 366 distally through each barrel 318, around the implant 320, and back proximally through the barrel 318 to the control interface 366, are cut at the control interface 366 and may be pulled to remove the suture 334 from around the implant 320. Leaving the implant 320, adjustment mechanism 322, and adjustment tool 324 in place at the mitral annulus, the deployment members 310 are withdrawn from the annulus into the left atrium 342. Once the deployment members 310 have been withdrawn from the implant 320 and there is no outward force on the implant 320, the implant 320 is more flexible and no longer forces its shape on the annulus. The annulus tends to return to its natural configuration. For beneficial attachment, the annulus should conform to the shape of the implant 320 only for the time needed to attach the implant 320.

The deployment members 310 must collapse to fit back into the sheath 362. To allow the deployment members 310 to collapse, the sleeve 364 is slid back over the biasing members 360 to pull them inward. The deployment members 310 can be withdrawn into the sheath 362 first by pulling on the controller that corresponds to the central support member 312. The directing cuffs 370 slide proximally along the barrels 318 toward the sheath 362. As the deployment members 310 collapse, the directing cuffs 370 pull the barrels 318 together so that they form a narrow ring that can be withdrawn into the sheath 362. FIG. 27 shows the deployment members 310 and in a collapsed configuration after the barrels 318 have been detached from the implant 320. As the barrels 318 are withdrawn into the sheath 362, the barrels 318 are forced inward and, in turn, the deployment members 310 are forced inward and collapsed further so they can fit back in the sheath 362.

FIG. 28 shows the implant 320, adjustment mechanism 322, and adjustment tool 324 in place at the mitral annulus after the deployment members 310 and barrels 318 have been withdrawn into the sheath 362. Once the sheath 362 is removed from the patient, the adjustment tool 324 remains extending through the patient's myocardial incision and chest incisions to enable post-operative adjustment. The controller corresponding to the adjustment tool 324 may be removed from the control interface 366 to operate independently following the surgery, or the control interface 366 can remain intact with only the adjustment tool 324 being used post-operatively. Post-operative adjustment works in the same manner as described above in connection with a previous embodiment.

Figure 29A:
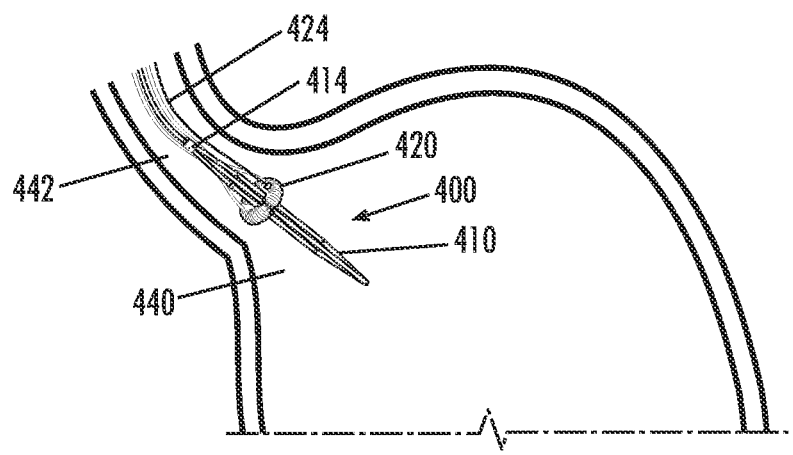
FIGS. 29A-C are a series of schematic views of one embodiment of an annular implant delivery device used to treat gastro-esophageal reflux disease.
Figure 29B:
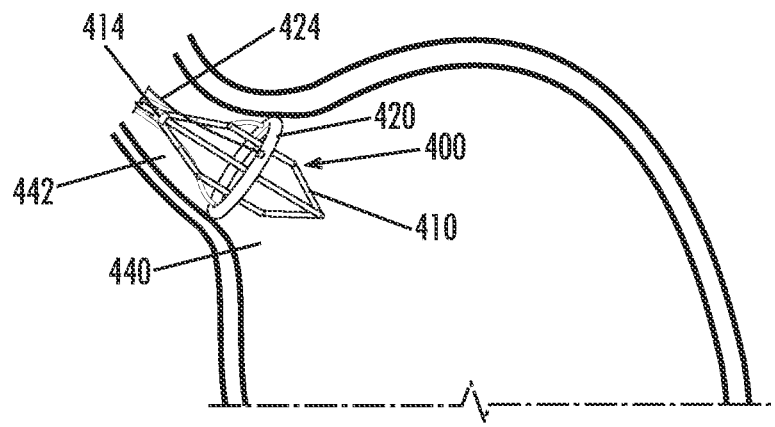
Figure 29C:
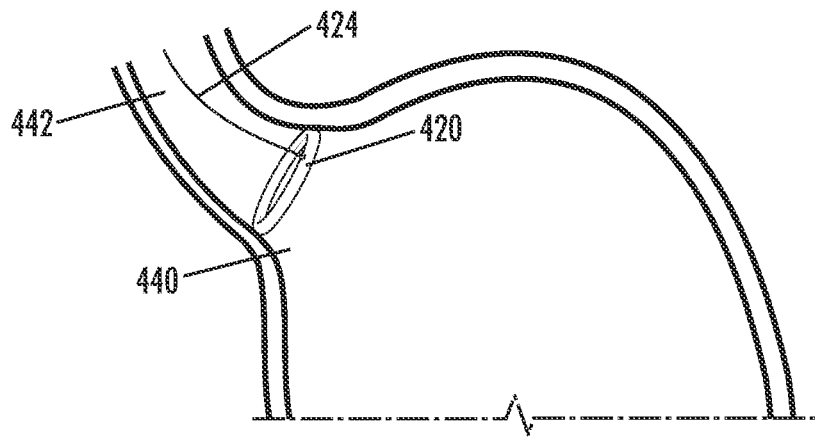

An additional embodiment of the annular implant delivery device can be used for gastrointestinal disorders such as gastro-esophageal reflux disease, a condition in which the gastro-esophageal junction lacks adequate sphincter tone to prevent the reflux of stomach contents into the esophagus, causing classic heartburn or acid reflux. Referring now to FIG. 29A, an embodiment of the annular implant delivery device 400 is passed under guidance of an endoscope through the patient's mouth and esophagus 442 toward the gastro-esophageal junction 440. Once the deployment members 410 have reached the gastro-esophageal junction 440 and the annular implant 420 is appropriately positioned at the junction 440, the deployment members 410 are expanded, as shown in FIG. 29B. Again, the deployment members 310 can be expanded by moving the proximal joining member 414 or by adjusting the circumference of the annular implant 420 using the adjustment tool 424. The implant 420 is then adjusted to its maximum deployment circumference using the adjustment tool 424 until the implant 420 is taut against the distal portion of the esophagus 442. At this point, the attachment elements (not shown) are deployed to secure the implant 420 to the distal portion of the esophagus 442. The delivery device 400 can then be retracted into the esophagus 442 and removed from the patient. Once the implant 420 is secured, as shown in FIG. 2C, the circumference of the implant 420 can be adjusted until the desired annular reduction is achieved. This can be measured by the desired effect, i.e., minimal acid reflux either by patient symptoms, pH monitoring of the esophagus, imaging studies, or other diagnostic means. If the patient should suffer from "gas bloat," a common complication of gastro-esophageal junction repair in which the repair is too tight and the patient is unable to belch, the implant 420 can be loosened until a more desirable effect is achieved.

Figure 30A:
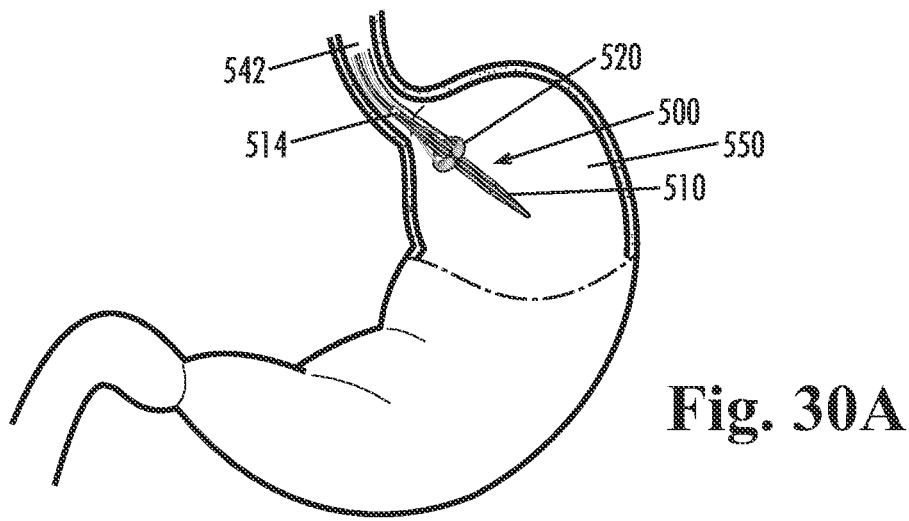
FIGS. 30A-C are a series of schematic views of one embodiment of an annular implant delivery device used in gastric bypass surgery.
Figure 30B:
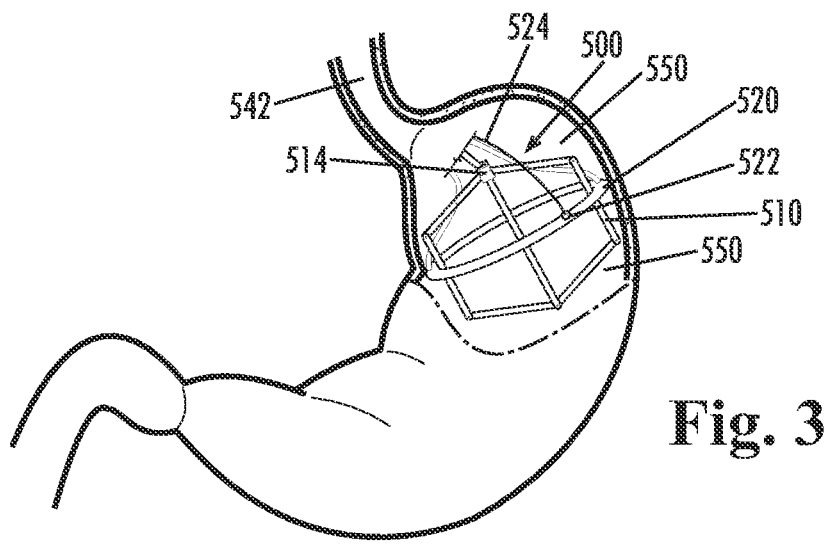
Figure 30C:
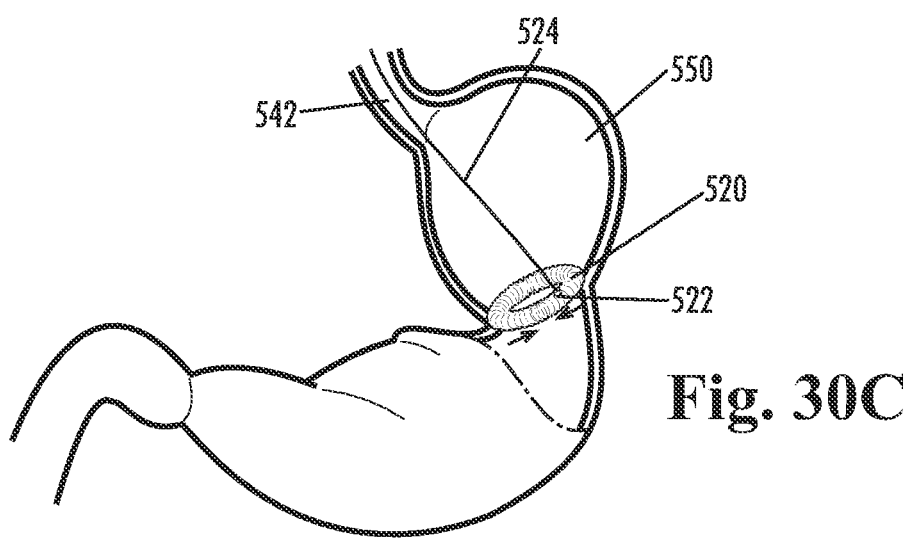

An additional embodiment of the annular implant delivery device includes adaptation for use in gastric bypass surgery for obesity disorders, a procedure in which the upper portion of the stomach is made to form a pouch to induce a fullness sensation and thus cessation of excessive eating. Referring now to FIG. 30A, an embodiment of the annular implant delivery device 500 is passed under guidance of an endoscope through the patient's mouth and esophagus 542 into the stomach 550. Once the deployment members 510 have reached the desired section of the stomach, the annular implant 520 and the deployment members 510 are appropriately expanded to extend to the stomach walls, as shown in FIG. 30B, by moving the proximal joining member 514 or by adjusting the circumference of the annular implant 520 using the adjustment tool 524 coupled to the adjustment mechanism 522. The implant 520 is then adjusted to its maximum deployment circumference using the adjustment tool 524 until the implant 520 is taut against the central portion of the stomach 550. At this point, the attachment elements (not shown) are deployed laterally to secure the implant 520 to the stomach 550. The delivery device 500 can then be retracted into the esophagus 542 and removed from the patient, leaving the implant 520 in place as shown in FIG. 30C. Once the implant 520 is secured, the circumference of the implant 520 can be adjusted until the desired annular reduction is achieved.

The present invention and the methods for its use anticipate many alternate embodiments in other potential applications in the broad fields of medicine and surgery. Among the other potential applications anticipated according to the present invention are adjustable implants for use in the treatment of morbid obesity, urinary incontinence, anastomotic strictures, arterial stenosis, cervical incompetence, ductal strictures, and anal incontinence. The preceding discussions are intended to be exemplary embodiments according to the present invention and should not be construed to limit the present invention and the methods for its use in any way. Other features and embodiments of the present invention will be apparent to those in the art in view of the present disclosure.

What is claimed is:

1. A delivery device for an annular implant comprising:
   an annular implant having an adjustable dimension, wherein the annular implant comprises an adjustment mechanism configured to be releasably attached to an adjustment tool and for incrementally adjusting a size or shape of the annular implant, and wherein the device further comprises an elongated adjustment tool having a proximal end and a distal end releasably attached to the adjustment mechanism, whereby the annular implant size or shape can be incrementally adjusted by the adjustment tool;
   a plurality of movable elongated deployment members, each having a proximal end and a distal end and an annular implant deployment region therebetween releasably disposable within an annulus of the annular implant;
   an elongated support member having a proximal end and a distal end and being substantially parallel to the implant deployment regions of the deployment members;
   a distal joining member fixedly attached to the distal end of the support member and joined to the distal ends of the deployment members; and
   a proximal joining member coupled to the proximal end of the support member and joined to the proximal ends of the deployment members, wherein the deployment members extend between the distal and proximal joining members and wherein the implant deployment regions of the deployment members extend between the distal and proximal joining member substantially parallel to the support member;
   wherein the deployment members are retractably expandable by an expansion means to an expanded configuration wherein the implant deployment regions are substantially parallel to the support member and wherein the implant deployment regions of the deployment members are substantially parallel to each other in the expanded configuration.

2. The delivery device of claim 1, wherein the expansion means comprises a plurality of biasing members extending between the central support member and a plurality of respective deployment members, wherein each biasing member exerts an expanding force on the corresponding deployment member.

3. The delivery device of claim 2, further wherein expansion of the deployment members is limited by the size or shape of the annular implant.

4. The delivery device of claim 1, wherein the proximal joining member is slidably attached along the central support member.

5. The delivery device of claim 4, wherein the expansion means is a deployment articulation member in communication with the proximal joining member, wherein the proximal joining member is movable distally to expand the deployment members and proximally to contract the deployment members.

6. The delivery device of claim 1, wherein expansion of the deployment members causes the annulus to conform to the size and shape of the annular implant.

7. The delivery device of claim 1, further comprising a control interface, wherein the control interface allows the annular implant to be advanced and oriented independent of the deployment members.

8. The delivery device of claim 1, wherein the adjustment tool is re-attachable to the adjustment mechanism after release.

9. The delivery device of claim 1, wherein at least a portion of the deployment members comprise a radio-opaque or echo-opaque material.

10. The delivery device of claim 1, further comprising:
    at least one elongated barrel, each barrel having a proximal end and a distal end and being movably affixed adjacent each distal end to the deployment region of a deployment member;
    an attachment element within a distal portion of each barrel for attaching the annular implant to annular tissue, wherein the attachment element is made of a shape memory alloy and is fittingly situated within the barrel to guide the attachment element in a predetermined orientation with respect to the barrel; and
    a corresponding elongated attachment element release member extending through the proximal end of the barrel to communicate with the attachment element;
    wherein the attachment element is delivered through the distal end of the barrel into the annular implant and annular tissue by manipulating the attachment element release member.

11. The device of claim 10, wherein the attachment element is made of nitinol.

12. The device of claim 10, wherein the attachment element comprises a radio-opaque or echo-opaque material.

13. The device of claim 10, wherein the barrel has an internal surface configured to guide the attachment element in a predetermined orientation.

14. The device of claim 10, wherein the barrel has an elongated cut-out designed to allow a proximal portion of the attachment element to exit the barrel before the proximal end of the attachment element reaches the distal end of the barrel.

15. The delivery device of claim 10, further comprising an anchoring element extending from at least one barrel, wherein the anchoring element engages the annular implant, releasably attaching the annular implant to the barrel.

16. The delivery device of claims 15, wherein the anchoring element releases from the annular implant when the annular implant is secured to annular tissue and force is applied to the barrel in a proximal direction.

17. The delivery device of claim 10, further comprising an anchoring element extending from at least one barrel, wherein the anchoring element wraps around the annular implant, releasably attaching the annular implant to the corresponding barrel.

18. The delivery device of claim 17, wherein at least a portion of the barrel comprises a plurality of slots, further wherein at least one slot contains an attachment element and at least one separate slot contains an anchoring element.

19. The delivery device of claim 10, wherein the distal end of each barrel is secured to the annular implant in an orientation such that the distal end of each barrel is facing the annular implant when the deployment members are in an expanded configuration.

20. The delivery device of claim 10, wherein at least one point on each deployment member is slidably attached to a corresponding barrel.

21. A device for delivering and attaching an annular implant that delivers the annular implant to a desired annulus and attaches the annular implant to the annulus by deploying at least one memory shape attachment element into the annular implant and annulus, the device comprising:
> at least one elongated barrel having a longitudinal axis, the barrel having a proximal end and a distal end defining a shaped opening; and
> at least one anchoring element for releasably attaching the at least one barrel to the annular implant;
> at least one elongated attachment element having spaced apart proximal and distal tips received within a portion of the barrel adjacent the shaped opening for attaching the annular implant to the annulus; and
> an attachment element release member within the barrel to communicate with the attachment element, the attachment element moveable along the longitudinal axis of the barrel;
> wherein the attachment element is discharged longitudinally through the shaped opening at the distal end of the barrel into the annular implant and annular tissue by manipulating the attachment element release member into engagement with the proximal tip of the attachment element, whereby the attachment element moves along the longitudinal axis of the barrel from its received position within the barrel to a discharge position outwardly of the shaped opening; and
> deployment members configured for conforming the annulus to match the size and shape of the annular implant prior to attaching the annular implant to the annulus.

22. A device for delivering an annular implant to a desired annulus, comprising:
> an annular implant defining an opening and having an adjustable dimension, wherein the annular implant comprises an adjustment mechanism configured to be releasably attached to an adjustment tool and for incrementally adjusting a size or shape of the annular implant, and wherein the device further comprises an elongated adjustment tool having a proximal end and a distal end releasably attached to the adjustment mechanism, whereby the annular implant size or shape can be incrementally adjusted by the adjustment tool;
> an elongated support member having a distal end;
> a spreading mechanism configured to be releasably disposable within the opening of the annular implant, wherein the spreading mechanism is expandable within the opening of the annular implant to conform to the size and shape of the annular implant, wherein the spreading mechanism has a distal end fixedly attached to the distal end of the elongated support member which extends through the spreading mechanism and a proximal end coupled to the support member spaced from the distal end of the support member; and
> means operatively associated with the spreading mechanism for reshaping an annulus to conform to the size and shape of the annular implant when delivering the annular implant on the spreading mechanism to the annulus by expanding the spreading mechanism within the opening of the annular implant.

* * * * *